United States Patent [19]

Blum et al.

[11] Patent Number: 5,500,343
[45] Date of Patent: * Mar. 19, 1996

[54] ALLELIC ASSOCIATION OF THE HUMAN DOPAMINE(D2) RECEPTOR GENE IN COMPULSIVE DISORDERS

[75] Inventors: Kenneth Blum, San Antonio, Tex.; E. P. Noble, Los Angeles, Calif.; P. J. Sheridan, San Antonio, Tex.

[73] Assignees: Board of Regents, The University of Texas System, Austin, Tex.; Regents of the University of California, Berkeley, Calif.

[*] Notice: The portion of the term of this patent subsequent to May 11, 2010, has been disclaimed.

[21] Appl. No.: 909,383

[22] Filed: Jun. 24, 1992

Related U.S. Application Data

[63] Continuation-in-part of Ser. No. 826,222, Jan. 23, 1992, Pat. No. 5,210,016, and a continuation-in-part of PCT/US91/00855, Feb. 7, 1991, which is a continuation of Ser. No. 477,057, Feb. 7, 1990, abandoned.

[51] Int. Cl.$^6$ .............................. C12Q 1/68; C12P 19/34; C07H 21/04; C12N 15/00
[52] U.S. Cl. ............................. 435/6; 435/91.1; 435/91.2; 435/810; 536/23.1; 536/23.5; 536/24.33; 935/31; 935/78
[58] Field of Search ................... 435/6, 91, 975, 435/91.1, 91.2, 810; 536/23.1, 23.5, 24.31, 24.33; 935/78, 31

[56] References Cited

U.S. PATENT DOCUMENTS 5,210,016  5/1993  Blum et al. ................................. 435/6

OTHER PUBLICATIONS

Suarez et al., *Genomics* vol. 19, pp. 12–20 (1994).
Holden, *Science*, vol. 264, pp. 1696–1697, 17 Jun. 1994.

*Primary Examiner*—W. Gary Jones
*Assistant Examiner*—Bradley L. Sisson
*Attorney, Agent, or Firm*—Arnold, White & Durkee

[57] ABSTRACT

In an important embodiment, the present invention concerns a method for detecting compulsive disorder susceptibility of a human. The method comprises initially obtaining a DNA sample of said human and then determining the presence or absence of a particular human $D_2$ receptor gene allele in said sample. Detection of said allele in the sample is indicative of susceptibility to compulsive disorder. A most preferred embodiment is to detect a susceptibility to alcoholism and cocaine dependence, particularly because said allele has been found to be present in a majority of clinically diagnosed alcoholics and cocaine users. The human $D_2$ receptor gene A1 and B1 alleles are most preferably detected in said sample.

10 Claims, 16 Drawing Sheets

FIG. 3A
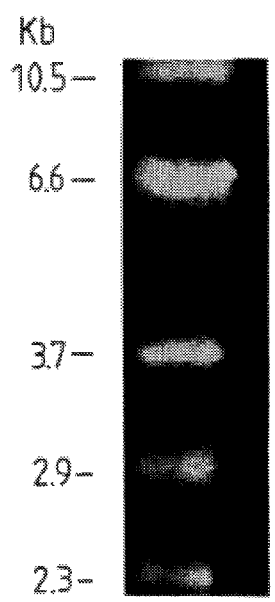
FIG. 3B
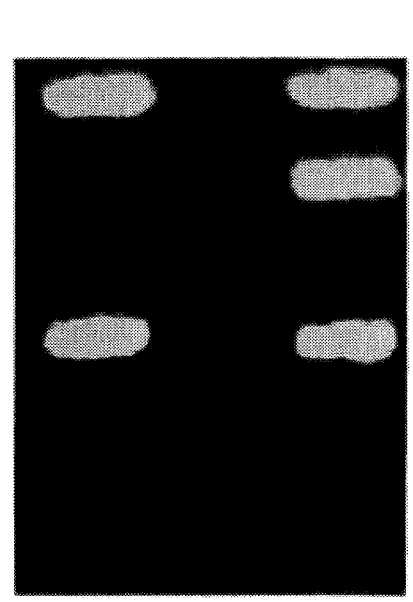
A2/A2    A1/A2
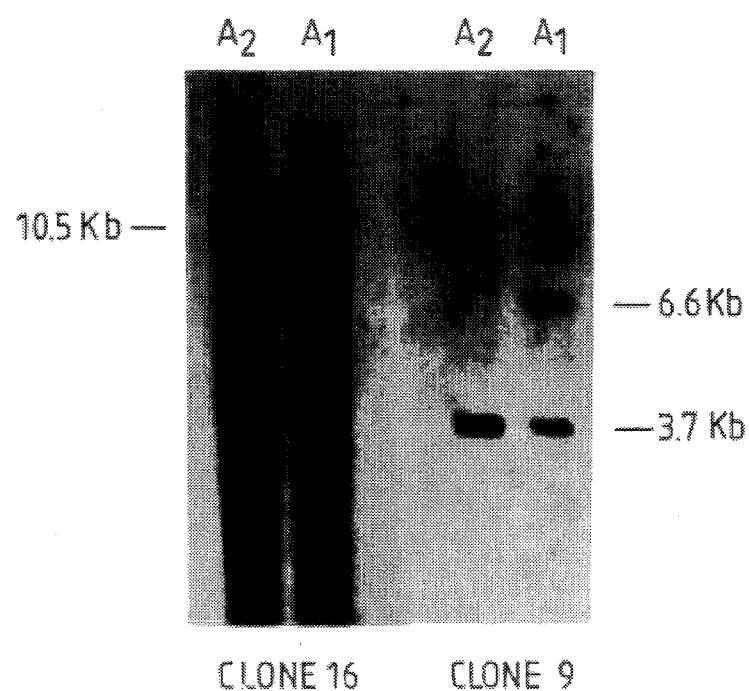
CLONE 16    CLONE 9
FIG. 8

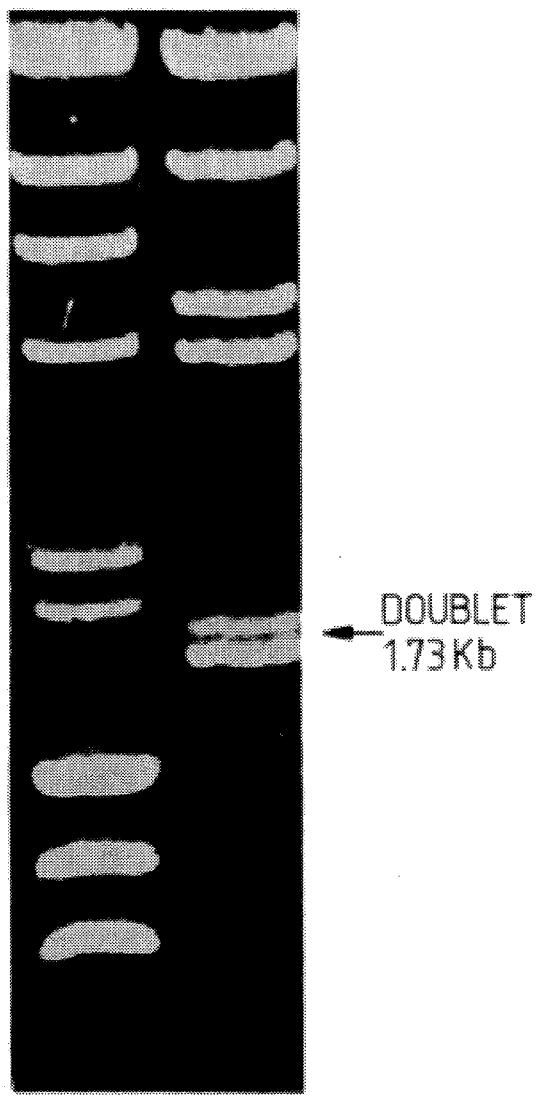
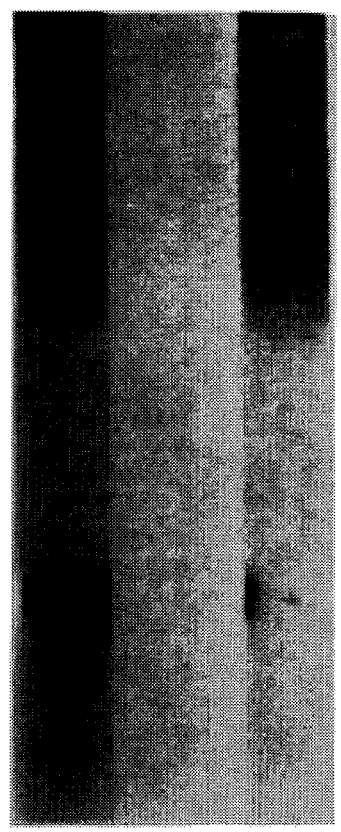
FIG. 7A
FIG. 7B

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

GAGGGTGAAA G                                                      11

( 2 ) INFORMATION FOR SEQ ID NO: 2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GAGGGGGAAA G                                                      11

( 2 ) INFORMATION FOR SEQ ID NO: 3:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CACCACGGTC T                                                      11

( 2 ) INFORMATION FOR SEQ ID NO: 4:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CACCATGGTC T                                                      11

( 2 ) INFORMATION FOR SEQ ID NO: 5:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 5:

GAGTCTTCAG AGGGT  15

(2) INFORMATION FOR SEQ ID NO: 6:

(i) SEQUENCE CHARACTERISTICS:
  (A) LENGTH: 14 base pairs
  (B) TYPE: nucleic acid
  (C) STRANDEDNESS: single
  (D) TOPOLOGY: linear (xi) SEQUENCE DESCRIPTION: SEQ ID NO: 6:

TGCTGTGGAG ACCG  14

ALLELIC ASSOCIATION OF THE HUMAN DOPAMINE(D2) RECEPTOR GENE IN COMPULSIVE DISORDERS

The United States government has certain rights in the present invention because research relating to its development was partially supported by funds from NIDA, DA 04268 and DA 0146.

This application is a continuation-in-part of applications PCT/US91/00855, filed Feb. 7, 1991, and Ser. No. 07/826,222, filed Jan. 23, 1992, now U.S. Pat. No. 5,210,016, which is a continuation of Ser. No. 07/477,057, filed Feb. 7, 1990; the contents of all of which are incorporated by reference herein.

The present invention relates to molecular genetic evidence, through the use of RFLP and PASA analyses, that alleles in the human dopamine D2 receptor gene are more significantly associated with compulsive disorders than with controls. The occurrence of these compulsive disorder-associated polymorphisms has a statistically significant predictive value in the classification of subtypes of compulsive disorders.

The identification of genetic markers that are closely linked to compulsivity means that the gene's inheritance can be followed, leading to simple tests for diagnosing vulnerable carriers and potential disease victims, and may lead to gene therapy. A diagnosed genetic potential susceptibility to substance abuse can encourage behavioral intervention to prevent the onset of disease on the part of the individual diagnosed or, in the case of adopted children, on the part of the adoptive parents.

The tendency of certain individuals to display compulsive disorder behavior is well known and includes individuals with an excessive desire for substances classed as psychoactive drugs including, but not limited to alcohol, opiates, and food. Whether alcoholism is a psychiatric illness or a biological disease has been a controversial question, but there is some agreement that there are probably similar biochemical mechanisms for alcohol and opiates in terms of behavioral and pharmacological activities (Blum et al., 1988).

Some authors believe that dopaminergic cells are implicated in the rewarding action of alcohol (Korpi et al., 1987), opiates (Wise and Bozarth, 1982) and cocaine (Wise and Bozarth, 1982). In contrast, others (Amit and Brown, 1982) argue that at least alcohol/opiates/cocaine and alcohol reinforcing effects are mediated primarily by noradrenergic and not dopaminergic systems in the brain. In either case, the cause and effect of substance abuse, including alcoholism, appears to be biogenic and the ability to identify allelic gene segments associated with specific substance abuse behavior will allow development of predictive tests for compulsive disorder behavior patterns, for example, those involving substance abuse.

Alcoholism is a major and devastating health problem with an unknown etiological basis. The question of whether environment or heredity is the prime determinant for the development of alcoholism continues to receive extensive attention throughout the world, and has recently involved the Supreme Court of the United States (Traynor v. Turnage, United States Supreme Court, 1988). However, family, twin, and adoption studies (Kai, 1960; Goodwin, 1971; Goodwin, 1979; Cloninger et al., 1981) are pointing to genetic factors as significant contributors to alcoholism. These studies also demonstrate that other forms of mental illness such as schizophrenia and other major psychoses are not found at frequencies in families of alcoholics higher than in the general population. This would suggest that alcoholism is a primary disease.

Alcoholism currently is viewed as a heterogeneous entity arising from a combination of biopsychosocial factors (American Psychiatric Association, 1987). In regard to biological factors, an extensive literature reveals a wide range of potential physiological (Begleiter et al., 1981; Gabrielli et al., 1982; Pollock et al., 1983; Begleiter et al., 1984; O'Connor et al., 1986; Whipple et al., 1988) and biochemical (Takahashi et al., 1976; Wiberg et al., 1977; Sullivan et al., 1979; Fowler et al., 1982; Oreland et al., 1983; Alexopoulos, 1983; von Knorring et al., 1985; Diamond et al., 1987; Tabakoff et al., 1988; Mochly-Rosen et al., 1988) markers in the risk for alcoholism. Moreover, family pedigree linkage analysis has implicated chromosomes 4, 6 and 11, but not specific gene markers, in the genetic risk for alcoholism (Shill et al., 1975; Shigeta et al., 1980; Hill et al., 1987).

Restriction Fragment Length Polymorphism (RFLP) offers a powerful molecular genetic tool for the direct analysis of the human genome to determine elements that provide predisposition to genetic diseases (Kan and Dosy, 1978; Gusella et al., 1983; Gerhard et al., 1984; Saraiva et al., 1986; Bartlett et al., 1987; St. George-Hyslop et al.; Barrow et al., 1987; Rommens et al., 1989; Riordan et al.; Kerem et al.). This technique has been used to demonstrate a structural mutation in the gene that codes for an enzyme involved in alcohol metabolism (aldehyde dehydrogenase) which leads to the loss of this enzyme's ability to metabolize acetaldehyde. This altered gene is prevalent among Orientals (Bosron and Li, 1979; Agarwal et al., 1981; Bosron et al., 1983; Yoshida et al., 1983; Yoshida et al., 1984; Goedde and Agarwal, 1987) and may explain the well-known alcohol-flush syndrome as a protective factor in this population. Prior to the present inventors' work, no specific gene abnormality had been identified which could regulate alcohol-seeking behavior, or was associated with alcoholism in humans.

Numerous studies indicate that, in animals, genetic control of neurotransmitter synthesis, metabolism, regulation, and receptor activity mediates reward in the meso-limbic circuitry of the brain (Lippa et al., 1973; Ahtee and Eriksson, 1975; Dibner et al., 1980; Wise, 1980; Barbaccia et al., 1981; Blue and Payne, 1991), as well as drug (e.g., ethanol) seeking behavior (Ticku and Burch, 1980; Blum et al., 1982; Blum et al., 1983; Blum et al., 1986; Gianoulakis and Gupta, 1986; Blum and Topel, 1986; Murphy et al., 1987; Murphy et al., 1988). In the normal person, a single neurochemical agent produces a specific effect in a given subsystem known to be involved in reward. Other agents are similarly at work in related or parallel sequences. In patterns of stimulation or inhibition these subsystems interact and the effects branch and spread—like a cascade, leading to feelings of wellbeing: the ultimate reward. This is the cascade theory of reward (Lippa et al., 1973; Ahtee and Eriksson, 1975; Dibner et al., 1980; Wise, 1980; Barbaccia et al., 1981; Blue and Payne, 1991).

If a deficiency or imbalance interrupts or distorts the cascade, the result is a displacement of the feeling of well-being by anxiety or anger; or by craving for a substance that masks or relieves the bad feeling—for example, alcohol. This is the cascade theory of alcoholism (Lippa et al., 1973; Ahtee and Eriksson, 1975; Dibner et al., 1980; Wise, 1980; Barbaccia et al., 1981; Blue and Payne, 1991).

Although the neurotransmitter system is extremely complex and still not completely understood, FIG. 1 identifies the central reward areas (Roman numerals). FIG. 2 demonstrates the major interactions of what are believed to be key components (Arabic numerals): serotonin, dopamine, norepinephrine, GABA, and enkephalins; related enzymes; and receptors. Other agents are certainly involved, but their identity and their interactions are still under study. Roman numerals are keyed to FIG. 1. From the known activity of these agents in the reward areas, the following interactions very likely take place:

Serotonin (1) in the hypothalamus (I) indirectly activates opiate receptors (2) and causes a release of enkephalins in the ventral tegmental region A10 (II). The enkephalins inhibit the firing of GABA (3) which originates in the substantia nigra A9 region (III).

GABA's normal role, acting through GABA B receptors (4), is thought to inhibit and control the amount of dopamine (5) released at the ventral tegmental region (II) for action at the nucleus accumbens (IV). When the dopamine is released in the nucleus accumbens it activates dopamine D2 receptors (6), a key reward site. This release is also regulated by enkephalins (7) acting through GABA (8). The supply of enkephalins is controlled by the amount of the neuropeptidases (enzymes) (9) which destroy them.

Dopamine may also be released into the amygdala (V). From the amygdala, fopamine (10) reaches the hippocampus (VI), and in CA1 cluster cells (VII) stimulates dopamine D2 receptors (11), another reward site.

An alternate pathway involves norepinephrine (12) in the locus ceruleus A6 (VIII) whose fibers project into the hippocampus at a reward area centering around cluster cells which have not been precisely identified, but which have been designated as CAx (IX). When GABA A receptors (13) in the hippocampus are stimulated, they cause the release of norepinephrine (14) at the CAx site.

In the cascade theory of reward, these interactions may be viewed as activities of subsystems of a larger system, taking place simultaneously or in sequence, merging in cascade fashion toward a specific effect in the reward areas of the brain: the generation of feelings of well-being.

In the cascade theory of alcoholism, genetic anomalies, long-continued stress, or long-term abuse of alcohol can lead to a self-sustaining pattern of abnormal craving.

The dopamine receptor has been implicated as a prime target site in cells of the brain reward system (Liljequist, 1978; Newlin et al., 1981; Mereu et al., 1984; Stein and Belluzzi, 1986; Govoni et al., 1986; Valveflus et al., 1989; Fadda et al., 1989). Five major dopaminergic systems in the human brain have been identified ($D_1$–$D_5$). The nigrostriatal is involved in the initiation and execution of movement; the tuberoinfundibular is responsible for the regulation of peptide secretion from the pituitary; and the mesolimbic tract controls emotional stability and affect. Mediating these effects of dopamine are two receptor subtypes, $D_1$ and $D_2$ (also designated as D1 and D2), each of which is coupled to different second messenger systems. The $D_1$ receptor has been implicated in the sleep disorder, insomnia. Most recently, a $D_3$ receptor has been found (Sokoloff et al., 1990) and is also implicated in limbic system function.

Important clinically relevant studies on the pharmacology of $D_2$ receptors indicated that antipsychotic drugs display high affinities for the receptor. Other work suggested that the $D_2$ receptor is involved in movement disorders, i.e. Parkinson's disease and tardive dyskinesia, tumors of the pituitary, and compulsive disease.

A cDNA encoding for rat dopamine ($D_2$) receptor has been isolated (Bunzow et al., 1988). This receptor has been implicated in the pathophysiology of certain diseases, including drug addiction. The same laboratory localized the receptor gene to chromosome 11 (Grandy et al., 1989).

Partial sequence analysis revealed that the genomic clone lambda-$hD_2G1$ ($\lambda hD_2G1$) (ATCC #61354 is the lysate, ATCC #61355 is the phage DNA) contains the last coding exon of the $D_2$ receptor and 16.5 kb of 3-prime flanking sequence. When this clone was hybridized to human metaphase chromosomes and DNA from rodent-human hybrid cells, the data were consistent with a single human dopamine $D_2$ receptor gene which mapped to the q22–q23 region of chromosome 11. This previous work provides a research tool to begin a molecular analysis of the human $D_2$ receptor in alcoholism.

Access to sequence variation in the human genome now allows construction of genetic linkage maps through the technique of RFLPs (restriction fragment length polymorphisms). This technique provides probes which are isolated from chromosome specific phage libraries constructed to contain some portion of human DNA (Maslen et al., 1988). With this tool in hand, the analysis of human gene segments is possible. The identification described herein of an apparent gene abnormality in the tissue of alcoholics is an important advance in the art and of value in objectively identifying individuals who are genetically vulnerable to alcoholism. The need for differential diagnosis and the ability to identify genetic susceptibility to substance abuse such as alcoholism has been recognized at the national level (Tabakoff et al., 1988).

In the present invention, the DNA probe $\lambda hD_2G1$ (ATCC #61354 and 61355) and an about 1.6-kb fragment of $\lambda hD_2G1$ (ATCC #61354 and 61355) effectively visualize the human dopamine ($D_2$) receptor gene. This permits evaluation of polymorphisms on the gene in a region close to the gene which could modify the function of the gene as a valuable predictor of alcoholism or other substance abuse.

Using blood samples of living alcoholics and nonalcoholics, the present inventors as well as others (Blum et al., 1991; Parsian et al., 1991; Comings et al., 1991) found a strong association of the A1 DRD2 allele in alcoholics when compared to control nonalcoholics. However, two other studies (Bolos et al., 1990; Gelernter et al., 1991), while showing a higher prevalence of the A1 allele in alcoholics (individuals with liver disease or other medical problems excluded) than controls (alcoholics not excluded), found a lack of significant allelic differences in these two groups. Cloninger, 1991 carried out a combined analysis of the above six case-control studies. He found the A1 allele to be present in 45% of 338 alcoholics and 27% of 471 controls (odds ratio=2.4) or 22% of 158 nonalcoholic controls (odds ratio=3.0). Overall, the association between alcoholism and the A1 allele was highly significant ($P<10^{-7}$), whether alcoholics were excluded or included in the controls. A reviewer concluded that the failure to screen for alcoholism in controls and the natural variation in the frequency of the A1 allele among small sample sizes accounted for two of the negative association studies. The robustness of A1 allelic association with alcoholism has been emphasized in *Archives of General Psychiatry* (Conneally, 1991) and the *Journal of the American Medical Association* (Cloninger, 1991).

Comings et al., 1991 found a lack of association of the A1 allele with schizophrenia; however, they found an association with Tourette's syndrome, a disorder frequently accompanied by a propensity for alcoholism. Nothen et al. 1991, in studying bipolar affective disorder, also found a lack of association with the alleles of the DRD2 gene. The negative association findings in the two psychiatric disorders studied thus far, stand in contrast to a growing body of evidence implicating the DRD2 gene in alcoholism and other drug dependencies (see Example 6).

In the past quarter century, there has been a dramatic escalation in the use of illicit drugs in the U.S. In response to that threat, the federal government has initiated several "Drug War" programs whose outcomes remain to be clearly established. The drug that has attracted perhaps the most serious attention is cocaine, a chemical with strong reinforcement properties, addictive capability and potential for harm. It is estimated that at least 21 million Americans have used cocaine (National Institute on Drug Abuse, 1991), with nearly one of every two Americans between the ages of 25 and 30 having tried this drug and one to 3 million are seriously dependent and in need of formal treatment (Gawin, 1991).

A variety of predominantly psychosocial theories has been advanced to account for the abuse of cocaine and other illicit drugs. However, in contrast to alcoholism, where growing empirical evidence is implicating hereditary factors, relatively little is known about the genetics of human cocaine dependence. Indeed, in the most recent drug abuse report by the U.S. government to the Congress (Department Health and Human Services Publ. No. (ADM), 1991), no mention is made of the role hereditary factors may play in cocaine dependence. This omission is not surprising as several factors could account for this lack of knowledge, including a greater interest in environmental determinants and lower overall incidence of illicit drug abuse compared to alcoholism. Moreover, the relative recency of epidemic use and abuse of illicit cocaine, in contradistinction to the longstanding use and abuse of licit alcohol, has precluded the accumulation of sufficient generational and other relevant data for analysis. Still, the few recent studies available on humans (Cadoret et al., 1986; Pickens et al., 1991) and on animals (Smolen and Marks, 1991; George, 1991; Scale and Carney, 1991), provide some evidence that hereditary factors do play a significant role in the use and abuse of cocaine as well as other illicit drugs.

In contrast to the relative paucity of knowledge concerning the genetics of cocaine dependence, extensive scientific data are available on the neuropharmacology and toxicology of cocaine. While a number of biochemical system have been implicated in the diverse actions of cocaine on the CNS, the current favored molecular view is that the dopaminergic system plays an important, if not key role in the reinforcing actions of this drug (Koob and Bloom, 1988; Johanson and Fishman, 1989; Balster 1988).

Research on the genetics of alcoholism may provide a paradigm for similar research on cocaine dependence. Recent studies from the inventors' laboratories have shown a strong association between the less prevalent A1 allele of the $D_2$ dopamine receptor (DRD2) gene and alcoholism (Blum et al., 1990). The degree of this association was positively related to the severity of the disorder. Moreover, in a study of receptor binding characteristics, A1 allelic subjects showed a reduced number of DRD2s compared to subjects with the more prevalent A2 allele (Noble et al., 1991). In view of the involvement of the dopaminergic system in cocaine's reinforcing effects and the previously observed role of the DRD2 gene in alcoholism, the study of Example 5 was initiated on cocaine dependence. Herein is described an allelic association from the DRD2 gene with cocaine dependent subjects, and the relationship of certain DRD2 alleles with various substance use parameters, family history of substance use and other relevant variables are compared.

SUMMARY OF THE INVENTION

The present invention concerns a method of detecting a genetic potential susceptibility to compulsive disorder in a human subject. Compulsive disorder may include drug dependence, polysubstance abuse, alcoholism, severe alcoholism, a $DRD2^{In6-Ex7}$ haplotype I subtype of alcoholism, cocaine dependence, Tourette's syndrome, attention deficit disorder with hyperactivity, post-traumatic stress disorder, and the like.

The method comprises obtaining DNA from a subject and detecting in said DNA a human dopamine D2 receptor gene allele which indicates a potential susceptibility to compulsive disorder. An allele is an alteration in DNA that is correlated with the potential susceptibility to compulsive disorder. The humane dopamine D2 receptor gene allele may be an A1 allele, a B1 allele, or a $DRD2^{In6-Ex7}$ haplotype I allele, for example. The detecting method may, for example, involve RFLP or PASA. Other D2 receptor gene alleles useful this fashion may be found by further exploration of diverse endonucleases, for example.

In a preferred embodiment, the present method comprises the detection of a genetic potential susceptibility to a compulsive disease such as alcoholism by detecting the presence of a human dopamine D2 receptor gene A1 allele. The method also detects a genetic potential susceptibility to severe alcoholism by detecting the presence of a human dopamine D2 receptor gene B1 allele in a white population. The method also relates to the detection of a genetic potential susceptibility to a subtype of alcoholism named $DRD2^{In6-Ex7}$, the allele detected is a $DRD2^{In6-Ex7}$ haplotype I allele. The method also relates to the detection of genetic potential susceptibility to cocaine dependence by detecting a human dopamine D2 receptor gene A1 allele, B1 allele, or A1 and B1 alleles.

The detection of said human dopamine D2 receptor gene A1 allele comprises obtaining DNA of a subject, subjecting said DNA to digestion by TaqI restriction enzyme, separating resultant DNA fragments, hybridizing said separated DNA fragments to a labeled recombinant phage $\lambda$-$hD_2$G1 (ATCC #61354 and 61355) or a fragment thereof specifically binding a 6.6 kb A1 allele of the human dopamine D2 receptor, and determining the presence of said A1 allele of the human dopamine D2 receptor. In particular, the fragment of recombinant phage $\lambda$-$hD_2$G1 (ATCC #61354 and 61355) may be a BamHI fragment having an about 1.7-kb size.

In another preferred embodiment, the invention relates to a method of detecting a genetic potential susceptibility to severe alcoholism in a human subject, comprising obtaining the DNA from said subject and detecting in said DNA a human dopamine D2 receptor gene B1 allele, wherein said B1 allele indicates a potential susceptibility to severe alcoholism. In particular, the human subject is white.

The detection of the B1 allele comprises obtaining DNA from a subject, subjecting said DNA to digestion by TaqI restriction enzyme, separating the resultant DNA fragments, hybridizing said separated DNA fragments to a labeled recombinant phage $\lambda$-$hD_2$G2 or a fragment thereof specifically binding a 4.6 kb B1 allele of the human dopamine D2 receptor, and detecting the presence of said B1 allele of the human dopamine D2 receptor in the DNA fragments. In particular, the fragment of recombinant phage $\lambda$-$hD_2$G2 is a BamHI fragment having an about 3.7 kb size.

Another aspect of the present invention is a method of detecting a genetic potential susceptibility to a $DRD2^{In6-Ex7}$ subtype of alcoholism in a human subject. This method comprises obtaining DNA from said subject, and detecting in said DNA a human dopamine $DRD2^{In6-Ex7}$ receptor gene allele haplotype I. The presence of haplotype I indicates a potential susceptibility to a $DRD2^{In6-Ex7}$ haplotype I alcoholism subtype. The detecting of a DRD2$^{In6-Ex7}$ receptor gene allele haplotype I comprises obtaining DNA from a subject, subjecting said DNA to PCR™ amplification of specific alleles. PCR™ amplification of specific alleles includes selectively amplifying haplotype I using #3208 primer GAGTCTFCAGAGGGT (SEQ ID NO:5) and #3420 primer TGCTGTGGAGACCG (SEQ ID NO:6). The amplification products may be separated by size. Haplotype I has an about 241 base pair band.

A further aspect of the present invention is a method of detecting a genetic potential susceptibility to cocaine dependence in a human subject. This comprises obtaining DNA from a subject, and detecting in said DNA a human dopamine D2 receptor gene A1 allele. The presence of said allele indicates a potential susceptibility to cocaine ddpendence. The method also comprises detection of a B1 allele indicating the same potential susceptibility.

The present invention also provides for a kit for use in genetically detecting potential susceptibility to compulsive disorder in a human subject. The kit comprises a earlier compartmentalized to receive one or more container means in close confinement therein; a first container means including a restriction enzyme capable of cleaving a human dopamine D2 receptor gene, a second container means including a hybridization probe for detecting a human dopamine D2 receptor gene allele whose presence indicates susceptibility to compulsive disorder.

In particular, the kit would include a container holding the restriction enzyme TaqI capable of cleaving a human dopamine D2 receptor gene, and a container holding the hybridization probe for the detection of the B1 allele which is the λ-hD$_2$G1 (ATCC #61354 and 61355) or a fragment thereof having binding specificity for the A1 allele. Another kit would include the restriction enzyme TaqI, and, for the detection of the DRD2 B1 allele, the hybridization probe of λ-hD$_2$G2 or an allele-binding fragment thereof.

A further kit would include a first container means comprising PASA primers specifically binding dopamine D2 receptor alleles characterizing susceptibilitiy to a compulsive disorder; and a second container means comprising ingredients for PCR™ amplification of specific dopamine D2 receptor alleles. The PASA primers are #3208 primer GAGTCTTCAGAGGGT (SEQ ID NO:5) and #3420 primer TGCTGTGGAGACCG (SEQ ID NO:6) and the ingredients include Amplitaq® DNA polymerase for the detection of the DRD2$^{In6-Ex7}$ haplotype I allele.

The alleles described herein could be detected by other methods, for example, the RFLP's detected by Southern hybridization technology. Such alleles are also detectable by PCR™ or PASA methodology or sequence specific antibodies.

An object of the invention is to provide a safe and reliable method to detect susceptibility to compulsive disorder, alcoholism and/or other drug risk at the prenatal and postnatal level.

The above described method may also be of value in genetically detecting vulnerability toward other substance abuse patterns including, but not limited to, nicotine, narcotics and other abused drugs. In a particular embodiment, the above described method may also be used to detect a vulnerability to attention deficit disorder with hyperactivity (ADDH) in children. In a more particular embodiment, this method may be correlated to the presence of ADDH and/or to detect vulnerability to alcoholism with greater reliability as well as other genetic diseases such as Tourette Syndrome (Comings and Comings, 1987; Comings, 1987; Comings and Comings, 1990). This genetic disorder has been linked to a severe form of alcoholism possibly caused by a disinhibition of the limbic system (Comings and Comings, 1987; Comings, 1987; Comings and Comings, 1990).

BRIEF DESCRIPTION OF THE DRAWINGS

FIG. 3A shows the hybridization pattern of TaqI-digested DNA isolated from a heterozygous individual. The hybridization probe is the full-length λ-hD$_2$G1 (ATCC #61354 and 61355) which hybridizes with the 6.6 kb fragment associated with the A1 allele plus the 3.7 kb and the 2.9 kb bands associated with the A2 allele. In addition, the probe also hybridizes with two constant bands, 10.5 and 2.3 kb in length.

FIG. 3B shows the hybridization patterns of TaqI-digested DNA isolated from a nonalcoholic (homozygous for the A2 allele) and an alcoholic (heterozygous for the A1 and A2 alleles) individual. The hybridization probe is a 1.6 kb BamHI fragment isolated from λ-hD$_2$G1 (ATCC #61354 and 61355). Note that the smaller probe does not hybridize to the 2.9 and 2.3 kb TaqI fragments of the human dopamine D$_2$ receptor gene. λ-hD$_2$G1 (ATCC 61354 and 61355) is a genomic EMBL 3 phage containing approximately 18 kb of human leukocyte DNA.

FIG. 7A shows the 1.6 kb probe doublet (Doublet 1.73 kb=1.6 kb) which results from the digestion of λ-hD$_2$G1 (ATCC #61354 and 61355) with BamHI. Initially this probe was thought to consist of 1.5 kb (personal communication D. K Grandy). After sequencing the doublet was estimated as 1.73 kb. Subsequent separation of the doublet into clone 9 and clone 16 singlets, revealed, through sequencing, an actual size for the clone 9 fragment of 1.6kb.

FIG. 7B illustrates the fragments from clone 9 and 16. For purposes of this application, reference to the 1.73 kb probe is equivalent to the 1.6 kb probe. Twenty μg (ug) of the parent clone, λ-hD₂G1 (ATCC #61354 and 61355), was digested with 48 units of BamHI for two hr. at 37° C. in Buffer C (IBI), loaded onto a 0.8% agarose gel, run overnight at 23 volts, and visualized with ethidium bromide staining. The adjacent gel indicates DNA fragments of known molecular weight as standards.

FIG. 8 shows the hybridization patterns of the 1.6 kb probe after doublet separation by subcloning. The 1.6 kb fragment (doublet) was ligated by following the procedure given by Sea Plaque GTG agarose and cloned as described in Example 1. DNA from antibiotic resistant clones was digested with BamHI and separated by gel electrophoresis as in FIG. 7 to identify the presence of the 1.6 kb fragment. Other digestions of clone DNA with different endonucleases (HinfI, MspI, TaqI, BamHI, and HindIII) revealed differences in DNA patterns following separation on gel electrophoresis. In this manner, clones 9 and 16 were selected and grown. The 1.6 kb fragment from BamHI-digested DNA from clone 9 and clone 16 was radiolabeled and hybridized with TaqI-digested human genomic DNA using the same procedure as in FIG. 3 above. The genomic DNA was from two individuals, one homozygous for the $A_2$ allele, indicated here as $A_2$, and one heterozygous, A1A2, indicated as $A_1$.

Figure 9:
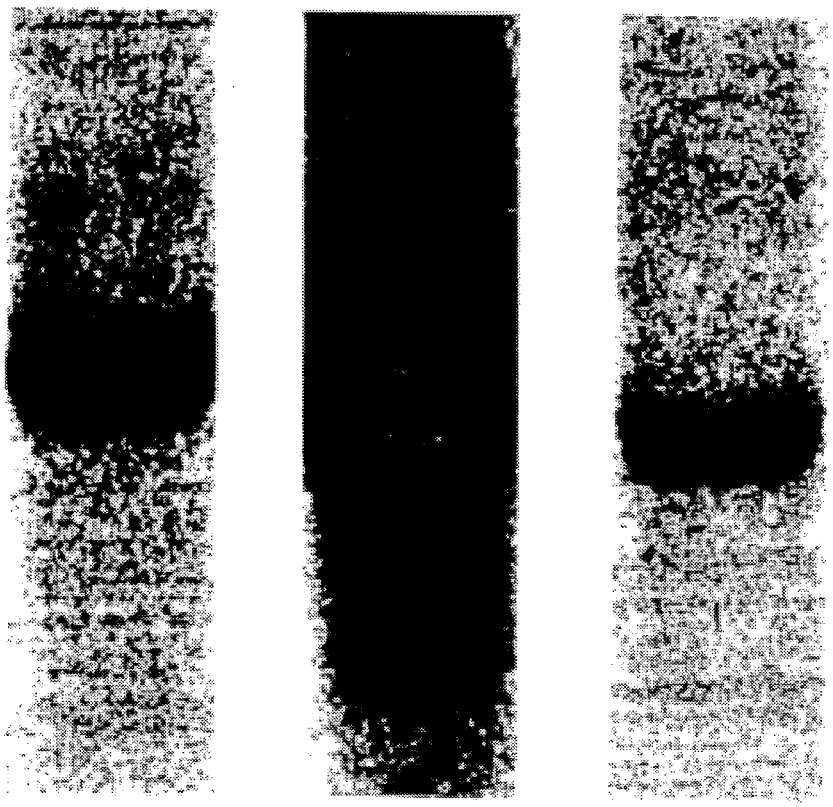

FIG. 9 shows the hybridization patterns of TaqI digested DNAs from a homozygous (B1/B1), a heterozygous (B1/B2) and a homozygous (B2/B2) individual using a BamHI digested λ-hD₂G2 insert as a probe. The identifying band in individuals carrying the B1 allele is the 4.6-kb band (B1/B1 and B1/B2). The identifying band in individuals carrying the B2 allele is the 4.1 kb band (B1/B2 and B2/B2). Note that the individual homozygous for B1 has only the 4.6 kb band and that the individual homozygous for the B2 allele has only the 4.1 kb band.

Figure 10B:
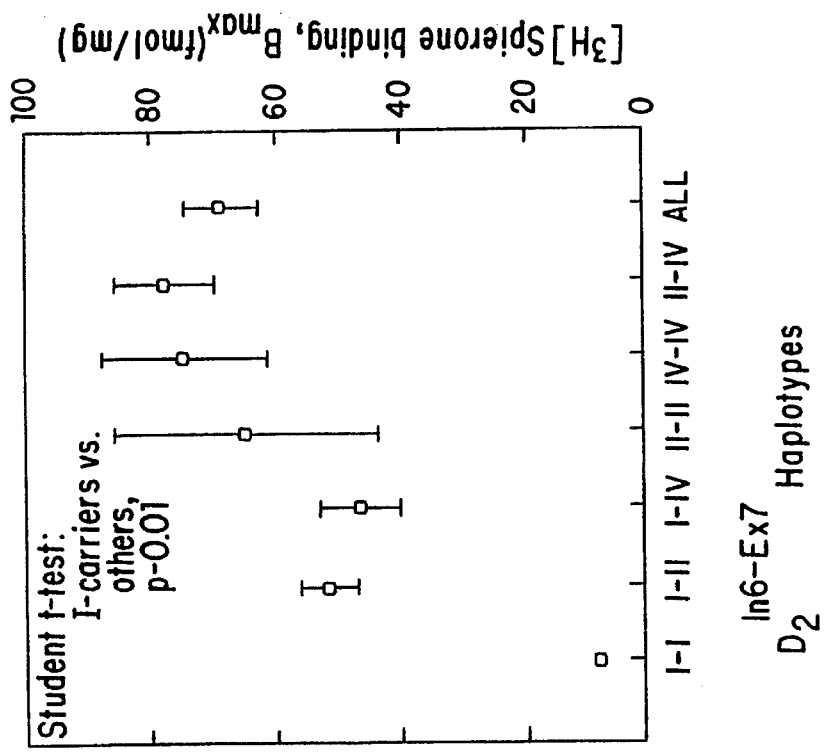
Figure 10A:
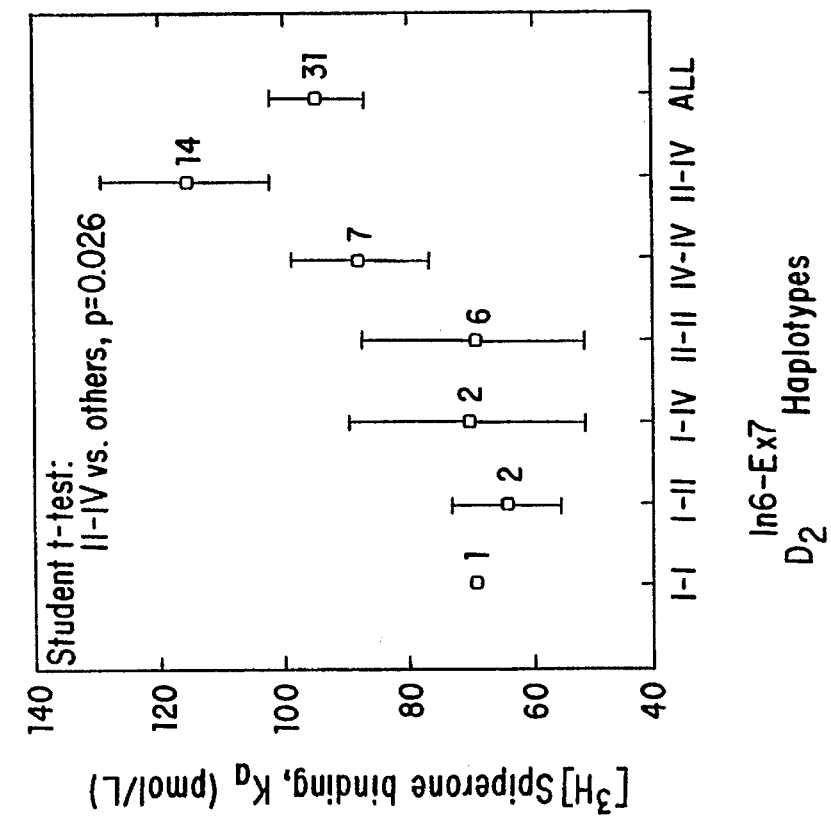

FIG. 10 shows the relationship between dopamine receptor $D2^{In6-Ex7}$ haplotype status and spiperone $B_{max}$ and $K_d$ binding properties in caudate autopsy samples.

Figure 11:
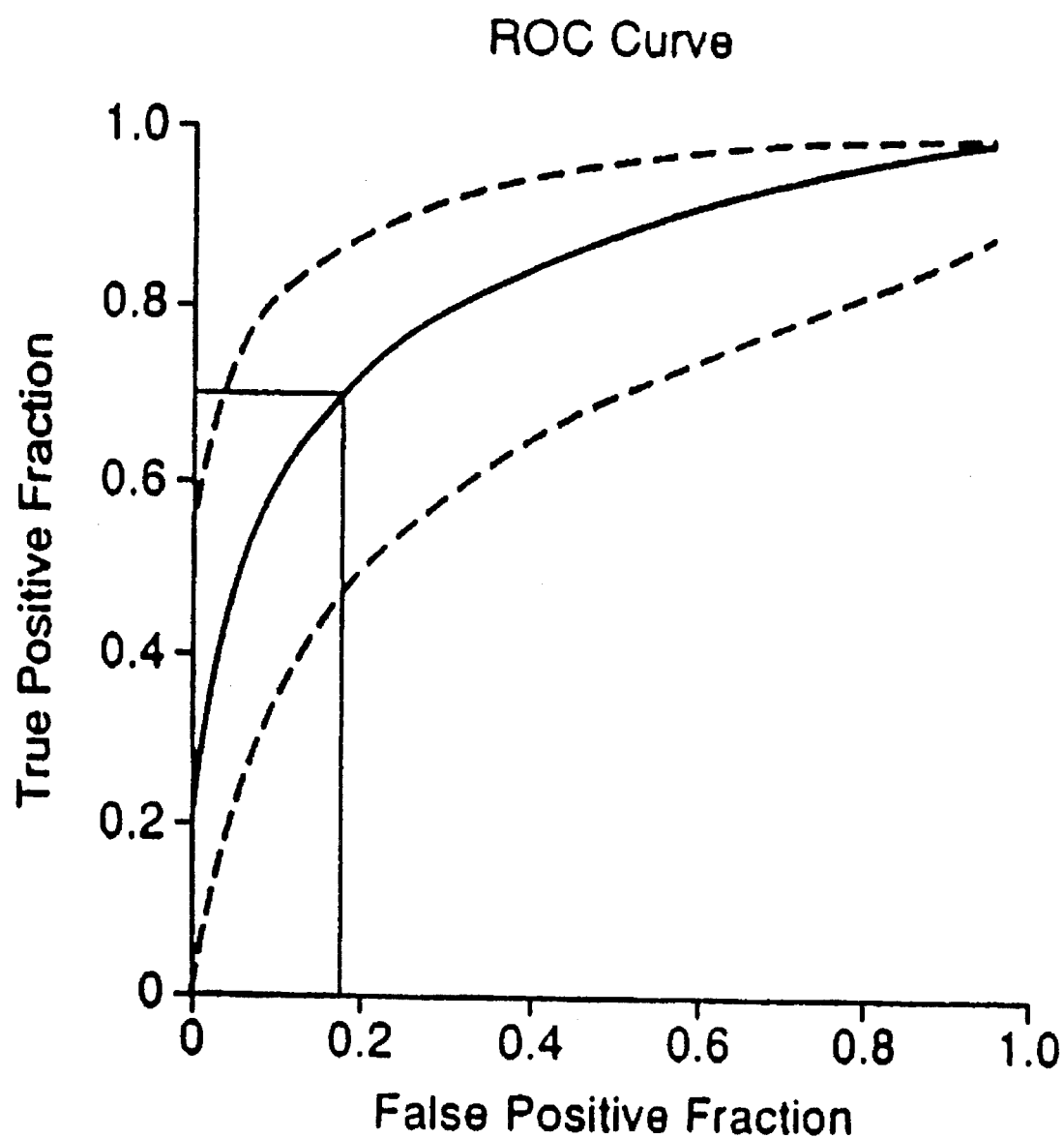

FIG. 11 shows the receiver-operating characteristic (ROC) curve. The model of the performance curve is shown as a solid curved line, with area under the curve= 0.826±0.057 (SD). The broken curves represent the upper and lower bounds for the 95% confidence limits for the calculated ROC curve. At the optimal probability cut-point, a true-positive fraction of 0.759 (y axis) and a false-positive fraction of 0.136 (x axis) are obtained.

Figure 12:
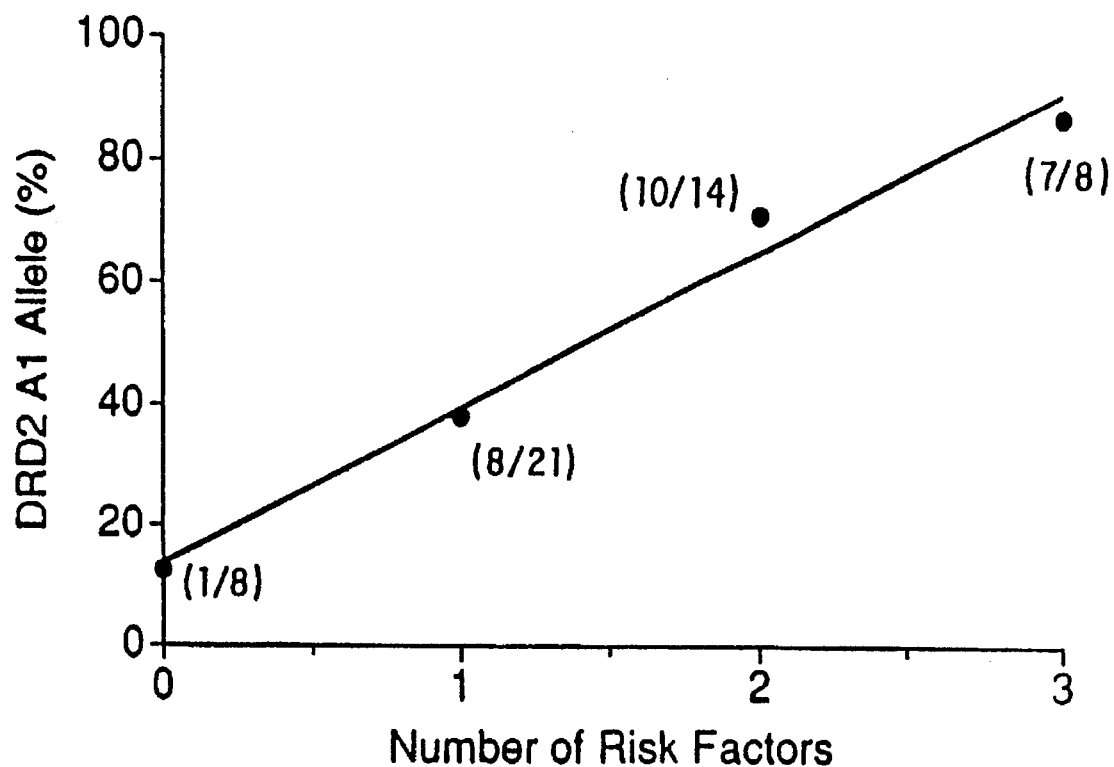

FIG. 12 shows the DRD2 A1 allele as a function of number of risk factors in cocaine dependent subjects. The risk factors include: family history of alcoholism (presence of at least one alcoholic parent) and the values above 50% level for measures of number of early deviant behaviors and potency of cocaine used (i.v., free base and "crack"). Linear trend analysis showed that risk factors are positively and significantly associated with the prevalence of DRD2 A1 allele ($\chi^2$=12.74, df=1, P=0.0005).

Figure 13:
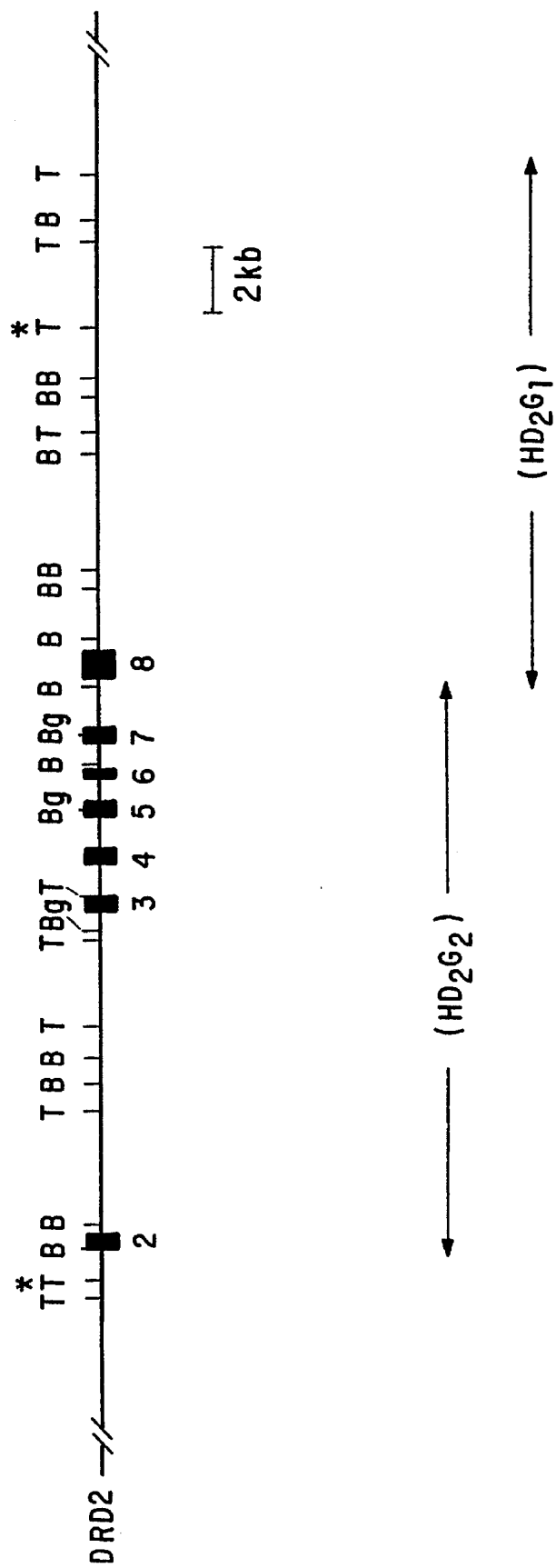

FIG. 13 shows the partial map of the human dopamine D2 receptor gene locus (DRD2). A partial restriction map is presented for the enzymes BamHI(B), BglII (Bg), and TaqI(T). Polymorphic TaqI sites are indicated by asterisks. The regions corresponding to genomic phage λ-hD₂G1 (ATCC #61354 and 61355) and λ-hD₂G2 are indicated. This figure is from Hauge et al., 1991.

Figure 14:
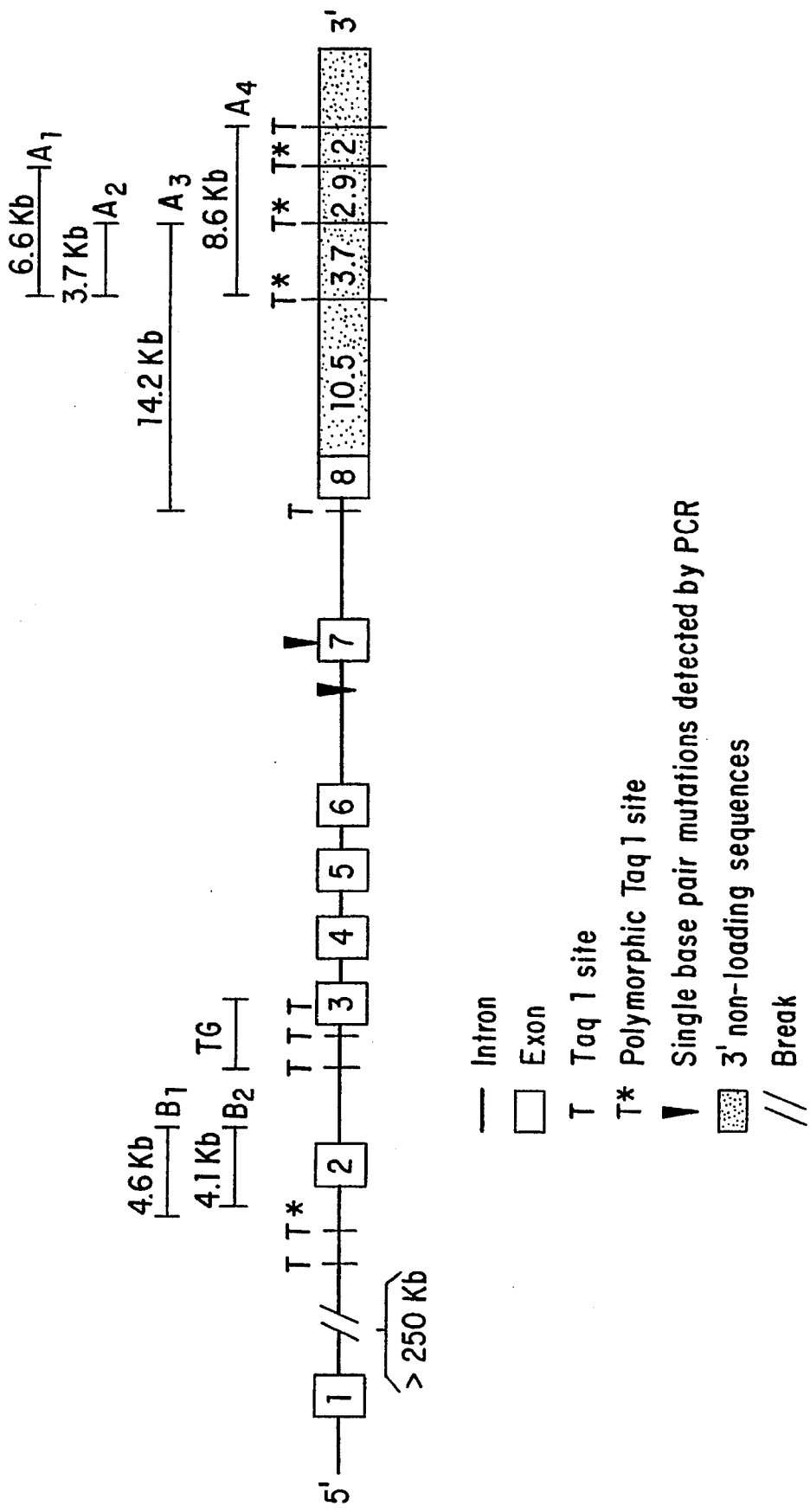

FIG. 14 is a more detailed gene map of the human dopamine D2 receptor gene showing introns, exons, TaqI sites, polymorphic loci, single base pair mutations detected by PCR™ and 3' non-coding sequences. The figure is a composite from Amit and Brown, 1982, Example 3; Grandy et al., 1989, Example 2; and Maslen, et al., 1988, Example 5.

| LIST OF ABBREVIATIONS | |
|---|---|
| A1A2 | heterozygous for the A1 and A2 allele |
| A2A2 | homozygous for the A2 allele |
| $B_{max}$ | Number of receptors |
| DA | dopamine |
| dCTP | deoxycytosine triphosphate |
| D₂DR or DRD2 = | Dopamine D₂ Receptor |
| DSM-IV-R | (criteria) diagnostic standard manual |
| ETOH | Ethanol |
| fmol | femtomole ($10^{-15}$ mole) |
| IBI | International Biotechnologies, Inc. |
| kb = Kb | Kilobase or Kilobit |
| $K_d$ | Dissociation constant |
| lambda-hD₂G1 = | λ-hD₂G1 18 kb probe used to detect A1 allele. |
| P | Probability |
| PASA | PCR ™ amplification of specific alleles |
| PIC | polymorphic information content - a measure of the probability that informative alleles are segregating in a family |
| pM | picomolar ($10^{-12}$M) |
| RFLP | Restriction Fragment Length Polymorphism |
| SSC | saline solution containing sodium citrate |
| SSDNA | Salmon sperm DNA |
| TE | Tris-EDTA Buffer |
| ug = μg | microgram |

DESCRIPTION OF THE PREFERRED EMBODIMENT

The present invention relates to a pioneering discovery of allelic association with compulsive disease and provides a method for detecting on a molecular basis a genetic potential susceptibility to compulsive disorders such as alcoholism. In particular, the detection of certain alleles associated with the genes encoding the human dopamine D2 receptor protein is an indication of a genetic potential susceptibility to compulsive disorder.

The data presented in these examples illustrate utility of the present invention and are summarized in Table 1.

TABLE 1

Allelic Association with Substance Abuse Summarized from Examples 1–4.

| Substance Abuse | Allele | Abusers | % Prevalence Controls |
|---|---|---|---|
| Alcoholism | DRD2 A1 | 69 | 20 |
| Severe alcoholism | DRD2 B1 | 47 | 17 |
| DRD2$^{In6-Ex7}$ subtye of alcoholism | DRD2$^{In6-Ex7}$ haplotype I | 39.4 | 16.1 |
| Cocaine Dependence | DRD2 A1 | 51 | 18.5 |
| Cocaine Dependence | DRD2 B1 | 38.5 | 13 |

Example 1 describes the analysis of preserved brain DNA from 70 deceased individuals, half of whom died of complications of alcoholism. Fully 69% of these known alcoholics possessed the A1 allele of the DRD2 gene whereas only 20% of nonalcoholic controls were positive for this allele. The same analysis was carded out on DNA samples from a set of living subjects. In a sample size of 49 alcoholic individuals, 63% were positive for the A1 DRD2 allele whereas 22% of the nonalcoholic individuals carried this allele.

Example 2 examines, in Caucasian subjects, the association of the B1 allele of the DRD2 gene with a severe as opposed to a less severe subtype of alcoholism. "Less severe" relates to subjects with the presence or absence of dependency symptoms and the absence of medical complications. "Severe" alcoholism relates to subjects displaying dependency symptoms as well as medical complications. The B1 allele is present in 47% of severe alcoholics (sample size of 49) compared to 17% of less severe alcoholics (sample size of 36).

Example 3 cites the association of the haplotype I of the $DRD2^{In6-Ex7}$ allele with alcoholism.

Example 4 describes the association of cocaine dependence with the presence of the A1 and/or B1 alleles of the DRD2 receptor gene. Of 53 cocaine dependent white subjects, 51% possessed the A1 allele compared to 18.5% of a control group (sample size=54). These data are independent of comorbid alcohol dependence. The B1 allele was present in 38.5% of the cocaine dependent subjects and in 13% of the nonsubstance abusing controls.

In all of these examples, the particular allele is found more frequently in those subjects demonstrating compulsive disorder as compared to controls. The detection of the particular allele, therefore, is an indicator of a genetic potential susceptibility to compulsive disorder. As other alleles for biogenic amine receptors are found associated with compulsive disorders, they too may be used to indicate potential susceptibility.

The following examples are presented to describe preferred embodiments and utilities of the present invention, but should not be construed as limiting the subsequent claims unless otherwise so specified.

EXAMPLE 1

ASSOCIATION OF THE $D_2$ DOPAMINE RECEPTOR TaqI A1 ALLELE WITH ALCOHOLISM

The present example demonstrates an allelic association, namely of the dopamine $D_2$ receptor gene, with alcoholism. DNA, from matched alcoholic and nonalcoholic brain samples, was digested with restriction endonucleases and probed with the human $D_2$ receptor gene ($\lambda$-hD$_2$G1)(ATCC #61354 and 61355). The presence of the A1 (6.6 kb band) allele of the dopamine ($D_2$) receptor (also abbreviated D2DR) gene correctly identifies 77% of alcoholics, and its absence identifies 72% of nonalcoholics. The polymorphic pattern of this receptor gene suggests that the abnormality in at least one form of alcoholism is located on the q22–q23 region of chromosome 11 with a co-dominant Mendelian mode of inheritance. The allelic association of the dopamine ($D_2$) receptor gene with alcoholism has a high predictive value in the classification of one probable alcoholic subtype. This subtype may represent a virulent form of alcoholism.

Tissues from 35 alcoholic and 35 nonalcoholic subjects were obtained from the National Neurological Research Bank at the VA Medical Center, Wadsworth, Los Angeles. Frontal grey cortex and caudate nucleus were removed from the brain at autopsy by a neuropathologist and immediately frozen at −70° C. until used. The ages (average±SEM) of the alcoholics and nonalcoholics, respectively, were 50.4±2.3 years and 53.2±2.6 years. The racial distribution of alcoholics included 21 whites and 12 blacks, and there were 24 white and 9 black nonalcoholics. The sex distribution of alcoholics included 30 males and 3 females, and there were 29 male and 4 female nonalcoholics. The autolysis times (average±SEM) of the alcoholics and nonalcoholics, brain samples were, respectively, 23.0±1.5 hr. and 22.6±1.7 hr. Alcoholic (Alcohol Dependence and Alcohol Abuse, using DSM-III-R criteria [American Psychiatric Association, 1987]) and nonalcoholic diagnoses were made independently by two trained psychiatrists, through examination of medical and autopsy records, interviews of treatment center personnel and relatives and alcohol consumption data. There was a 100% concordance in diagnosing alcoholic and nonalcoholic subjects between these two assessments. Examination of medical records and/or analysis of body fluids at autopsy did not reveal any of the subjects to have used neuroleptics. The cause of death included: accidents, gunshot wounds, myocardial infarction, heart failure, cancer, gastrointestinal bleeding, suicide, and pneumonia. Informed consent was obtained from next of kin to carry out the present study.

These seventy frozen brain samples were thawed and processed for high molecular weight genomic DNA. The tissue was homogenized in 0.25M sucrose and a nuclear pellet prepared. Next the pellets were incubated at 37° C. for three hrs in 0.05% SDS and proteinase K and the DNA was extracted with phenol, followed by extraction with chloroform:isoamyl alcohol. The DNA was then spooled out, washed with ethanol, and stored in 10 mM Tris-1 mM EDTA pH 8.0 at 4° C. When all the DNAs were isolated, aliquots (20 ug DNA) were digested separately with four different restriction endonucleases (i.e. TaqI, MspI, EcoRI and PstI) at approximately two units enzyme/ug DNA, run on agarose gels, Southern-transferred to nylon membranes, and hybridized with different DNA probes using standard methods (Maniatis et al., 1982). In the present example, the DNA samples, after digestion with the four restriction enzymes, were hybridized with a number of probes involved with either ethanol metabolism or neurotransmitter regulation of reward, including the human dopamine $D_2$ receptor gene ($\lambda$-hD$_2$G1) (ATCC #61354 and 61355) to determine polymorphism. This procedure used to generate the human $D_2$ receptor gene ($\lambda$-hD$_2$G1) (ATCC #61354 and 61355) is as follows: A human genomic library was screened with the rat dopamine $D_2$ receptor cDNA. The human genomic library (Clonetech) in EMBL3 was prepared from normal male leukocyte DNA and screened with a nick-translated probe containing portions of the cDNA for the coding region of the rat $D_2$ receptor. One clone, $\lambda$-hD$_2$G1 (ATCC #61354 and 61355), with an 18 kb insert was identified and characterized. This clone was found to contain the entire 3' coding exon, the polyadenylation signal, and approximately 16.4 kb of noncoding 3' sequence. Twenty μg of the parent clone ($\lambda$-hD$_2$G1) (ATCC #61354 and 61355) was digested with 48 units of BamHI for two hrs at 37° C. in Buffer C (IBI), loaded on 1% agarose gel (Sea Plaque™), and run overnight at 23 volts. When digested under these conditions, several fragments were generated, including a 1.6 kb fragment and a second band of 1.5 kb, made up of two 1.5 kb fragments. The 1.5 kb band was cut, heated to 68° C., diluted by a factor of three with TE buffer, and stored at 4° C. The diluted gel was placed in boiling water for three min and then incubated for ten min at 37° C. A 25 ul aliquot was then removed and labelled to a specific activity of $1\times10^9$ cpm/μg with [$^{32}$P]-dCTP according to the oligolabeling kit (Pharmacia). The 50 ul (microliter) incubation mixture was then chromatographed through a G-50 SEPHADEX column and the eluant used for hybridization. The TaqI digested DNAs were then transferred to Nytran membranes and hybridized with the labelled insert in 50% formamide, 5X SSC, 1 Denhart's, 20 mM $NaH_2PO_4$, 200 μg/ml of SSDNA, 0.1% SDS, 10% dextran sulfate, 0.25% dry milk, and incubated overnight at 42° C. The filters were then washed 2× with SSC, 0.1% SDS at 55° C., and radioautographed overnight. The only endonuclease to show polymorphism with λ-$hD_2$G1 (ATCC #61354 and 61355) was TaqI (vide infra).

In previous studies (Grandy et al., 1989), where the λ-$hD_2$G1 (ATCC #61354 and 61355) was used to probe digests of human genomic DNA, it was found that only TaqI, but not digests from 30 other endonucleases, revealed a frequent two allele RFLP. Allele A1=6.6 kb and allele A2=3.7±2.9 kb with constant bands at 10.5 and 2.3 kb. Allele frequencies were measured in 43 unrelated Caucasians and calculated to have a frequency of A1=0.24, A2=0.76. Co-dominant Mendelian inheritance was observed in four informative families with a total of 39 children. Additionally, the human dopamine (D2) receptor gene was mapped on the q22-q23 region of chromosome 11 (Grandy et al., 1989).

Figure 1:
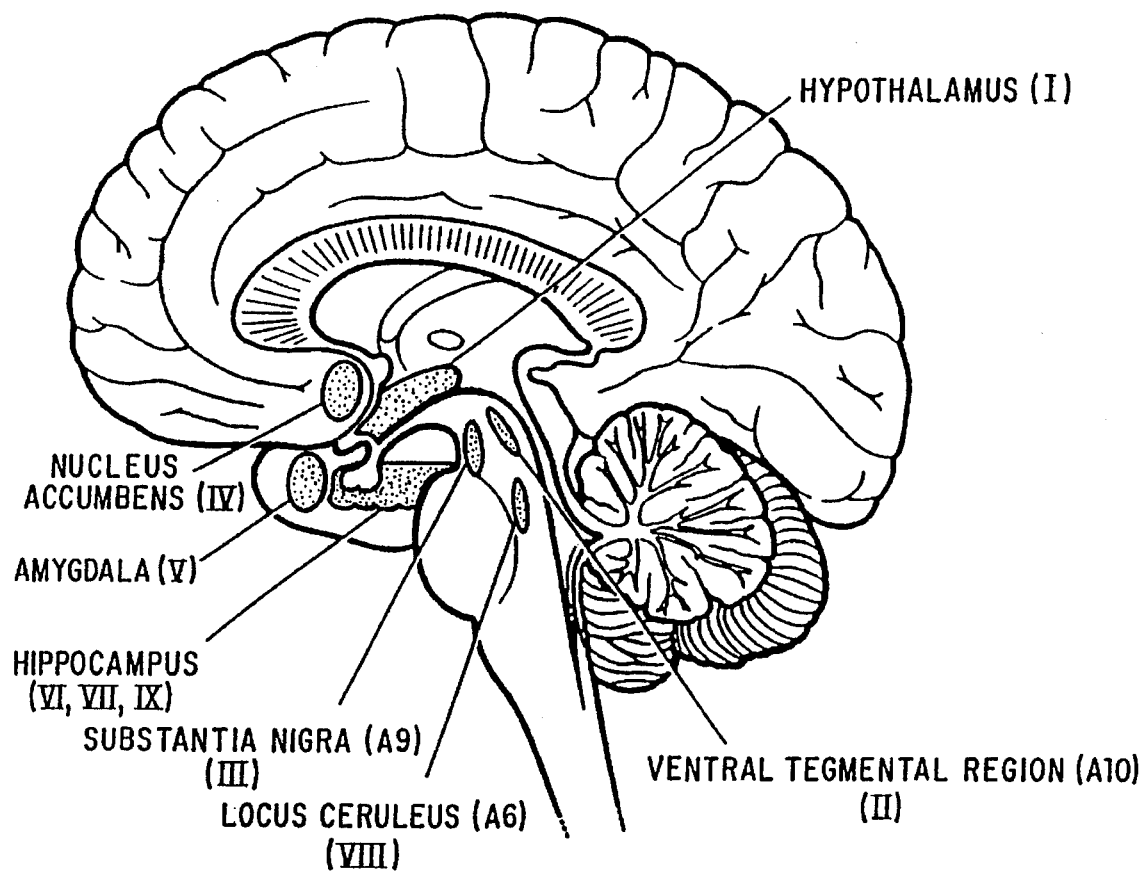
FIG. 1. Simplified schematic of the brain's meso-limbic system, where the major reward activity takes place. Sites are indicated by roman numerals.
Figure 2:
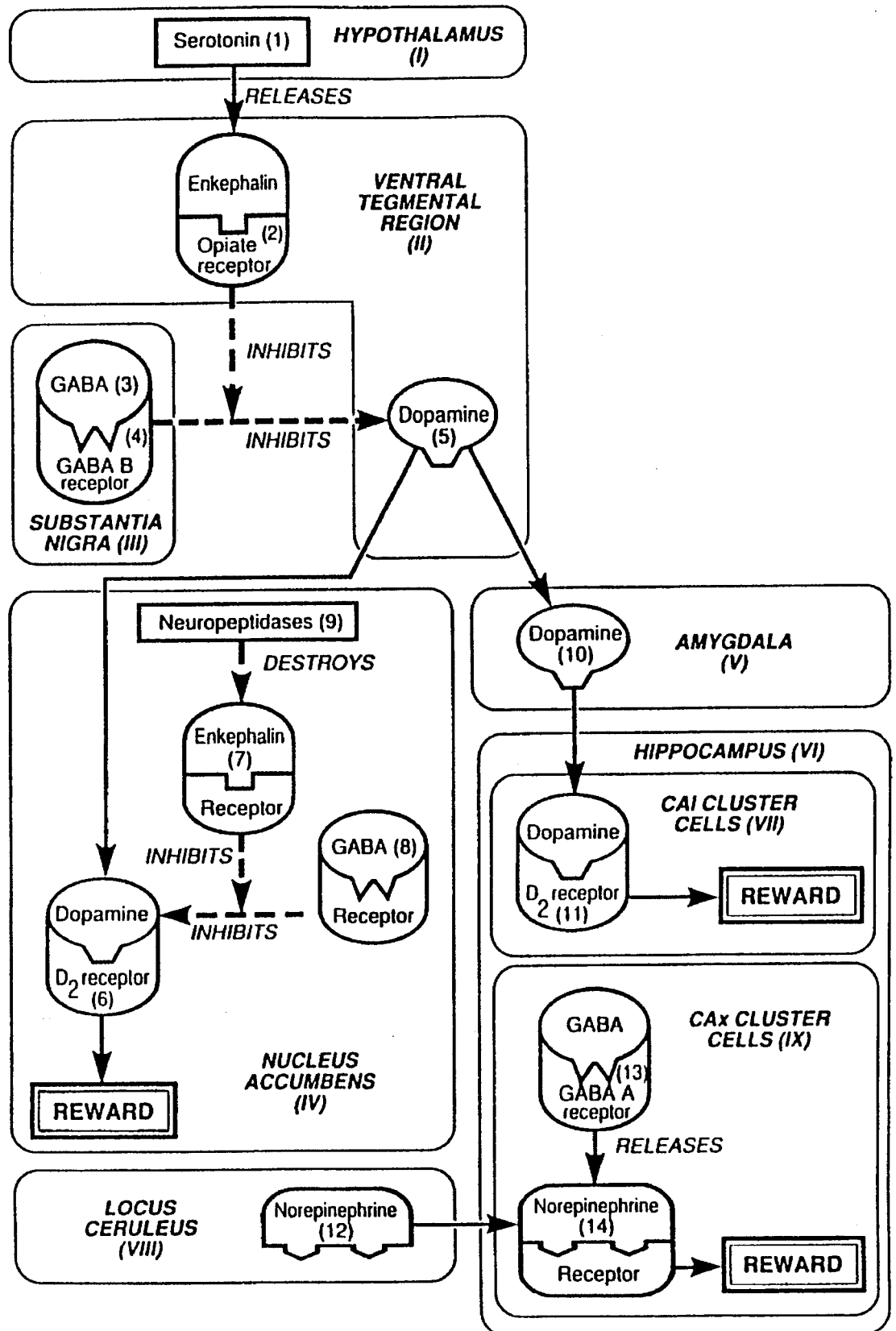
FIG. 2. Detail from Reward Cascade Model. A schematic showing how neurotransmitters, enzymes, and receptors may interact to produce craving for alcohol. Individual elements of the "reward cascade model" are indicated by arabic numerals, keyed to roman numerals from FIG. 1.
Figure 3C:
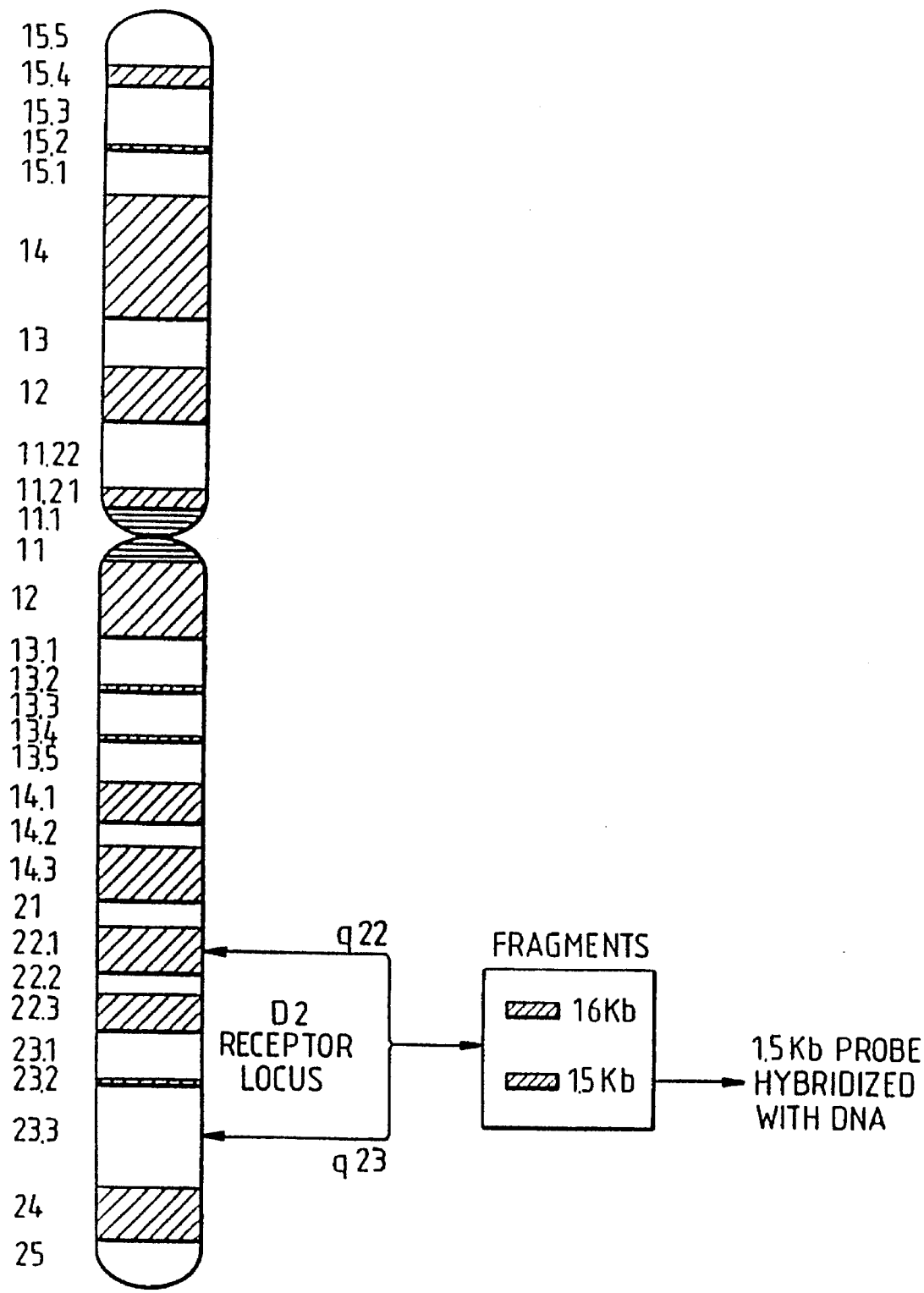
FIG. 3C schematically shows the production of the 1.7 kb probe for the dopamine D$_2$ receptor gene obtained from chromosome 11.

FIG. 3A, FIG. 3B, and FIG. 3C illustrate the polymorphic pattern of the human dopamine (D2) receptor gene. FIG. 3A depicts the polymorphic allclio pattern for the λ-$hD^2G1$ (ATCC #61354 and 61355) gene clone. FIG. 3B shows the allelic pattern using a BamHI 1.5 kb subclone which reduced overall background and still was informative as to the presence of alleles A1 and A2. However, the smaller probe did not hybridize to the 2.9 and 2.3 kb TaqI fragments of the human dopamine (D2) gene. For illustrative purposes only, the polymorphic patterns are labelled according to their highly significant allelic association with either alcoholics (A1 allele) or nonalcoholics (the absence of A1 allele), respectively labelled A1/A2 and A2/A2. The schematic production of the 1.5 kb ("1.5 kb" illustrated here later was determined to actually be "1.7 kb") subclone probe from chromosome 11 is shown in FIG. 3C.

Table 2 illustrates the polymorphic pauem of the dopamine $D_2$ receptor gene with DNA obtained from alcoholic and nonalcoholic subjects following three independent hybridizations. The A1 allele is associated with 24 of 35 (69%) known alcoholics, but it associated with only 7 of 35 (20%) nonalcoholics. In contrast, the absence of the A1 allele is associated with 28 out of 35 (80%) of nonalcoholics and with only 11 of 35 (31%) alcoholics. The proportion of the presence of the A1 allele to the absence of this allele is significantly different in alcoholics as compared to nonalcoholics (Yates $\chi^2$ [corrected for continuity]=14.8, df=1, P<0.001).

TABLE 2

Polymorphic Pattern of the 1.5 kb Fragment (λ-$hD_2$G1) of the Dopamine $D_2$ Receptor Gene in Nonalcoholic and Alcoholic Brain Tissue

| DNA Type | Absence of A1 Allele | Presence of A1 Allele[1] |
|---|---|---|
| Control (n = 35) | 28(80.0)[2] | 7(20.0) |
| Alcoholic (n = 35) | 11(31.4) | 24(68.6) |

[1] A1 allele = 6.6 kb
[2] Values in parenthesis represent percent of nonalcoholics or Alcoholics showing absence of the A1 allele. The proportion of the presence of the A1 allele to the absence of the allele is significantly different in alcoholics compared to nonalcoholics (Yates $\chi^2$ [corrected for continuity] = 14.8, df = 1, P < .0001).

The race of subject populations is an important determinant in allelic patterns. Recently, Kidd et al., reported that at some loci, alleles that are infrequent in Caucasians are common in other populations. As the present brains were derived from both Caucasians and Blacks, the allelic frequency of the dopamine $D_2$ receptor gene was analyzed in these two racial groups.

Table 3 illustrates the Polymorphic Pattern of the Dopamine $D_2$ Receptor Gene with DNA obtained from alcoholic and non-alcoholic Caucasians and Blacks following three independent hybridizations.

The A1 allele is found to be associated with 14 of 22 (64%) Caucasian alcoholics, but it associated with only 4 of 24 (17%) Caucasian nonalcoholics (Maslen et al., 1988). The proportion of the presence of the A1 allele to the absence of the allele in Caucasian alcoholics compared to Caucasian nonalcoholics is highly significant (Yates $\chi^2$=8.75, df=1, P=0.003). In Blacks, the A1 allele is associated with 10 of 13 (77%) alcoholics, but it associated with only 3 of 11 (27%) nonalcoholics. The proportion of the presence of the A1 allele to the absence of this allele is also significantly different in Black alcoholics compared to Black nonalcoholics (Yates $\chi^2$=5.92, df=1, P=0.015). Thus, in the present sample, the results favor the view that A1 allelic association is based on whether or not an individual is an alcoholic, rather than the individual's racial background.

To determine the relationship between alcoholism and the A1 allele controlling for race, the Mantel-Hazenzel test was used. This test evaluates the relationship between two variables, while controlling for a third. Since $\chi^2$=14.20 with P<0.001, there is a highly significant association between alcoholism and the A1 allele, even after controlling for race.

In the present example, this test also suggested that the odds ratio of finding the A1 allele in alcoholics is 8.8 times as large as that for nonalcoholics.

TABLE 3

Polymorphic Pattern of the Dopamine $D_2$ Receptor Gene (λ-$hD_2$G1) in Brain Tissue of Nonalcoholics and Alcoholics

| DNA Source | Absence of A1 Allele | Presence of A1 Allele[3] |
|---|---|---|
| Nonalcoholic (n = 35) | 28(80%)[4] | 7(20%) |
| Alcoholic (n = 35) | 11 (31%) | 24(69%) |
| Nonalcoholic Caucasians (n = 24) | 20 (83%) | 4(17%) |
| Alcoholic Caucasians (n = 11) | 8 (36%) | 14(64%) |
| Nonalcoholic Blacks (n = 11) | 8 (73%) | 3(27%) |
| Alcoholic Blacks (n = 13) | 3 (23%) | 10(77%) |

[3] A1 allele = 6.6 kb.
[4] Values in parentheses represent percent of nonalcoholics or alcoholics showing absence or presence of the A1 allele.

Figure 4:
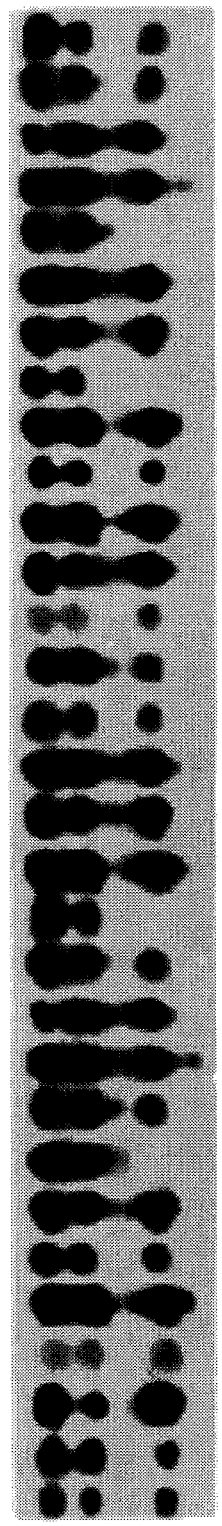
FIG. 4 shows a Southern blot analysis of human DNA from brain tissue grouped according to presence of A1 allele (6.6 kb band) of the human dopamine D$_2$ receptor (DRD2) gene. Predictive value of our sample size in correctly identifying alcoholics is 77% ($\chi^2$=9.32, DF=1, P=0.002). Note that the A2 allele (band 3.7 kb) is missing from samples 8, 13, 24, 27, and indicating that these DNAs are homozygous for the A1 allele.
Figure 5:
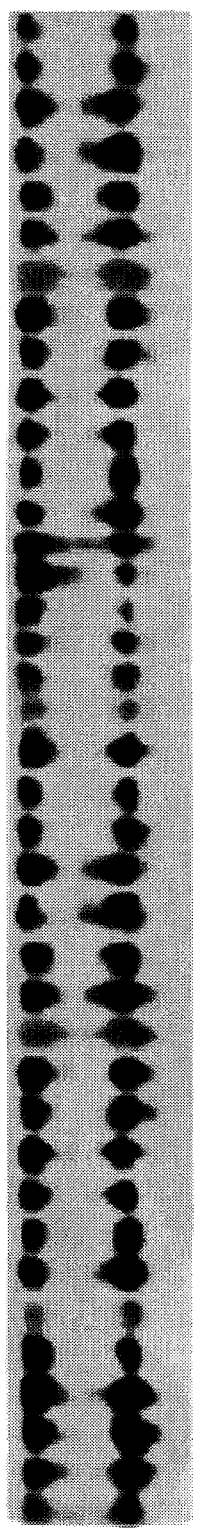
FIG. 5 shows a Southern blot analysis of human DNA from brain tissue grouped according to absence of A1 allele of the human dopamine D$_2$ receptor gene. Predictive value in correctly identifying nonalcoholics is 72% ($\chi^2$=7.41, DF=1, P=0.002).
Figure 6A:
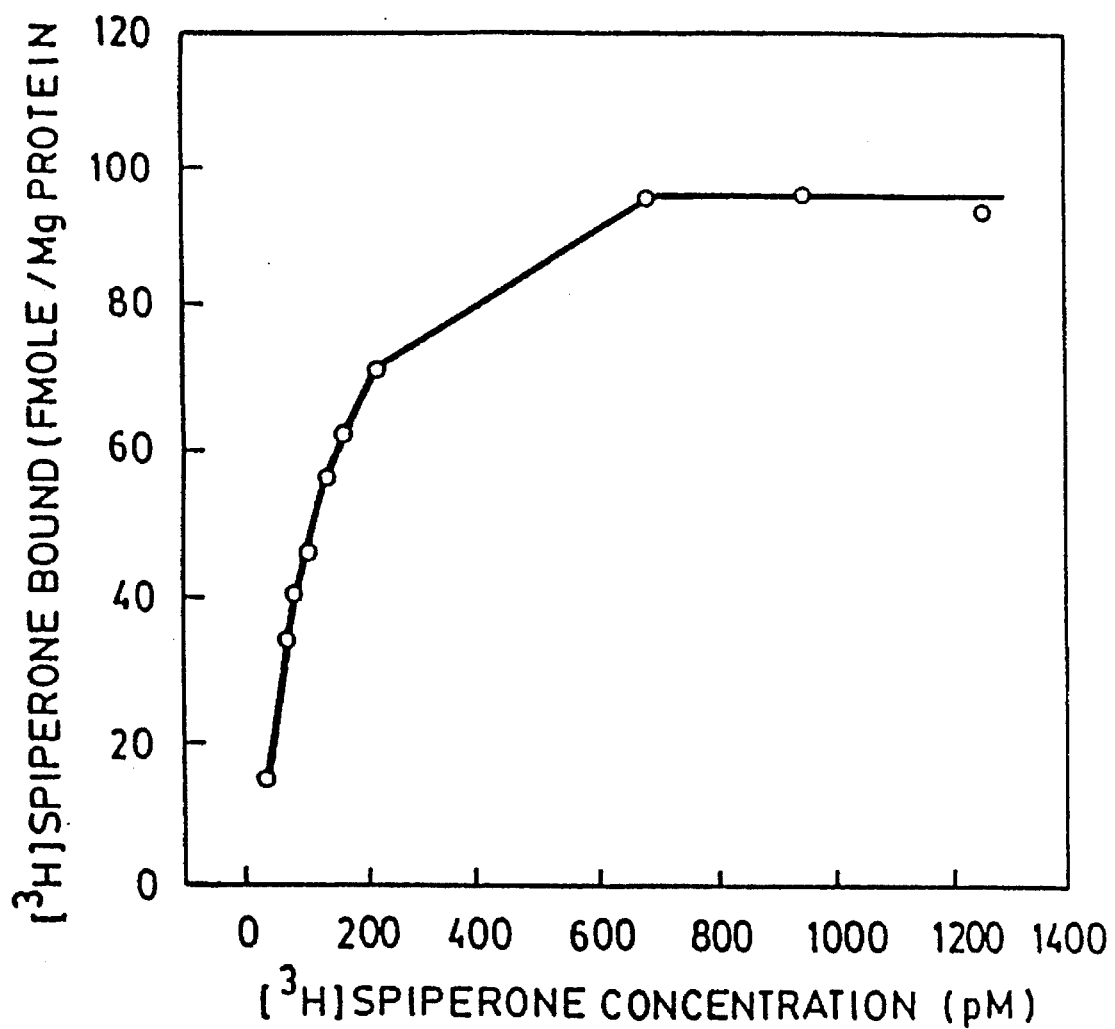
FIG. 6A shows a saturation curve of [$^3$H]spiperone binding to D2DR in caudates of a nonalcoholic subject homozygous for the A$_2$ allele (A2A2).
Figure 6B:
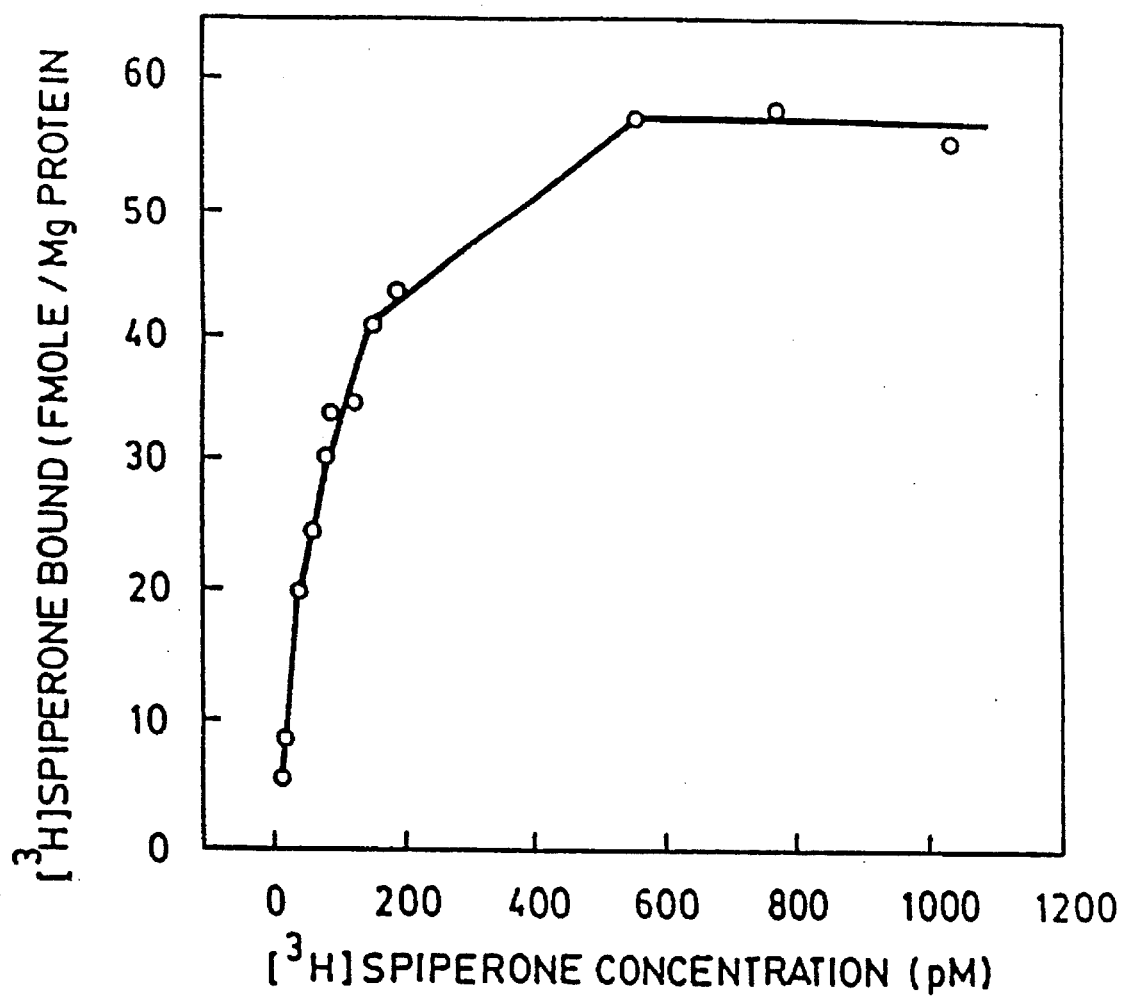
FIG. 6B shows a nonalcoholic subject heterozygous for A1 and A2 (A1A2). Data points are means of duplicate determinations. Details for the binding studies are given in Example 1.
Figure 6C:
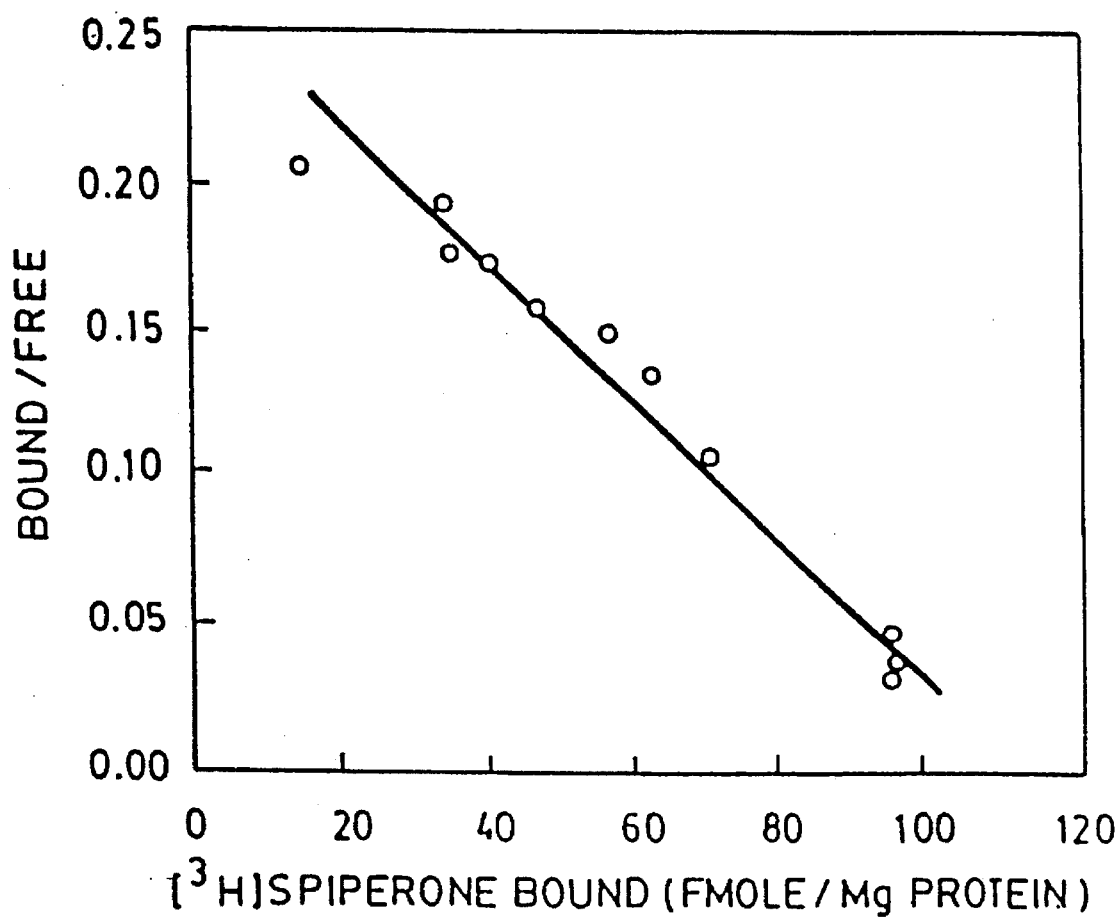
FIG. 6C and FIG. 6D show the Scatchard analysis of [$^3$H]spiperone binding for the data from FIG. 6A and FIG. 6B, respectively.
Figure 6D:
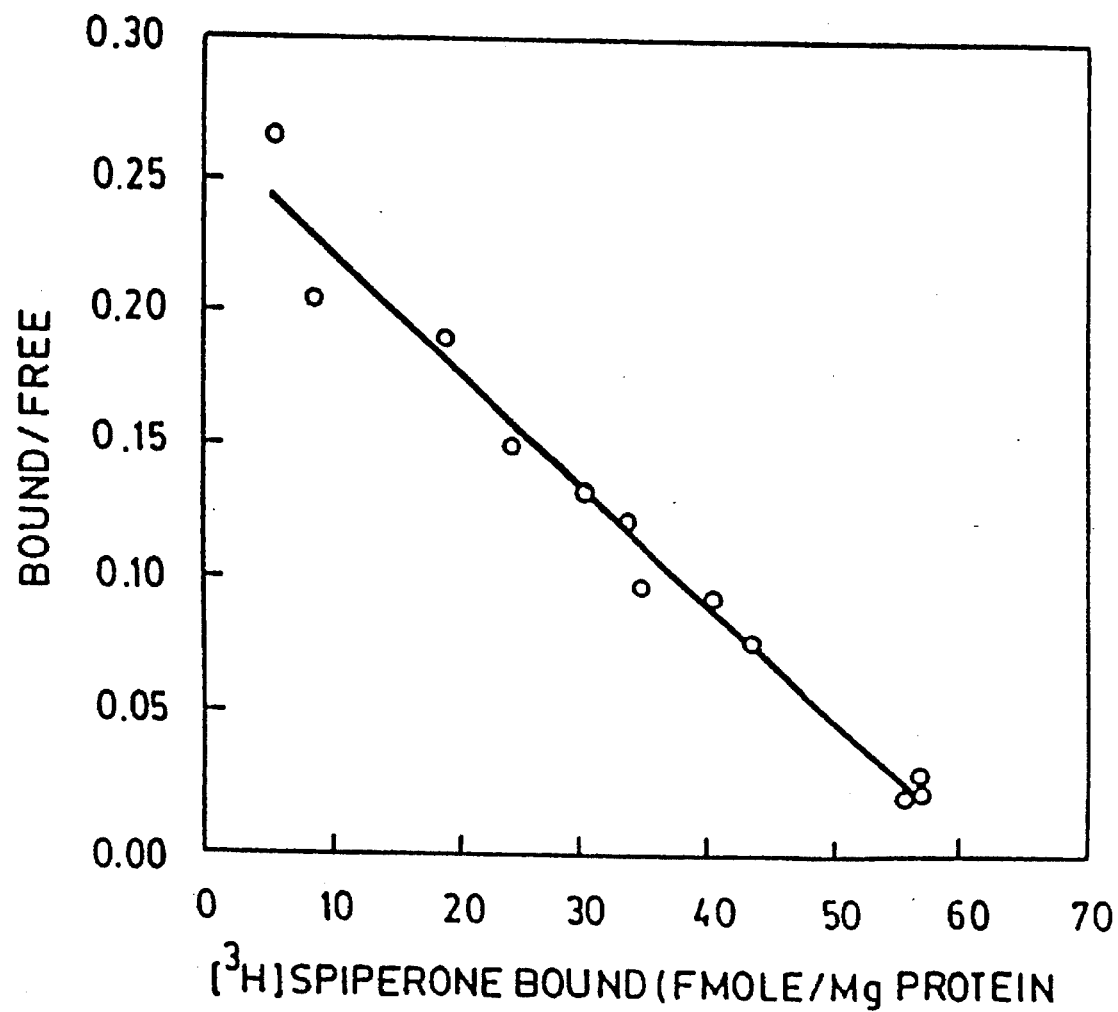

FIG. 4 and FIG. 5 show the samples grouped according to whether or not the A1 allele was present. This grouping allowed a classification of samples based on their unique allelic association with alcoholism. FIG. 4 represents 31 brain samples which possess the A1 allele (6.6). Twenty-four out of 31 DNAs that had the A1 allele were from alcoholics. This suggests, that in our sample, the predictive value of this test in correctly identifying alcoholics is 77%. FIG. 5 represents 39 brain samples which did not possess the A1 allele. Since 28 out of 39 samples did not have the A1 allele and were from nonalcoholics, this suggests that the predictive value of this test in correctly identifying nonalcoholics is 72%.

To evaluate the hypothesis that the presence or absence of the A1 allele was distributed between the alcoholic or nonalcoholic groups at other than equal probabilities, a single sample Chi-square analysis with assigned expected value of 0.50 was used. When this expected value was assigned, Chi-square analysis revealed no significant difference from the expected probability for the A1 allele in nonalcoholics ($\chi2=0.47$, df-1, P=0.50). In contrast, observed frequencies were significantly different from the expected probability of 0.25 for the A1 allele in alcoholics ($\chi^2=35.4$, df=1, P<0.001).

Of the total alleles in the present sample, the frequency of the A1 allele was 25% and that for the A2 allele was 75%. In the samples of nonalcoholics, A1 and A2 allelic frequencies were 13% and 87% respectively. The allelic frequencies in the samples of alcoholics were: A1=37% and A2=63%. The frequency of the A1 allele in samples of nonalcoholics and alcoholics were significantly different (Yates $\chi^2=9.75$, df=1, P=0.002).

To determine ability to correctly classify the alcoholic or nonalcoholic in this sample, according to the presence or absence of the A1 allele distributed between the two groups at a better than chance probability, a Chi-square analysis with assigned expected value of 0.50 was used. Observed values were significantly different from expected probability for the A1 allele ($\chi^2=9.32$, df=1, P=0.002) and for the absence of the A1 allele ($\chi^2=9.26$, df=1, P=0.002). These findings, taken together, suggest a strong allelic association of the dopamine $D_2$ receptor gene with alcoholism.

To determine the association of other putative genes with alcoholism, a number of additional candidate probes were used. Unlike $\lambda$-hD$_2$G1 (ATCC #61354 and 61355), none of these probes revealed a polymorphic pattern of association with alcoholism.

Nuclear DNA was isolated from the matched brain samples as previously described for $\lambda$-hD$_2$G1 (ATCC #61354 and 61355) probe. Twenty micrograms of DNA was digested with one of the four restriction endonucleases. The resulting DNA fragments were separated according to size by electrophoresis in 1% agarose gel, transferred to nitrocellulose membranes, fixed, and hybridized with phosphorus $^{32}$P-labelled probes. Washing of filters and autoradiography were carried out as described previously in this paper. A number of probes were employed, including alcohol dehydrogenase (pADH/3), protein kinase-C (phPKC), carboxypeptidase-A (CPA), pro-enkephalin (pHPE9), tryptophan hydroxylase (TPH479), tyrosine hydroxylase (BTH$_4$), monoamine oxidase B (MAOB), transferrin (TF) and others (See Table 4). Evaluation of the data (Table 4) revealed that none of these DNA probes utilizing four restriction endonucleases, (which endonucleases, to date, are responsible for about two-thirds of all known polymorphisms) are associated with alcoholism. The cDNA probe for alcohol dehydrogenase, an enzyme involved in the metabolism of alcohol, displays a polymorphism using MspI, but the polymorphism is not linked to alcoholism. The cDNA probe for transferrin, a protein involved in hemoglobin synthesis, displays polymorphism using EcoRI, but again, this polymorphism is not associated with alcoholism. Other probes used were: protein kinase-C, involved in second messenger coupling mechanisms for neurotransmitters; carboxypeptidase-A, involved in the metabolism of the opioid peptide enkephalin; pro-enkephalin, the precursor protein for the synthesis of enkephalin; the enzyme tryptophan hydroxylase, involved in the regulation of serotonin synthesis; tyrosine hydroxylase, the rate-limiting enzyme in the synthesis of dopamine; and transferrin, a protein involved in hemoglobin dynamics. This latter group of probes as well as others displayed no polymorphism with TaqI, MspI, EcoRI, and PstI restriction endonucleases. Thus the only probe that showed polymorphism associated with alcoholism was $\lambda$-D$_2$G1 (ATCC #61354 and 61355).

Over the past three decades, research concerned with the interaction of genetic and environmental factors in the development of alcoholism shows that the risk for this behavior is determined by genetic as well as by environmental factors (Cloninger and Li, 1985; Cloninger, 1986). However, the conclusion that there is a significant genetic component to alcoholism has led to the realization that individuals who are at risk of becoming alcoholic, because of inherited factors, are biologically different from individuals who have few or no inherited factors that predispose them to alcoholism. This notion has stimulated an extensive search for alcoholism genes (alcogenes) or markers to identify individuals at increased risk for alcoholism, a concept elaborated from studies of inbred strains of mice, C57 and DBA, with a differing predilection to alcohol (Myers, 1985).

TABLE 4

Evaluations of Polymorphisms of DNA Probes with Various Endonucleases

| DNA Probe | MspI | EcoRI | TaqI | PstI | XbaI | Alcoholism Association |
|---|---|---|---|---|---|---|
| Alcohol Dehydrogenase(pADH/3) | yes | no | no | no | — | no |
| Protein Kinase-C(phPKC) | no | no | no | no | — | no |
| Tryptophan Hydroxylase(TPH479) | no | no | no | no | — | no |
| Pro-enkephalin(pHPE9) | no | no | no | no | — | no |
| Monoamine Oxidase(MAOB) | no | no | no | no | — | no |
| Carboxypeptidase A(CPA) | no | no | no | no | — | no |
| Carboxypeptidase A(CPA) | no | no | no | no | — | no |
| Transferrin(TF) | no | yes | no | no | — | no |

TABLE 4-continued

Evaluations of Polymorphisms of DNA Probes with Various Endonucleases

| DNA Probe | MspI | EcoRI | TaqI | PstI | XbaI | Alcoholism Association |
|---|---|---|---|---|---|---|
| Tyrosine Hydroxylase(BTH$_4$) | no | no | no | no | — | no |
| Choline Acetyl Transferase (Chat) | no | no | no | no | — | no |
| Serotonin (5HT1A) receptor (GZ1) | no | no | no | no | — | no |
| Catecholamine Receptors | | | | | | |
| 22 | no | no | no | no | — | no |
| B1 | no | no | no | no | — | no |
| B2 | no | no | no | no | — | no |
| GABA Receptors | | | | | | |
| 21 | no | no | no | no | — | no |
| 24 | no | no | no | no | — | no |
| B1 | no | no | no | no | — | no |
| Dopamine B-Hydroxylase | no | no | no | no | yes | no |
| Dopamine (D$_2$) Receptor λ-hD$_2$G1 | no | no | yes | no | — | yes |

It is theoretically possible that the polymorphism of the dopamine (D$_2$) receptor gene in the brains of alcoholics is due to alcohol-induced alteration in DNA (Obe et al., 1979); hence, the polymorphism observed might be a consequence of prolonged alcohol consumption by the alcoholic and thus represent a state marker instead of a trait marker. This possibility is unlikely, given the fairly wide prevalence (24%) of the A1 allele in the general population. Moreover, the presence of the A1 allele and its co-dominant Mendelian inheritance (Grandy et al., 1989) in alcohol-naive children indicate that alcohol per se was not responsible for this genetic variation. It is of further interest to note that naive inbred alcohol-preferring rats show a significantly lower dopamine (D$_2$) receptor binding activity than naive alcohol-avoiding rats (Korpi et al., 1987), suggesting an abnormality in this gene or in its expression. These observations support the idea that the allelic association of the dopamine (D$_2$) receptor gene, or a gene close to it, in brain tissue of alcoholics is a likely candidate trait marker for, at least, one important subtype of potential alcoholism.

Given the evidence that children of alcoholics are at a greater risk of developing alcoholism than children of non-alcoholics (Schuckit, 1986), it may be predicted that the prevalence of a candidate trait marker would be significantly greater in a population of subjects who have a positive rather than a negative family history of alcoholism.

In the present sample, derived from 70 deceased individuals, a strong association between alcoholism and the A1 allele of a TaqI polymorphism close to the dopamine D$_2$ receptor gene has been found. That this association prevailed in a subsample of Caucasians and Blacks raises interesting questions about the prevalence of the A1 allele in other samples of alcoholics. It is, however, important to note that a large majority of alcoholics in the present study had experienced repeated treatment failures in their alcoholic rehabilitation and whose cause of death was primarily attributed to the chronic damaging effects of alcohol on their bodily systems. It is possible then that the A1 allele found in this study may be associated with a particular subgroup of virulent alcoholism. Besides these molecular genetic studies, we have also carried out, in the same brain samples as above, the actual characteristics of the dopamine D$_2$ receptor using [$^3$H]spiperone (a dopamine [D$_2$] receptor antagonist ligand). The data show that the affinity of the dopamine (D$_2$) receptor ligand is significantly different in subjects having the A1 allele compared to those having the A2 allele. Thus, the evidence, put together, shows not only that a strong association is found between the A1 allele and alcoholism, but that the A1 and A2 allele express themselves in different dopamine (D$_2$) characteristics in the brain.

Unlike genetic diseases such as Huntington's chorea and cystic fibrosis (Arinami et al., in press), where a single gene is responsible for its expression, the potential heterogeneous nature of alcoholism may not allow for the generation of a single marker that can identify all individuals at risk.

Given that there are various subtypes of alcoholics (Pickens et al., 1991; Tarter et al., 1977), it would have been surprising if a 100% association was found between the A1 allele and alcoholism. In this regard, the 31% of alcoholics in this study which did not associate with the dopamine (D$_2$) receptor gene A1 polymorphism suggest some interesting possibilities: 1) environmental (Gallistel and Davis, 1983; Imperato and Chiara, 1986; Gessa et al., 1985; Lucchi et al., 1988) rather than genetic factors contributed to their alcoholism; 2) other genes may also be important for the predisposition to and subsequent expression of alcohol-seeking behavior. This latter possibility is intriguing, since it suggests that gene-specific subtypes of alcoholism could now be identified, for example through RFLP analysis, and provide the basis for multiple etiologies; and 3) there may be only partial linkage disequilibrium between the subject RFLP and the gene responsible for the disease. This could occur because of occasional crossover between marker and gene.

Support for alcoholism subtypes can be found in various neurochemical hypothesis, including: 1) individual differences in nerve cell membrane sensitivity to ethanol (Goldstein et al., 1982); 2) inherited variations in the sensitivity of sodium-potassium ATPase inhibition to ethanol (Israel et al., 1965; Swarm, 1985; Nhamburo et al., 1987); 3) inherited variations in neurotransmitter release and uptake systems involved in a reward cascade of events (Bloom, 1979; Blum et al., 1989; Blum, 1989); 4) inherited variations in the production of abnormal amounts of tetrahydroisoquinolines (Smith and Uhl, 1992.); 5) inherited variations in the neuroadaptive mechanisms for reinforcing certain behaviors (Cloninger et al., 1981; Cloninger, 1987; Goodwin, 1989); and 6) inherited variation in second messenger response coupling mechanisms (Allison and Cicero, 1980; Hoffman et al., 1986; Sun et al., 1987; Ritchie et al., 1988; Ross, 1989).

D2 Dopamine Receptor Binding Characteristics in Caudates of Alcoholic and Nonalcoholic Subjects The allelic association of the human $D_2$ dopamine receptor (D2DR) gene with the binding characteristics of the D2DR was determined in 66 brains of alcoholic and nonalcoholic subjects. In a blinded experiment, the DNA from these samples was treated with the restriction endonuclease TaqI and probed with a 1.5 kb fragment from a BamHI digest of λ-hD$_2$G1 (ATCC #61354 and 61355). The binding characteristics ($K_d$, binding affinity and $B_{max}$, maximum number of binding sites) of the D2DR were determined in the caudate nucleus from these brains using ($^3$H)spiperone, a dopamine receptor (D2DR) antagonist ligand. Log $K_d$ was significantly lower in alcoholic compared to nonalcoholic subjects. Moreover, a linear relationship in reduced $B_{max}$ was found respectively in A2A2, A1A2, and A1A1 allelic subjects. In individuals with the A1 allele, where a high association with alcoholism was found, the maximum number of D2DRs ($B_{max}$) was significantly reduced when compared to the $B_{max}$ in individuals with the A2 allele (Noble et al., 1991).

METHODS

Brain Samples

The 66 brains analyzed consisted of the 70 that were previously studied in this example 1 (Blum et al., 1990); 4 caudates were not available.

DNA Probe

The DNA probe, as previously used (Blum et al., 1990), was a 1.73 kb band obtained as a doublet from a BamHI digest of a human genomic fragment, λ-hD$_2$G1 (ATCC #61354 and 61355), provided by O. Civelli. This fragment contains the last coding (7th) exon of the D2DR gene and part of 16.5 kb of 3' flanking sequence (Gelernter et al., 1991; Uhl et al., 1992). The 1.5 kb (doublet) probe was labeled by random-priming with [$^{32}$P]dCTP (Maniatis et al., 1982) to a specific activity of $1\times10^9$ cpm/µg.

DNA Isolation and Southern Blot Analysis

The 66 frozen brain cortical samples were coded without reference to their group identity (alcoholic and nonalcoholic). They were then thawed and processed for high molecular weight genomic DNA and hybridized by established procedures (Maniatis et al., 1982; Blum et al., 1990).

D$_2$ Dopamine Receptor Assay

Sixty-six frozen caudate nuclei, of the same brains from which cerebral cortex DNAs were isolated, were also coded without reference to their group identity, and assayed during a one month period for D2DR characteristics. The frozen samples were routinely ground into a free powder in liquid nitrogen using a mortar and pestle and stored at −70° C. from which small amounts of homogeneous powdered tissue could be used for assays at different times. A sample of 200–300 mg of the powdered tissue was homogenized in 30 ml of ice-cold buffer (50 mmol/l Tris-HCl, pH 7.4; 120 mmol/l NaCl; 2 mmol/l MgCl$_2$) with a Brinkman Polytron cell homogenizer. The homogenate was centrifuged at 35,000×g for 20 min. The pellet was resuspended in 30 ml of buffer and again centrifuged at 35,000×g for 20 min. The final pellet was resuspended in 30 ml of buffer for the binding assay.

D2DR binding was measured by a slight modification of previously established procedures (Seeman and Grigoriadis, 1985; Seeman et al., 1987; De Keyser et al., 1989). Saturation curves (FIG. 6) were obtained using 12 duplicate increasing concentrations (10–1000 pmol/l) of [$^3$H]spiperone (32.4 Ci/mmol; New England Nuclear) in buffer containing 50 mmol/l Tris-HCl, pH 7.4; 120 mmol/l NaCl; 2 mmol/l MgCl$_2$. To measure nonsaturable binding, S-(−)-sulpiride was added to a fmal concentration of 10 µmol/l. Binding was initiated by the addition of membrane preparation (250–350 µg protein), and the samples were incubated in the dark at 20° C. for 2 hr. Final assay volume was 1 ml. The samples were then rapidly filtered through GF/B glass fiber filters with a Brandel cell harvester. The filters were washed twice with 2 ml of ice-cold assay buffer and placed in scintillation minivials with 4 ml of scintillation fluid (National Diagnostics) for counting. Protein concentrations were determined using bovine serum albumin as the standard (Lowry et al., 1951). Maximum number of binding sites ($B_{max}$) and equilibrium dissociation constants ($K_d$) were estimated using the weighted nonlinear least-squares curve-fitting (Munson and Rodbard, 1980) program LIGAND. Data were fit for both one-site and two-site models with the two-site model accepted only if a statistically significant improvement was obtained over the one-site model.

Statistical Analysis

The frequency distributions for $B_{max}$, $K_d$ and $B_{max}/K_d$ were examined for departures from normality. Correlations were estimated for $B_{max}$ with age, Log $K_d$ with $B_{max}$, and $B_{max}/K_d$ with age. Mean differences between groups for $B_{max}$, Log $K_d$ and $B_{max}/K_d$ were tested using two factor analysis of covariance (ANCOVA) to determine the statistical significance of the main effects of allele and alcoholism, the interactions of alleles and the presence or absence of alcoholism. Measures of $B_{max}$ were covariate-adjusted for age and Log $K_d$, and Log $K_d$ measures were covariate-adjusted for $B_{max}$. A one-tailed alpha criteria of <0.05 was used to evaluate all effects upon measures of $B_{max}$ and Log $K_d$. In this study, the more powerful one-sided tests were used when the sample mean fell in the expected direction (Rosner, 1980). No directional expectations were established for $B_{max}/Kd$, therefore, alpha criteria were set at alpha=0.05 using a two-tailed test.

The expression of the A1 allele occurs in both homozygote and heterozygote individuals. These two groups were labeled A1/A1 for homozygotes and A1/A2 for heterozygotes and were compared with A2/A2 homozygote individuals using single factor ANCOVA and polynomial tests for trends of $B_{max}$, Log $K_d$ and $B_{max}/K_d$.

DNA Analysis

In the previous hybridization study in Example I (Blum et al., 1990), using TaqI-digested human DNA, we have shown that a BamHI 1.6 kb doublet of the D2DR gene (λ-hD$_2$G1) (ATCC #61354 and 61355) reduced overall background and was still informative as to the presence of D2DR gene alleles. Three bands were obtained: a constant 10.5 kb band, a 6.6 kb A1 allele and a 3.7 kb A2 allele. Using the BamHI 1.6 kb doublet as probe, TaqI digested DNAs from the caudate nucleus of alcoholic and nonalcoholic brains in the present study were subjected to two independent hybridizations. The results are shown in Tables 4A and 4B. Table 4A presents the 29 DNAs that show the presence of the A1 allele (A1$^+$). Twenty-two (76%) of these DNAs associated with alcoholic subjects and 7 (24%) associated with nonalcoholics. Table 4b shows the 37 DNAs that exhibit the absence of the A1 allele (A1⁻). Eleven (30%) of these DNAs associated with alcoholic subjects and 26 (70%) associated with nonalcoholics. The proportion of the presence of the A1 allele to the absence of this allele is significantly different in alcoholics compared to nonalcoholics (Yates $\chi^2$ [corrected for continuity]=12.06, df=1, P<0.001). This observation, as expected, is similar to our previous study of 70 brains (Blum et al., 1990), of which 66 brains were again probed in the present investigation.

D₂ Dopamine Receptor

Saturation curves, using [³H]spiperone as antagonist ligand and S-(−)-sulpiride to measure nonspecific binding, of each of the 66 caudates studied complied with a single-model binding site (Munson and Rodbard, 1980). To evaluate interassay reliability, replicate determinations, on different days for the same tissue, were also made on a subset of 10 caudates from the present brain samples. Using 100% as the assigned $K_d$ or $B_{max}$ value for the first determination, the second assay revealed $K_d$=104±7.5% and $B_{max}$=103±4.3%. Paired t-tests showed no significant difference between the two determinations. The Spearman rank-order correlation coefficients for $K_d$ and $B_{max}$ were 0.72 and 0.95 respectively. The two-tailed significance levels for $K_d$ and $B_{max}$ were P<0.009 and P<0.001, respectively. These data together reveal no statistically significant differences between the two independent assays, suggesting interassay reliability. Similar good interassay reliability for the binding characteristics of the D2DR in human caudates frozen at postmortem has been observed by others (Seeman et al., 1987).

FIG. 6 shows examples of saturation curves of [³H] spiperone and Scatchard analysis in caudate tissue: (A) non-alcoholic subject with A2A2 allele and (B) nonalcoholic subject with A1A2 allele.

The $K_d$ and $B_{max}$, for each individual caudate in the present study, are shown in Table 5. Table 5A shows the binding characteristics in A1⁺ samples (presence of the 6.6 kb band) and Table 5B depicts the values in A1⁺ samples (absence of the 6.6 kb band). The range of values are consistent with reported results for the binding characteristics of the D2DR in human caudate tissue (Seeman et al., 1984; De Keyser et al., 1989; Severson et al., 1982).

In the total sample of caudates, skewness and kurtosis values for the distribution of $K_d$ were outside the limits of ±1, so the values were re-expressed as their natural logarithms. The log-transformed values for $K_d$ distribution were within acceptable limits for the measures of skewness and kurtosis as were the non-transformed measures for $B_{max}$ and $B_{max}/K_d$.

Correlations between outcome measures were examined to determine if they were non-independent with each other, with age or with autolysis time. Linear correlations were r=−0.37 (P=0.0023, two-tailed) for $B_{max}$ with age, and r=0.68 (P<0.0001, two-tailed) for Log $K_d$ with $B_{max}$. Therefore, age and Log $K_d$ were used as covariates to remove their effects from the measures of $B_{max}$. Likewise, the effects of $B_{max}$ were removed from the effects of the Log $K_d$ measures. No correlations were evident between $B_{max}$ or Log $K_d$ and autolysis time.

TABLE 5

D2 Dopamine Receptor Binding Characteristics in Caudates of Alcoholic and Nonalcoholic Subjects with the Presence or Absence of the A1 Allele of the D2 Dopamine Recpetor Gene (λ-hD2G1)

| A. Presence of the A1 allele | | | | B. Absence of the A1 allele | | | |
|---|---|---|---|---|---|---|---|
| Subject Number | Alcoholic (A) or Nonalcoholic (NA) | $B_{max}$ (fmol/mg protein) | $K_d$ (pM) | Subject Number | Alcoholic (A) or Nonalcoholic (NA) | $B_{max}$ (fmol/mg protein) | $K_d$ (pM) |
| 1 | A | 43.3 | 41.6 | 1 | NA | 65.6 | 74.4 |
| 2 | A | 28.6 | 58.4 | 2 | A | 96.1 | 99.6 |
| 3 | A | 36.5 | 53.4 | 3 | A | 24.5 | 50.4 |
| 4 | A | 84.2 | 66.6 | 4 | NA | 120.3 | 96.7 |
| 5 | A | 46.0 | 36.3 | 5 | A | 85.0 | 63.7 |
| 6 | A | 35.6 | 56.1 | 6 | NA | 78.0 | 105.5 |
| 7 | A | 45.2 | 46.2 | 7 | NA | 27.3 | 47.3 |
| 8 | A | 27.8 | 23.9 | 8 | A | 23.4 | 45.2 |
| 9 | NA | 56.1 | 57.4 | 9 | NA | 53.4 | 70.0 |
| 10 | A | 137.1 | 125.7 | 10 | NA | 122.2 | 131.7 |
| 11 | A | 59.6 | 72.1 | 11 | NA | 140.6 | 105.6 |
| 12 | NA | 52.4 | 89.2 | 12 | A | 152.8 | 117.9 |
| 13 | A | 39.4 | 49.5 | 13 | NA | 65.8 | 69.8 |
| 14 | A | 47.8 | 61.6 | 14 | NA | 146.0 | 137.8 |
| 15 | NA | 62.0 | 74.9 | 15 | NA | 123.9 | 114.7 |
| 16 | A | 55.9 | 62.1 | 16 | A | 99.4 | 73.3 |
| 17 | A | 115.5 | 124.2 | 17 | A | 67.8 | 67.8 |
| 18 | NA | 39.6 | 51.2 | 18 | NA | 41.5 | 47.2 |
| 19 | A | 45.2 | 42.6 | 19 | NA | 53.4 | 70.0 |
| 20 | NA | 55.2 | 72.9 | 20 | NA | 82.3 | 110.7 |
| 21 | A | 78.5 | 118.7 | 21 | NA | 58.2 | 53.3 |
| 22 | A | 77.2 | 144.0 | 22 | A | 78.9 | 69.4 |
| 23 | NA | 46.0 | 55.2 | 23 | A | 37.0 | 40.6 |
| 24 | A | 50.2 | 95.0 | 24 | NA | 41.6 | 198.3 |
| 25 | A | 69.3 | 104.1 | 25 | NA | 115.0 | 143.1 |
| 26 | A | 38.4 | 62.7 | 26 | NA | 73.8 | 118.4 |
| 27 | NA | 6.6 | 69.0 | 27 | A | 35.3 | 71.7 |
| 28 | A | 17.8 | 56.3 | 28 | NA | 86.4 | 228.0 |
| 29 | A | 60.3 | 87.4 | 29 | NA | 35.8 | 45.0 |
| | | | | 30 | A | 68.3 | 66.5 |

TABLE 5-continued

D2 Dopamine Receptor Binding Characteristics in Caudates of Alcoholic
and Nonalcoholic Subjects with the Presence or Absence of the
A1 Allele of the D2 Dopamine Recpetor Gene (λ-hD2G1)

| A. Presence of the A1 allele | | | | B. Absence of the A1 allele | | | |
|---|---|---|---|---|---|---|---|
| Subject Number | Alcoholic (A) or Nonalcoholic (NA) | $B_{max}$ (fmol/mg protein) | $K_d$ (pM) | Subject Number | Alcoholic (A) or Nonalcoholic (NA) | $B_{max}$ (fmol/mg protein) | $K_d$ (pM) |
| | | | | 31 | NA | 87.8 | 95.7 |
| | | | | 32 | NA | 99.1 | 97.8 |
| | | | | 33 | NA | 92.0 | 121.8 |
| | | | | 34 | NA | 44.9 | 80.8 |
| | | | | 35 | NA | 62.5 | 140.8 |
| | | | | 36 | NA | 45.1 | 53.3 |
| | | | | 37 | NA | 23.3 | 36.9 |

Subjects 3, 9, 22 and 27 under a are homozygous for the A1 allele

Table 6 compares the unadjusted and adjusted $K_d$ and $B_{max}$ in caudates of alcoholic and nonalcoholic individuals and that of $A1^+$ and $A1^-$ allelic subjects. In Table 4A, the mean Log $K_d$ in samples of the alcoholic group, after covariate adjustment for $B_{max}$, was found to be significantly lower than that of the nonalcoholic group when tested using a two-factor ANCOVA (P=0.023, one-tailed). No significant $B_{max}$ differences were found among these two groups. Table 5B shows the unadjusted $B_{max}$ of $A1^+$ allelic subjects to be significantly lower (P<0.008, one-tailed) than that of $A1^-$ allelic subjects. Further, $B_{max}$ measures were covariate-adjusted for age as well as Log $K_d$ values and also tested using two-factor ANCOVA. The main effect for allele was still evident (P<0.01, one tailed), with the adjusted $B_{max}$ mean of the $A1^+$ group being smaller than that of the $A1^-$ group. No significant differences were found in $K_d$ measures when classification was based on the presence or absence of the A1 allele.

Covariate-adjusted means for $B_{max}$ and Log $K_d$ of the D2DR were also compared in four subgroups of 66 caudates derived from: $A1^+$ non-alcoholics (n=7), $A1^+$ alcoholics (n=22), $A1^-$ nonalcoholics (n=26) and $A1^-$ alcoholics (n=11). The differences between the alleles for the $B_{max}$ measures were parallel between alcoholics and nonalcoholics, thus no factor interaction was detected.

Comparisons of binding measures among the A2A2, A1A2 and A1A1 groups indicated differences only for measures of $B_{max}$ (P=0.034, two-tailed). A test for polynomial trends among the three groups demonstrated a linear relationship (P=0.01, two-tailed) with the highest means for A2A2 followed by the A1A2 samples and with the lowest for the A1A1 group. Fisher's LSD post hoc test found a significant (P<0.05) difference between the A2A2 and A1A2 groups. While the A1A1 mean was the lowest, no significant differences were obtained with a sample size of four when compared with either of the two other groups.

TaqI digests of human DNA, probed with a clone of a human genomic fragment of the D2DR gene (λ-hD₂G1)(ATCC #61354 and 61355), reveal two alleles: A1 and A2

TABLE 6

Binding Characteristics of the $D_2$ Dopamine Receptor in Caudate of
Alcoholic and Nonalcoholic Subjects (a) and as a Function
of the Presence (+) or Absence (−) of the A1 Allele (b)

| | a. Alcoholic and nonalcoholic subjects | | |
|---|---|---|---|
| | Alcoholics (n = 33) | | Nonalcoholics (n = 33) |
| $K_d$ (pM) | | | |
| Unadjusted | 71.0 ± 5.2 | NS | 92.8 ± 7.6 |
| Log $K_d$1 | 4.19 ± 0.06 | P < 0.023 | 4.38 ± 0.07 |
| $B_{max}$ (fmol/mg protein) | | | |
| Unadjusted | 60.8 ± 5.6 | NS | 69.8 ± 6.0 |
| Adjusted[2] | 67.9 ± 4.4 | NS | 59.5 ± 4.9 |
| | b. $A1^+$ and $A1^-$ allelic subjects | | |
| | $A1^+$ (n = 29) | | $A1^-$ (n = 37) |
| $K_d$ (pM) | | | |
| Unadjusted | 70.9 ± 5.4 | NS | 90.5 ± 7.1 |
| Log $K_d$[1] | 4.31 ± 0.07 | NS | 4.27 ± 0.06 |

TABLE 6-continued

Binding Characteristics of the $D_2$ Dopamine Receptor in Caudate of
Alcoholic and Nonalcoholic Subjects (a) and as a Function
of the Presence (+) or Absence (−) of the A1 Allele (b)

| $B_{max}$ (fmol/mg protein) | | | |
|---|---|---|---|
| Unadjusted | 53.7 ± 4.9 | P < 0.008 | 74.4 ± 5.9 |
| Adjusted[2] | 55.8 ± 5.2 | P < 0.01 | 71.7 ± 4.2 |

[1]Log-transformed and covariate-adjusted for $B_{max}$ by least-square estimations.
[2]Covariate-adjusted for Log $K_d$ and age by least-square estimations. Significance obtained by one-tailed test; NS + not significant.

(Grandy et al., 1989). The present data show that digests of DNA, obtained from the cerebral cortex of alcoholics and nonalcoholics, when probed with the 1.6 kb doublet of λ-hD$_2$G1 (ATCC #61354 and 61355), reveal the A1 allele to be associated with alcoholics and its absence to be associated with non-alcoholics. Since the caudate nucleus is among brain regions with the highest expression of the D2DR, the question raised herein is whether a relationship exists among the binding characteristics of this receptor and the polymorphic pattern of the D2DR gene in caudates of alcoholic and nonalcoholic subjects.

It should be noted that the alcoholics of the present study had a very severe type of alcoholism (Blum et al., 1990). Detailed clinical records, interviews of next of kin and examination at autopsy (both macroscopic and microscopic) revealed that these alcoholics not only had a history of heavy alcohol consumption and multiple failures in their alcoholic rehabilitation but also, in a majority of them, the cause of death was attributed to the damaging effects of alcohol on their bodily systems.

That severity of alcoholism is an important determinant in A1 allelic association is shown in an analysis of a recent study by Bolos et al. (Bolos et al., 1990) which used a different and less severe alcoholic population than the inventors' sample. In that study of blood obtained from living Caucasian subjects, patients were divided into two groups: less severe and more severe alcoholics. Using the inventors' two Caucasian groups (nonalcoholics and very severe alcoholics) and the three groups of Bolos et al. (Bolos et al., 1990) (CEPH 'controls' [alcoholics not excluded], less severe and more severe alcoholics) a $\chi^2$ test for linear trend was conducted for prevalence of the A1 allele. Increasing degree of alcoholism severity was found to correspond with significant increase (P=0.0002) of A1 allele prevalence (Noble and Blum, 1991). Moreover, Cloninger et al (Cloninger et al., 1991), utilizing a population of very severe Caucasian alcoholics similar to inventors' and controls (alcoholics rigorously excluded), found 60% of the former group and 20% of the latter group to have the A1 allele. This distribution of the A1 allele in their two groups closely corresponds to the original observation (Bunzow et al., 1988).

The polymorphic pattern of this gene and its differential expression of receptors suggests the involvement of the dopaminergic system in conferring susceptibility to at least one subtype of alcoholism.

Isolation of Probe From Doublet Band

The parent clone, λ-hD$_2$G1 (ATCC #61354 and 61355), was obtained and digested with BamHI and run on 0.8% agarose (not Sea Plaque™) and the bands visualized with ethidium bromide staining. FIG. 7 indicates a doublet in the gel on the right labeled "Doublet 1.73 kb" with DNA molecular weight standards shown in the gel on the left. For equal amounts of different, unrelated fragments, one would expect the smaller fragments to stain with less intensity since fewer nucleotides would be present. Since the two bands labeled Doublet 1.73 indicated less staining intensity in the upper, larger kb band than in the lower, smaller kb band and since only one band was sometimes observed, it was suspected that the 1.73 kb fragment may consist of two, perhaps related, fragments. Hence, the 1.73 fragment was labeled Doublet 1.73 kb.

This 1.73 kb fragment was originally estimated by gel electrophoresis to 1.6 kb (personal communication from D. K. Grandy). Since this fragment has not actually been sequenced, any reference in this application to the doublet 1.73 or 1.73 kb fragment or probe should be considered equivalent to doublet 1.6 or a 1.6 kb or 1.5 kb fragment or probe.

To check the possibility of the 1.6 kb fragment being a doublet, a ligation was performed using this fragment by following the procedure given by Sea Plaque GTG agarose (FMC BioProducts, 5 Maple Street, Rockland, Me. 04841-2994 USA). Transformation of DH5α cells was performed following the Hanahan method (Hanahan, *J. Mol. Biol.* 166 (1983):557–580).

In order to differentiate between different clones, minipreps were performed and the DNA cut with a series of enzymes (HinfI, MspI, TaqI, BamHI, and HindIII) establishing two definite populations containing inserts of the appropriate size (1.6 kb). These two subclones, named #9 and #16, were grown and the DNA purified. The 1.6 kb fragments from each clone were labeled with $^{32}$P and used as probes to hybridize onto human genomic DNA cut with TaqI using the same procedure described in Example 1.

FIG. 8 shows that the 1.6 kb probe from clone 9 hybridized with human genomic DNA cut with TaqI at 6.6 kb and 3.7 kb, whereas the 1.6 kb probe from clone 16 hybridized with a band at 10.5 kb. Through this subcloning of the 1.6 kb fragment, two 1.6 kb fragments were separated since the original 1.6 kb probe, suspected of comprising a doublet, hybridized with human genomic DNA cut with TaqI gave three bands located at 10.5 kb, 6.6 kb, and 3.7 kb. Thus, the 1.6 kb fragment from clone 9 is informative as a probe for the presence of the A1 allele in human genomic DNA.

Allelic Association of the D2 Receptor Gene in Alcoholism Using DNA Obtained From Living Subjects Individuals categorized as non-alcoholic, alcoholic, children of alcoholics (COA), or drug abuser (DA) were tested for the presence of the A1 allele. Subjects were assigned to a particular category after they filled out a standard chemical identification diagnostics form for substance abuse developed by E. P. Noble, Kenneth Blum, and associates as well as DSMR-3, criteria assessed by a clinician (DSMR-3 form). The 1.6 kb fragment from clone 9 was used as a hybridization probe for detecting the presence or absence of the A1 allele in the subject's DNA isolated from lymphocytes. Genomic DNA from lymphocytes was obtained by the following methodology.

Isolation of Genomic DNA from Lymphocytes

1) Collect blood in (2) capped tubes without heparin.
2) Put 10–15 mls of whole blood into a polycarbonate tube (50 ml) and fill the remainder of the tube with DNA isolation solution [0.3M sucrose, 10 mM Tris (pH 7.5), 5 mM $MgCl_2$, 1% Triton® X-100]. Mix by inversion.
3) Centrifuge at 4,000 rpm at 4° C. for 10 min. Aspirate the supernatant into bottle containing bleach. Wash the pellet once again with the same solution. Repeat if needed until no red blood cells are apparent.
4) quickly resuspend pellet in 4.7 mls with TE and transfer into one 30 ml corex tube.
5) Slowly add 250 µl of Proteinase K (10 mg/ml in TE). Gently mix.
6) Incubate 3 hr. to overnight at 37° C. in a water bath. Swirl the viscous solution periodically.
7) Gently extract the DNA 1 time with an equal volume of phenol (pH 8.0) by mixing and immediately centrifuging for 10' at 5,000 rpm. Remove aqueous layer (top) carefully. Gently extract aqueous phase with 1 vol. of chloroform: isoamyl alcohol (24:1) mix gently and centrifuge immediately. Centrifuge for 10' at 5,000 rpm. Transfer aqueous layer to polypropylene tube.
8) Add 1/10 volume (0.5 ml) of 3M sodium acetate plus total volume (5.5 ml) of cold isopropanol. Invert slowly to mix. DNA should fall out immediately.
9) Remove DNA with looped pipet. Wash DNA with 70% ETOH, air dry briefly.
10) Resuspend in 400 to 600 µl TE (pH 7.6) in 1.5 ml flip cap tube. Store at 4° C.
11) Measure the exact concentration of the DNA and analyze an aliquot by electrophoresis through a 0.3% agarose gel. The DNA should be greater than 100 kb in size and should migrate more slowly than a marker of intact bacteriophage. Store DNA at 4° C.

Hybridizations using the 1.6 kb probe of clone 9 were carried out utilizing the hybridization conditions described in this example. Results of these tests are summarized in Table 7. Of 49 individuals diagnosed as alcoholic, 63% were positive for the A1 allele whereas 22% of 41 nonalcoholics were positive for the A1 allele. Table 7 shows a good correlation between the findings previously cited where the A1 allele was detected in brain samples from deceased subjects, and the findings of this study, where the A1 allele was detected in living subjects. The previous study, summarized in Table 3, indicated nonalcoholics with 20% $A1^+$ (having the A1 allele) and 80% $A1^+$ (without the A1 allele), whereas Table 5 indicates nonalcoholics with 22% $A1^+$ and 78% $A1^-$. Similarly, the alcoholics were found in the brain tissue study to have 69% $A1^+$ and 31% $A1^-$, whereas in the present study with lymphocyte DNA, alcoholics were found to have 63% $A1^+$ and 37% $A1^-$. These findings fit very well with other recent studies such as those of Cloninger et al. (Cloninger et al., 1991), where a much larger number of living alcoholics and nonalcoholics were tested for the presence of the A1 allele. In the Cloninger et al. study, the A1 allele was found to be present in 20% of the nonalcoholics versus 60% of the alcoholic (Table 6:22% nonalcoholics versus 63% alcoholics).

In view of interviews with the subjects in this study, it is likely that the A1 allele may be predictive of attention deficit disorder with hyperactivity (ADDH). Further, coupling of a determination for ADDH with the presence of the A1 allele may allow for a more reliable detection of alcoholism susceptibility or may be of benefit in identifying a certain subtype of alcoholism. The coupling of other indicators with the presence of the A1 allele may offer a significant advance in the detection, prediction or diagnosis of a susceptibility for other compulsive disorders.

It is viewed as possible that the dopamine ($D_2$) receptor gene polymorphism observed herein may also be associated with predilection to other addictive disorders, such as those relating to nicotine, narcotics or other drugs, for example.

It is believed that research dealing with the exploration of various candidate gene probes which encode elements related to the synthesis, metabolism, storage, release, and receptor activity of neurotransmitters and neuropeptides involved in brain reward should ultimately lead to multigene trait markers for detection of susceptibility to compulsive disorders of individuals with a family history of alcoholism, for example.

It is well known that relapse of individuals is often related to stressful situations. It is of interest that in an experiment using brain tissues that had been classified as having the A1 or A2 allele in a prior study, the present inventors attempted to answer the question of whether the presence of the A1 allele leads to an altered number of $D_2$ receptors in the brain. By measuring the number of dopamine $D_2$ receptors in the caudate nucleus, an area that normally has the highest density of these receptors, the inventors found that individuals having the A1 allele had approximately 30 percent fewer $D_2$ receptors than those with the A2

TABLE 7

Allelic Association of the $D_2$ Receptor Gene in Alcoholism using DNA obtained from Lymphocytes

| Group | Type | N | Average Age | M | F | (+) FH | (−) FH | (+) FH $A_1+$ | (+) FH $A_1-$ | (−) FH $A_1+$ | (−) FH $A_1-$ | TOTAL $A_1+$ | TOTAL $A_1-$ | Average P Values (Yates Chi-Squares) |
|---|---|---|---|---|---|---|---|---|---|---|---|---|---|---|
| A | Non-Alcoholics* | 41 | 42.6 | 19 | 22 | 27 | 14 | 26% | 74% | 14% | 86% | 22% | 78% | — |
| B | Alcoholics** | 49 | 46.3 | 35 | 14 | 44 | 5 | 66% | 34% | 40% | 60% | 63% | 37% | .003[a] |
| C | COA*** | 17 | 11.0 | 10 | 7 | 17 | 0 | 53% | 47% | — | — | 53% | 47% | .045[a] |
| D | DA**** | 18 | 37.0 | 8 | 10 | 14 | 4 | 21% | 79% | 25% | 75% | 22% | 78% | NS[a]/.009[b] |

TABLE 7-continued

Allelic Association of the D₂ Receptor Gene in Alcoholism using DNA obtained from Lymphocytes

| Group | Type | N | Average Age | M | F | (+) FH | (−) FH | (+) FH A₁+ | (+) FH A₁− | (−) FH A₁+ | (−) FH A₁− | TOTAL A₁+ | TOTAL A₁− | Average P Values (Yates Chi-Squares) |
|---|---|---|---|---|---|---|---|---|---|---|---|---|---|---|

*Subjects diagnosed as non-alcoholics include alcohol abuse but no dependence or less severe
**Subjects diagnosed as alcoholic include dependence and most severe
***Subjects are children of alcoholics have at least one biologic parent clinically diagnosed as alcoholic
****Subjects are clinically diagnosed as drug abusers and drug dependence where alcohol, if used, is not the drug of choice
(+)FH Family history - one or more of the subjects' family members (parents or siblings) were diagnosed alcoholics
(−)FH Family history - NO family members diagnosed as alcoholic.
[a]P values determined by comparison to the "TOTAL" value for Non-Alcoholic
[b]P values determined by comparison to the "TOTAL" value for the Alcoholic allele. Since the dopamine $D_2$ receptor gene controls the production of these receptors, this suggests that the presence of the A1 allele causes a reduction in the number of receptors.

This finding suggests an interesting hypothesis. It is known that dopamine acts to reduce stress. When stress occurs in an individual with a normal number of dopamine receptors, dopamine is released, all of the receptors are filled, and equilibrium is restored. In an individual who has the A1 allele, however, the shortage of dopamine receptors interferes with this process and equilibrium is not restored. This person may seek alcohol or other substances or stimuli that release dopamine or otherwise mask its deficiency, in the attempt to find relief and pleasure. The desired effects do not come, however, because of the shortage of receptors, and the attempt is repeated, leading to aberrant pleasure-seeking behavior. The inventors call this concept the stress-dopamine-genotype hypothesis of craving. Taken together, the findings of a high association of the A1 allele of the $D_2$ receptor gene as well as a 30% reduction of the $D_2$ receptors in A1 allele carriers suggest the importance of diagnosing alcoholism and related behaviors including stress for risk potential.

A polymorphism of the dopamine receptor gene associated with alcoholism and its potential association with other addictive diseases is taught by the present invention. The use of the λ-hD₂G1 (ATCC #61354 and 61355) or 1.6 kb probes for detecting the A1 allele polymorphism of TaqI digests are believed to exemplify one approach to detecting the D2DR gene polymorphism associated with alcoholism. The specific approach used in the present application by way of example does not preclude alternative approaches to polymorphism detection in this gene. Basically, the present disclosure teaches of a polymorphism for the dopamine receptor gene associated with alcoholism which may be detected using other approaches, in addition to that exemplified in the present disclosure by the A1 allele polymorphism in TaqI digests of human genomic DNA. For example, Bolos et al. detect a polymorphism by amplifying a 3' noncoding region of the dopamine receptor gene sequence with PCR™ (polymerase chain reaction) and separating the amplified fragments by electrophoresis under nondenaturing conditions. This approach is stated to reveal polymorphisms that affect the secondary structure of the single DNA strands which are amplified. Thus, the present invention encompasses alternative methods of detecting polymorphisms in the dopamine receptor gene which have been shown by the instant invention to be associated with alcoholism in humans.

Allelic Association of the D2 Receptor Gene in Medically Ill Nonalcoholic Controls An additional study examined the allelic prevalence of the $D_2$ dopamine receptor (DRD2) A1 allele in 70 alcoholics and 80 medically ill nonalcoholics. The patients were all hospitalized individuals recruited from six hospital sites in Los Angeles County. This is the first study where DRD2 alleles were determined in medically ill nonalcoholics. Racial distribution was 62 caucasian and 8 black alcoholics and 69 caucasian and 11 black nonalcoholics. The presence of the A1 allele was not significantly different between either the caucasian and black alcoholics or between the caucasian and black nonalcoholics and so the data on the races in each of these two groups were combined. A1 allelic prevalence was 50% in the alcoholics and 30% in the nonalcoholics ($\lambda^2$=5.45, P=0.020). The nonalcoholics were divided into two subgroups: (a) smokers or drug users and (b) nonsmokers and nondrug users. In the (a) group (n=58), the prevalence of the A1 allele=34.5% and in the (b) group the prevalence of the A1 allele=18.2%. The prevalence of the A1 allele was more than 2.7 fold greater in the alcoholic group than in the (b) group (nonsmoking nonalcoholics). Using the (b), (a) and the alcoholic groups respectively, linear trend analysis showed a significant increase in the prevalence of the A1 allele ($\chi^2$=7.69, df=1, P=0.0056).

At this time, the present findings of an allelic association of the dopamine ($D_2$) receptor gene with alcoholism suggest that a defect in this gene, or in another gene with linkage disequilibrium with it, may cause susceptibility to at least one type of alcoholism. Still, this finding holds promise for specifically focused treatment and prevention strategies. Clearly, application of the discoveries and methods described herein should have great benefit for the 28 million children of alcoholics who are potentially at risk for this disease. Finally, this research, as well as other work along similar lines, should result in the destigmatization of alcoholism, and ensure that the erroneous view of it as a moral weakness should no longer be accepted by society.

EXAMPLE 2

ASSOCIATION OF THE D₂ DOPAMINE RECEPTOR TaqI B1 RFLP WITH SEVERE ALCOHOLICS

Hauge et al. (1991) have reported an additional polymorphism at the DRD2 locus. This more 5' TaqI B RFLP is located closer to the regulatory and structural/coding regions of the gene than the more 3' TaqI A1 or 2 RFLPs. In contrast to the λ-hD₂G1 (ATCC #61354 and 61355) probe which detects the TaqI A alleles and contains exon 8 and the 3' untranslated portion of the DRD2 gene, the λ-hD$_2$G2 probe, which detects the TaqI B alleles, is located 5' of the first coding exon of the DRD2 gene (see FIG. 13). Since the involvement of another polymorphism of the DRD2 gene with alcoholism strengthens the previous association studies (Gelernter et al., 1991 and see Example 1), the inventors examined the distribution of DRD2 TaqI B alleles (B1 and B2) in alcoholism. The present example presents data on the prevalence of B1 and B2 alleles in blood samples and brain tissue from less severe alcoholics, severe alcoholics and controls and compares it to the previously described distribution of A1 and A2 alleles in these subjects.

An additional aspect of the present invention is the association of a human dopamine D$_2$ receptor gene B1 allele presence in the DNA of an individual as determining a genetic potential susceptibility to severe alcoholism. The present example describes studies that illustrate this association.

The results of this study show that, whereas the prevalence of the B1 allele is marginally higher in the total alcoholic sample compared to controls, significant differences emerge when alcoholics are subdivided into less severe and severe groups. Specifically, white severe alcoholics reveal significantly higher prevalence of the B1 allele when compared to either less severe alcoholics or nonalcoholic controls. On the other hand, the slightly higher prevalence of the B1 allele in the less severe alcoholic group is not significantly different from the prevalence of this allele in the nonalcoholic group. However, when the data are subjected to linear trend analysis, increasing degree of alcoholism severity corresponds to a significant increase of the B1 allele. This evidence, like previous results on the A1 allele (Blum et al., 1991; Parsian et al., 1991 and see Example 1), shows that severity of alcoholism, as determined by the presence of medical complications and the presence of dependency symptoms, is an important factor in obtaining association with the subject DRD2 gene allele.

Classification of Less Severe and Severe Alcoholic Groups

The subjects in the blood sample study, 133 nonalcoholics and alcoholics, were previously studied for the prevalence of DRD2 TaqI A alleles (Blum et al., 1991 and Example 1 ). The alcoholic volunteers were inpatients at alcoholic rehabilitation centers or alcoholics attending self-help groups. The nonalcoholic volunteers were treatment staff at alcohol rehabilitation centers or university faculty/staff members. All subjects were diagnosed as nonalcoholic, alcohol abuse or alcohol dependent, using DSM-III-R criteria (American Psychiatric Association, 1987). Moreover, the alcoholic subjects were subclassified on the basis of alcoholism severity as previously reported (Blum et al., 1991). The three independent instruments of severity used were: the Severity of Alcohol Dependence Questionnaire (SADQ)(Stockwell et al., 1985) and the Alcohol Use History Questionnaire and the Medical Alcohol Checklist. Without knowledge of genotype, alcoholics were subclassified as less severe based on the presence or absence of dependency symptoms, and the absence of medical complications of the disease. Severe alcoholics displayed both dependency symptoms and medical complications (i.e. gastric ulcers, gastritis, chronic liver disease including hepatitis and cirrhosis, esophageal varices, ascites, among others). A high degree of concordance was found among the three severity instruments used and complete agreement between the two independent raters in the classification of alcoholism severity. Each subject was further assessed by a structural interview whereby family history was carefully evaluated. Additionally, the patient was required to respond to a detailed questionnaire concerning drug use history of close relatives.

Institutional Review Board approval was obtained for this study, and informed consent was signed by the subjects after the nature of the procedures and maintenance of confidentiality were explained to them.

In the brain tissue study, diagnoses of alcoholism were made independently by two trained psychiatrists using DSM-III-R criteria of alcohol dependence and abuse through examination of medical and autopsy records, interviews of treatment center personnel and relatives, and alcohol consumption data. These two assessments were 100% concordant in diagnosing alcoholic and nonalcoholic subjects. Examination of medical records and/or results of analysis of body fluids at autopsy did not indicate that any of the subjects had used neuroleptic agents. The causes of death included accidents, gunshot wounds, myocardial infarction, heart failure, cancer, gastrointestinal bleeding, suicide, and pneumonia. Informed consent was obtained from next of kin to perform this study.

Genotyping of Study Subjects

Brain tissue from 35 alcoholic and 34 nonalcoholic subjects was obtained from the National Neurological Research Bank at the Wadsworth Veterans Affairs Medical Center, Los Angeles, Calif. The frontal gray cortex and caudate nucleus of each subject were removed from the brain at autopsy by a neuropathologist and immediately frozen at −70° C. until used. The brains analyzed consisted of the 69 that were previously probed for the TaqI "A" RFLP (Blum et al., 1990 and Example 1).

The 133 blood samples and the 69 frozen cortical samples were coded without reference to their group identity (alcoholics or nonalcoholics). High-molecular- weight genomic DNA was extracted, digested with TaqI followed by agarose gel electrophoresis, transferred to nylon membranes and hybridized using established procedures (Maniatis et al., 1982).

A 3.7 kb BamHI fragment of λ-hD$_2$G2 clone was obtained as described (Hauge et al., 1991), subcloned into the BamHI site of pUC-18 and labeled using random-priming with [α-$^{32}$P] dCTP to a specific activity of $2\times10^6$ cpm/ml. Using this labeled probe, hybridization was performed with TaqI DNA digests for 16–24 hr. at 42° C. in 50% formamide, 6X SCC, 1% SDS, 200 μg/ml salmon DNA. Washing for 30 min in 2X SCC/0.1% SDS at room temperature was followed by a 30-min wash at 42° C. Blots were then washed in 0.2X SCC/0.1% SDS at 65° C. for 7 min. Washed blots were exposed to Kodak XAR film for 1–6 days with an intensity screen at −70° C. The resultant pattern was compared to DNA molecular weight standards yielding a 4.6 kb B1 allele and a 4.1 kb B2 allele (Hauge et al., 1991). All genotypes were independently scored by three investigators without knowledge of clinical group status.

Statistical Analysis

The association between the presence of the B1 allele of the DRD2 gene and severity of alcoholism was tested using a two-tailed Yates $\chi^2$ corrected for continuity (Marascuilo and McSweeney, 1977) except when the N was below 41 and then Pearson's $\chi^2$ was utilized. Furthermore, the data combined alcoholic (less severe and severe) group is compared to the nonalcoholic group (Yates $\chi^2$=4.23, P=0.04).

TABLE 8

Allelic Association of the $D_2$ Dopamine Receptor Gene in Nonalcoholics and
Alcoholics with the Presence (FH$^+$) or Absence (FH$^-$) of Family History of Alcoholism

| Type | N | Age (years) ± (SEM) | Sex M | Sex F | Race White | Race Black | FH$^{+*}$ B1$^+$ | FH$^{+*}$ B1$^-$ | FH$^-$ B1$^+$ | FH$^-$ B1$^-$ | Total B1$^+$ | Total B1$^-$ |
|---|---|---|---|---|---|---|---|---|---|---|---|---|
| Nonalcoholics | 41 | 40.2 ± 2.2 | 19 (46.3) | 22 (53.7) | 30 (73.2) | 11 (26.8) | 4 (19.0) | 17 (81.0) | 2 (10.0) | 18 (90.0) | 6 (14.6) | 35 (85.4) |
| Alcoholics | 92 | 45.5 ± 1.4 | 61 (66.3) | 31 (33.7) | 85 (92.4) | 7 (7.6) | 28 (33.3) | 56 (66.7) | 3 (37.5) | 5 (62.5) | 31 (33.7) | 61 (66.3) |
| Less Severe | 40 | 47.2 ± 2.3 | 27 (67.50) | 13 (32.5) | 36 (90.0) | 4 (10.0) | 6 (17.6) | 28 (82.4) | 1 (16.7) | 5 (83.3) | 7 (17.5) | 33 (82.5) |
| Severe | 52 | 44.1 ± 1.6 | 34 (65.4) | 18 (34.6) | 49 (94.2) | 3 (5.8) | 22 (44) | 28 (56) | 2 (100.0) | 0 (0.0) | 24 (46.2) | 28 (53.8) |

*FH$^+$ Includes subjects with one or more first degree family member diagnosed as alcoholic. Number in parentheses represents %.

were also subjected to a $\chi^2$ linear trend analysis (Cochran, 1954) to determine at what level of statistical significance increasing severity of alcoholism is associated with an increase in the presence of the allele in the present sample. In an effort to verify that individual statistical relationships are due to other than chance, and simultaneously to select the best allelic predictor of association with alcoholism, a stepwise logistic regression procedure (Engleman, 1990; Hosmer and Lemeshow, 1989) was employed.

Frequencies for both DRD2 TaqI A alleles (as previously reported (Blum et al., 1991)) and DRD2 TaqI B alleles were compared utilizing two-tailed Yates $\chi^2$ analysis for all subjects.

Association of the B1 Allele in Blood Samples
from Nonalcoholics, Less Severe and Severe
Alcoholics FIG. 9 presents the hybridization pattern utilizing the 3.7 kb fragment of the $\lambda$-hD$_2$G2 clone to detect three genotypes: B1/B1, B1/B2 and B2/B2.

The identifying band in individuals carrying the B1 allele is the 4.6 kb band (B1/B1 and B1/B2) whereas in those individuals who carry the B2 allele, the identifying band is the 4.1 kb band (B1/B2 and B2/B2).

Table 8 shows age, sex, race and familial history of alcoholism in the 133 subjects studied. The average age±SEM of the 92 alcoholics and 41 nonalcoholics was 45.5±1.4 years and 40.2±2.2 years, respectively. Using analysis of variance, no significant age differences are found between the nonalcoholic and total alcoholic group, or among nonalcoholics or subsamples of less severe and severe alcoholics. Whites are more highly represented than blacks in this subject population (115 vs. 18).

Table 8 also shows allelic distribution of the DRD2 gene in the various groups studied. The B1 allele of the DRD2 gene was found in 31 (33.7%) of 92 alcoholics, but only in 6 (14.6%) of 41 nonalcoholics. In contrast, the absence of the B1 allele associated in 35 (85.4%) of 41 nonalcoholics and with 61 (66.3%) of 92 alcoholics. The difference in the presence of the B1 allele is marginally significant when the Since race is an important determinant in allelic prevalence (Blum et al., 1990; Blum et al., 1991), the TaqI B genotypes of the DRD2 gene were compared in the present black and white subjects. In contrast to a 22.2% prevalence of the B1 allele in the total sample of 18 blacks, a 28.7% prevalence of this allele is found in the 115 whites. The % distribution of B1/B1, B1/B2 and B2/B2 genotypes respectively in the three black groups are: 9.1%, 9.1% and 81.8% in nonalcoholics (n=11); 0%, 25.0% and 75.0% in less severe alcoholics (n=4) and 0%, 33.3% and 66.7% (n=3) in severe alcoholics. No significant differences in B1 allele prevalence is found among the three groups in this small sample of blacks.

Association of the B1 Allele in Blood Samples
from White Nonalcoholics, Less Severe Alcoholics
and Severe Alcoholics Table 9 presents data on DRD2 B alleles in the three white groups studied. The B1 allele was found in 4 (13.3%) of 30 nonalcoholics, and 29 (34.1%) of 85 alcoholics. The B1 allele frequency is not significantly different between the nonalcoholic and the combined alcoholic group (Yates $\chi^2$ [Blum et al., 1990]=3.72, P=0.054). However, when comparisons are made between white nonalcoholics and severe alcoholics, and between white less severe and severe alcoholics, significant differences are obtained. Specifically, the B1 allele associates with 6 (16.6%) of 36 less severe alcoholics and with 23 (46.9%) of 49 severe alcoholics. The proportion of the presence of the B1 allele to the absence of this allele is significantly different between nonalcoholics and severe alcoholics, and between less severe and severe alcoholics (Table 9). However, no significant differences in B1 and B2 alleles are found between nonalcoholics and less severe alcoholics. Using B1 allelic prevalence in nonalcoholics and less severe and severe alcoholics a $\chi^2$ test for linear trend shows that increasing degree of alcoholism severity corresponds to a significant increase in the prevalence of the B1 allele ($\chi^2$ [Blum et al., 1990]=11.72, P=0.0006).

An analysis of B1 prevalence, based on sex, was determined in the white combined alcoholic and nonalcoholic groups. In men, the B1 allele associates with 20 (36.4%) of 55 alcoholics but associates with only 2 (15.4%) of 13 nonalcoholics. The proportion of the

TABLE 9

TaqI B Alleles of the D$_2$ Dopamine Receptor Gene in White Nonalcoholics, Less Severe Alcoholics and Severe Alcoholics.

| Group | % Genotype | | | Frequency | | Significance | Odds | |
| --- | --- | --- | --- | --- | --- | --- | --- | --- |
| | B1/B1 | B1/B2 | B2/B2 | B1 | B2 | (Yates) | Ratio | PIC* |
| Nonalcoholics | 0.0(0/30) | 13.3(4/30) | 86.7(26/30) | 0.070 | 0.930 | NS | — | 0.127 |
| Less Severe Alcoholics | 2.8(1.36) | 13.9(5/36) | 83.3(30/36) | 0.097 | 0.903 | $\chi^2 = 7.91$ df = 1 P = 0.005 | 1.30 | 0.167 |
| Severe Alcoholics | 6.1(3/49) | 40.8(20/49) | 53.1(26/49) | 0.265 | 0.735 | $\chi^2 = 7.17$ df = 1 P = 0.008 | 5.75 | 0.352 |

*Polymorphic Information Content. NS = Not significant.

presence of the B1 allele to the absence of this allele is not significantly different in the male combined alcoholics compared to male nonalcoholics $\chi^2=1.26$, df=1, P=0.26). In women, the B1 allele associates with 9 (30.0%) of 30 combined alcoholics but associates with only 2 (11.8%) of 17 nonalcoholics. This difference is also not significant (Pearson $\chi^2=2.01$, df=1, P=0.155). When B1 allelic distributions were compared in alcoholic andnon alcoholic men and women, no significant differences, as expected, are obtained using Yates $\chi^2$ analysis.

Association of the B1 Allele in Blood Samples from Subjects with Family History of Alcoholism The relationship of positive family history of alcoholism (FH$^+$) to the severity of alcoholism was next examined (Table 10). Twenty (66.7%) of 30 nonalcoholics have FH$^+$, 30 (83.3%) of 36 less severe alcoholics have FH$^+$, and 47 (95.9%) of 49 severe alcoholics have FH$^+$. A positive and significant linear trend is found between the presence of FH$^+$ and severity of alcoholism (Mantel-Haenszel Test, $\chi^2$ [Blum et al., 1990]=11.92, P=0.00056).

The prevalence of the B1 allele and its relationship to family history of alcoholism was also determined in the total white sample. 29 (30.1%) of 97 subjects who have FH$^+$, carry the B1 allele. In contrast, only 3 (16.7%) of 18 subjects who have negative family history of alcoholism (FH$^-$) carry the B1 allele. A Yates $\chi^2$ test for independence of allele and family history of alcoholism is not significant ($\chi^2$ [Blum et at., 1990]=0.89, P=344).

When the data were analyzed based on alcoholism severity, interesting differences emerged. In the absence of the B1 allele, a significant linear relationship is found between severity of alcoholism and FH$^+$ (Mantel-Haenszel Test $\chi^2$ [Blum et al., 1990]=12.7, P=0.00036). On the other hand, the relationship of family history of alcoholism and severity of alcoholism is not significant in subjects carrying the B1 allele (Mantel-Haenszel

TABLE 10

TaqI B Alleles of the D$_2$ Dopamine Receptor Gene and Family History of Alcoholism in White Nonalcoholics, Less Severe Alcoholics and Severe Alcoholics

| | *FH$^+$ % Genotype | | | *FH$^-$ % Genotype | | |
| --- | --- | --- | --- | --- | --- | --- |
| Group | B1/B1 | B1/B2 | B2/B2 | B1/B1 | B1/B2 | B2/B2 |
| Nonalcoholics | 0.0(0/20) | 20.0(4/20) | 80.0(16/20) | 0.0(0/10) | 0.0(0/10) | 100(10/10) |
| Less Severe Alcoholics | 3.3(1/30) | 13.3(4/30) | 83.3(25/30) | 0.0(0/6) | 16.7(1/6) | 83.3(5/6) |
| Severe Alcoholics | 6.4(3/47) | 38.3(18/47) | 55.3(26/47) | 0.0(0/2) | 100(2/2) | 0.0(0/2) |

*FH$^+$= positive family history of alcoholism, FH$^-$= negative family history of alcoholism.

Test $\chi^2$=0.05, P=0.81). Thus, when severity of alcoholism is considered, an independent relationship is found between allele and family history of alcoholism.

Association of the B1 Allele in Brain Tissue

Using the insert only of the $\lambda$-hD$_2$G2 fragment of the DRD2 gene, the TaqI digested DNAs from the brains of alcoholic and nonalcoholic subjects underwent two independent hybridizations. The total number of DNAs showing the B1 allele (B1+) was 19 (27.5%); of these DNAs, 13 (68.4%) were from alcoholic subjects, and 6 (31.6%) were from nonalcoholic subjects. Fifty DNAs did not show the B1 allele (B1). Twenty-two (44%) of these DNAs were from alcoholic subjects and 28 (56%) were from nonalcoholic subjects. The ratio of the presence of the B1 allele to the absence of this allele was not significantly different in alcoholic subjects compared with nonalcoholic subjects ($\chi^2$ (Blum et al., 1990)=2.38, p=0.12).

In comparison with the previously described data from blood samples, the lack of correlation here may be due to the lack of division of the subjects into severe alcoholic vs. less severe alcoholic groups.

In terms of race, the B1 allele is associated with 10 (43.5%) of 23 white alcoholics, but is associated with only 3 (13%) of 23 white nonalcoholics. When the proportion of the presence of the B1 allele to the absence of the allele in white alcoholics is compared with white nonalcoholics in the present sample, a significant difference is found ($\chi^2$ [Blum et al., 1990]=3.86, p=0.049).

However, in blacks the B1 allele is associated with 3 (25%) of 12 alcoholics, but is associated with only 3 (27.3%) of 11 nonalcoholics. The proportion of the presence of the B1 allele to the absence of this allele is not significantly different in black alcoholics compared with black nonalcoholics ($\chi^2$ [Blum et al., 1990]=0.02, p=0.09).

Allelic frequencies, in the total sample of 138 alleles, (blacks and whites) were B1 allele, 0.15; and B2 allele, 0.85 in complete agreement with a previous report (Hauge et al., 1991). In the samples of nonalcoholics, B1 and B2 allelic frequencies were 0.10 and 0.90, respectively. The allelic frequencies in the samples of alcoholics were B1, 0.20; and B2, 0.80. The frequency of the B1 allele in samples of nonalcoholics and alcoholics were not significantly different ($\chi^2$ [Blum et al., 1990]=1.82, p=0.18).

When the samples are broken down by race, nonalcoholic whites had the following allelic frequency: B1=0.065; B2=0.93. This contrasts to a higher frequency of the B1 allele in severe white alcoholics: B1=0.25; B2=0.75. The difference between these two groups of whites was statistically significant ($\chi^2$ [Blum et al., 1990]=4.52, p=0.034). Nonalcoholic blacks had a B allelic frequency of B1=0.18; B2=0.82%, and severe black alcoholics had a B allele frequency of B1=0.12%; B2=0.88. Unlike whites, this difference was not statistically significant ($\chi^2$ [Blum et al., 1990]=0.06, p=0.81).

The analysis of blood and brain samples of white severe alcoholics demonstrated that the B1 frequency was 0.24, approximately 2.5 times the frequency found in the combined white nonalcoholic samples. This finding is nonsignificantly less than what we initially observed for A1 frequency in the same severe population which was approximately four times the frequency found in the combined white nonalcoholic samples.

A less robust association of the B1 allele with severe alcoholism was obtained in our deceased subjects (p=0.049) compared to our living subjects (p=0.003). The living subjects were subclassified into three distinct groups compared to the diseased subjects. This subclassification provides a greater degree of discriminating power in the analyses.

Allelic Association with Severity of Alcoholism

Table 11 shows the distribution of TaqI A genotypes in white nonalcoholics and less severe and severe alcoholics. The data on these genotypes were obtained from a previous analysis (Blum et at., 1991) on the same subjects on which the present TaqI B genotypes (Table 9) were determined.

The A1 allele associates with: 6 (20.0%) of 30 nonalcoholics, 11 (30.8%) of 36 less severe alcoholics and 29 (59.2%) of 49 severe alcoholics. The proportion of the presence of the A1 allele to the absence of this allele is significantly different between nonalcoholics and severe alcoholics, and between less severe and severe alcoholics (Table 11). However, no significant differences in A1 and A2 alleles are found between nonalcoholics and less severe alcoholics.

Using the McNemare Test (Seigel, 1956), a comparison was made between TaqI B (Table 9) and TaqI A (Table 11) alleles in the three groups of white subjects. No significant differences are found in the association of these two polymorphisms with nonalcoholics (P=0.50) or less severe alcoholics (P=0.063). However, a significant difference (P=0.03) is observed in TaqI A and TaqI B alleles when comparisons are made for their association with the severe alcoholic group. Since the inventors have found a significant association of family history of alcoholism and severity of alcoholism and this association was maintained when comparisons were made between nonalcoholics and severe alcoholics ($\chi^2$=10.2, P=0.0014), they decided to include family history of alcoholism as well as allelic type in subsequent stepwise logistic regression analyses. Moreover using stepwise logistic regression analysis (Table 12), two significant variables selected as being associated with severity of alcoholism are a family history of alcoholism and the A1 allele. As seen in Table 12, family history of alcoholism (improvement of $\chi^2$=12.4, P<0.001) and the A1 allele (improvement of $\chi^2$=9.9, P=0.002) seem to be independently associated with severity of alcoholism.

TABLE 11

TaqI A Alleles of the $D_2$ Dopamine Receptor Gene in White Nonalcoholics, Less Severe Alcoholics and Severe Alcoholics

| Group | % Genotype | | | % Frequency | | Significance | Odds | |
|---|---|---|---|---|---|---|---|---|
| | A1/A1 | A1/A2 | A2/A2 | A1 | A2 | (Yates) | Ratio | PIC* |
| Nonalcoholics | 0.0(0/30) | 20.0(6/30) | 80.0(24/30) | 0.100 | 0.900 | NS | — | 0.172 |
| Less Severe Alcoholics | 0.0(0/36) | 30.6(11/36) | 69.4(25/36) | 0.153 | 0.847 | $x^2 = 10.0$ df + 1 P = 0.001 | 1.76 | 0.242 |
| Severe Alcoholics | 6.1(3/49) | 53.1(26/49) | 40.8(20/49) | 0.327 | 0.673 | $x^2 = 5.72$ df = 1 P = 0.017 | 5.80 | 0.393 |

*Polymorphic Information Content.
NS = Not significant.

TABLE 12

Stepwise Logistic Regression Analysis for Modeling Associations with Both A1 and B1 Alleles and Family History of Alcoholism of the DRD2 Gene Omitting the Less Severe Group

| Step No. | Term Entered | df | Improvement | |
|---|---|---|---|---|
| | | | $x^2$ | P Value |
| 0 | — | — | — | — |
| 1 | FH[a] | 1 | 12.4 | <.001 |
| 2 | A1[b] | 1 | 9.9 | <.002 |

| Model | Logistic Regression Coefficient | Odds Ratio | 95% Confidence |
|---|---|---|---|
| FH | 2.42 | 11.2 | 1.97–63.9 |
| A1 | 1.72 | 5.6 | 1.74–18.0 |

TABLE 12-continued

Stepwise Logistic Regression Analysis for Modeling Associations
with Both A1 and B1 Alleles and Family History of Alcoholism of
the DRD2 Gene Omitting the Less Severe Group

| K | 2.23 | 0.107 | .019–0.60 |

[a]FH= family history of alcoholism.
[b]A1= the TaqI A1 RFLP of the $D_2$ dopamine receptor gene.

In constructing a genetic linkage map based on RFLPs, Boststein et al (Botstein et al., 1980) have estimated the Polymorphic Information Content (PIC), a measure of the probability that informative alleles are segregating in a family. The more informative a locus is, the greater the map distance at which linkage with a second locus can be reliably estimated. According to Schumm et al., (1988), loci with higher PIC values are informative in a greater fraction of families. In the present study (see Tables 9 and 11 ), the PIC for the A1 allele and B1 allele, respectively, is 0.15 and 0.12 in nonalcoholics, 0.24 and 0.17 in less severe alcoholics and 0.39 and 0.35 in severe alcoholics. Hauge et al., (1991) estimated the PIC for the A1 allele and B1 allele, respectively, to be 0.30 and 0.23 in unclassified general population subjects. A plausible explanation for the apparent discrepancy between the Hauge et al (1991) and the present study is that the former made no attempt at excluding alcohol or other drug problems from their subject population. Still, the present results of enhanced PIC with increasing severity of alcoholism are consistent with polymorphic sites at either the 5' or 3' end of the DRD2 gene.

In summary, the present example shows that the prevalence of the A1 and B1 alleles of the DRD2 gene is strongly associated with severe alcoholism.

D2 Dopamine Receptor Binding Characteristics in Caudates of Alcoholic and Nonalcoholic Subjects The binding characteristics of the $D_2$ dopamine receptor was determined in 66 brains of alcoholic and nonalcoholic subjects. In a blinded experiment, the binding characteristics ($K_d$ [binding affinity] and $B_{max}$ [number of binding sites]) of the $D_2$ dopamine receptor were determined in the caudate nuclei of these brains using tritiated spiperone as the ligand. The adjusted $K_d$ was significantly lower in alcoholic than in nonalcoholic subjects. In subjects with the B1 allele, in whom a high association with alcoholism was found, the $B_{max}$ was significantly reduced compared with the $B_{max}$ of subjects with the B2 allele. Moreover, a progressively reduced $B_{max}$ was found in subjects with B2/B2, B1/B2 and B1/B1 alleles, with subjects with B1/B2 having the highest mean values, and subjects with B1/B1, the lowest.

Brain Samples

Tissue from 33 alcoholic and 33 nonalcoholic subjects was obtained from the National Neurological Research Bank at the Wadsworth Veterans Affairs Medical Center, Los Angeles, Calif. The frontal gray cortex and caudate nucleus of each subject were removed from the brain at autopsy by a neuropathologist and immediately frozen at $-70°$ C. until used. The brains analyzed consisted of the 70 that were previously studied (Blum et al., 1990); four caudate nuclei were unavailable. The ages (mean±SEM) of the alcoholic and nonalcoholic subjects, respectively, were 50.4±2.3 years and 53.2±2.6 years. The alcoholic subjects included 21 whites and 12 blacks, and there were 24 whim and nine black nonalcoholic subjects. The alcoholic subjects included 30 males and three females, and there were 29 male and four female nonalcoholic subjects. The autolysis times of the alcoholic and nonalcoholic subjects' brain samples were 23.0±1.5 hr. and 22.6±1.7 hr., respectively. Diagnoses of alcoholism were made independently by two trained psychiatrists using DSM-III-R criteria of alcohol dependence and abuse through examination of medical and autopsy records, interviews of treatment center personnel and relatives, and alcohol consumption data. These two assessments were 100% concordant in diagnosing alcoholic and nonalcoholic subjects. Examination of medical records and/or results of analysis of body fluids at autopsy did not indicate that any of the subjects had used neuroleptic agents. The causes of death included accidents, gunshot wounds, myocardia infarction, heart failure, cancer, gastrointestinal bleeding, suicide, and pneumonia. Informed consent was obtained from next of kin to perform this study.

D2 Dopamine Receptor Assay and Statistical Analysis

The receptor assays and statistical analysis of the data were performed as described under Example I of this specification.

Binding characteristics of the D2 Dopamine Receptor Gene as a Function of Alcoholism and Allele Tables 13 and 14 provide the binding characteristics of the D2 receptor as a function of alcoholism and allele(s) in whites and blacks. In whites, the TaqI B1 RFLP shows no significant differences with regard to unadjusted $K_d$, pmol/l, however, the number of binding sites ($B_{max}$, fmol/mg of protein) was found to be lower in B1[+] allelic subjects compared to B1[−] allelic carriers. This finding was independent of alcoholism. As originally found with the TaqA1 RFLP in blacks, no differences were found with the TaqB1 RFLP. Similar findings were obtained where race is not subclassified (Table 15).

TABLE 13

Binding Characteristics of the $D_2$ Dopamine Receptor Gene as a
Function of Alcoholism and Allele in White Subjects

| | White Alcoholics (n = 21) | | White Nonalcoholics (n = 22) |
|---|---|---|---|
| $K_3$, pmol/l | | | |
| Unadjusted | 74.4 ± 6.5 | p = 0.01 | 107.1 ± 9.7 |
| Log $K_d$ | | p = .084 | |

TABLE 13-continued

Binding Characteristics of the $D_2$ Dopamine Receptor Gene as a Function of Alcoholism and Allele in White Subjects

| $B_{max}$ fmol/mg protein | | | | | | |
|---|---|---|---|---|---|---|
| Unadjusted | 61.99 ± 6.8 | p = 4.26 | 80.27 ± 7.5 | | | |
| Adjusted | 74.92 | | 67.92 | | | |

| | Whites | | | | | |
|---|---|---|---|---|---|---|
| | A1+ (n = 18) | | A1− (n = 25) | B1+ (n = 12) | | B1− (n = 31) |
| $K_d$ pmol/l | | | | | | |
| Unadjusted | 72.8 ± 7.0 | p = 0.01 | 104.4 ± 8.9 | 76.9 ± 9.4 | p = NS | 96.7 ± 7.9 |
| Covariate | | | | | | |
| Adjusted Log $K_d$ | 4.40 | p = .873 | 4.42 | 4.42 | p = .915 | 4.41 |
| $B_{max}$, fmol/mg Protein | | | | | | |
| Unadjusted | 53.12 ± 4.2 | p = 0.001 | 84.5 ± 7.2 | 52.6 ± 4.5 | p = 0.002 | 78.6 ± 6.4 |
| Adjusted | 56.68 | p = .007 | 81.9 | 59.41 | p = .067 | 76.51 |

TABLE 14

Binding Characteristics of the $D_2$ Dopamine Receptor Gene as a Function of Alcoholism and Allele in Black Subjects

| | Black Alcoholics (n = 12) | | Black Nonalcoholics (n = 9) |
|---|---|---|---|
| $K_d$, pmol/l | | | |
| Unadjusted | 65.2 ± 8.6 | | 68.2 ± 6.6 |
| Log $K_d$ | 4.05 | | 42.7 |
| | | p = .067 | |
| $B_{max}$ fmol/mg protein | | | |
| Unadjusted | 58.9 ± 10.4 | | 50.9 ± 9.7 |
| | | p = .116 | |
| Adjusted | 62.36 | | 46.23 |

| | Blacks | | | | | |
|---|---|---|---|---|---|---|
| | A1+ (n = 11) | | A1− (n = 10) | B1+ (n = 5) | | B1− (n = 16) |
| $K_d$, pmol/l | | | | | | |
| Unadjusted | 68.6 ± 8.9 | | 64.2 ± 6.8 | 68.6 ± 14.8 | | 6.58 ± 6.0 |
| | | p = .283 | | | p = .398 | |
| Covariate | | | | | | |
| Adjusted Log $K_d$ | 4.20 | | 4.08 | 4.21 | | 4.12 |
| | | p = .NS | | | p = NS | |
| $B_{max}$, fmol/mg Protein | | | | | | |
| Unadjusted | 57.3 ± 11.8 | | 53.5 ± 8.1 | 48.6 ± 18.3 | | 57.6 ± 7.7 |
| | | p = .329 | | | p = .329 | |
| Adjusted | 47.51 | | 57.93 | 47.94 | | 57.93 |
| | | p = NS | | | p = NS | |

TABLE 15

Binding Characteristics of the $D_2$ Dopamine Receptor as a Function of Alcoholism and Allele

| | Alcoholic Subjects (n = 33) | | Nonalcoholic Subjects (n = 31) |
|---|---|---|---|
| $K_d$, pmol/l | | | |
| Unadjusted | 71.0 ± 5.2 | p = .02 | 95.8 ± 7.8 |
| Covariate adjusted | | | |
| Log $K_d$ | 4.21 | p = .02 | 4.43 |
| $B_{max}$ fmol/mg protein | | | |
| Unadjusted | 60.9 ± 5.7 | p = .174 | 71.8 ± 6.2 |
| Adjusted | 70.83 | | 61.12 |

| | $D_2$ Dopamine Receptor Allele | | | |
|---|---|---|---|---|
| | A1+ (n = 29) | A1− (n = 35) | B1+ (n = 18) | B1− (n = 46) |
| $K_d$, pmol/l | | | | |
| Unadjusted | 71.2 ± 5.4 | 92.9 ± 7.3 | 72.9 ± 7.5 | 87.0 ± 6.0 |
| | | p = .02 | | p = NS |
| Covariate Adjusted | | | | |
| Log $K_d$ | 4.34 | 4.30 | 4.30 | 4.37 |
| | | p = .676 | | p = .501 |
| $B_{max}$ fmol/mg Protein | | | | |
| Unadjusted | 54.7 ± 5.1 | 75.6 ± 6.1 | 51.5 ± 5.6 | 72.0 ± 5.2 |
| | | p = 0.01 | | p = .01 |
| Adjusted | 57.25 | 73.49 | 55.97 | 70.10 |
| | | p = .024 | | p = .044 |

Compared to the TaqA1 RFLP, the TaqI B1 RFLP shows a similar result in terms of binding characteristics of the dopamine D2 receptor. This is not surprising since these two polymorphic loci are in disequilibrium linkage as determined previously (Hauge et at., 1991).

Lack of Association Between the D1 Receptor Gene and Alcoholism

The brain tissue tested for the B1 and A1 alleles of the DRD2 receptor were also tested for an allele in the DRD1 receptor as described (Sunahara et at., 1990). The RFLP is seen in an EcoRI digest using a G36 probe (Sunahara et at., 1990); two DNA. fragments of 10.5 kb and 6.8 kb are detected.

There is no association of the D1 receptor gene with alcoholism as well as no significant effect on dopamine D1 receptor binding characteristics in both nonalcoholics and alcoholics in caudate tissue (Table 16).

This lack of association of alcoholism with the D1 receptor allele further demonstrates the specificity of the DRD2 allelic associations.

TABLE 16

Binding Characteristics of the D1 Dopamine Receptor as a Function of Alcoholism and Allele

| | Alcoholic Subjects (n = 27) | | Nonalcoholic Subjects (n = 23) |
|---|---|---|---|
| $K_d$, pmol/l | | | |
| Unadjusted Covariate adjusted | 761 ± 35 | | 738 ± 44 |
| Log $K_d$ | 6.61 | p = .516 | 6.57 |
| $B_{max}$ fmol/mg protein | | | |
| Unadjusted Adjusted | 83.9 ± 6.7 | p = .54 | 90.2 ± 6.0 |

| | $D_1$ Dopamine Receptor Allele | |
|---|---|---|
| | A1+ (n = 16) | A1− (n = 34) |
| $K_d$, pmol/l | | |
| Unadjusted Covariate | 819 ± 58 | 718 ± 29 |
| Adjusted Log $K_d$ | 6.67 | 6.55 |
| | p = 1.02 | |
| $B_{max}$, fmol/mg Protein | | |
| Unadjusted | 955 ± 8.3 | 82.7 ± 5.3 |

TABLE 16-continued

Binding Characteristics of the D1 Dopamine Receptor as a Function of Alcoholism and Allele Adjusted  p = .208

EXAMPLE 3

Association of DRD2$^{IN6-EX7}$ Allele Haplotype I with Alcoholism

An association between possession of the dopamine D$_2$ receptor A1 RFLP allele and lowered spiperone binding density in the caudate among controls and severe alcoholism was described in Example 1 (Noble et al., 1991). This report provided a pivotal theoretical basis for evaluating studies reporting linkage disequilibrium between the D$_2$A1 allele and receptor variants associated with heightened risks for substance abuse and a range of other neuropsychiatric and neurological disorders (Comings et al., 1991). Because the D$_2$ TaqA RFLP is located downstream from the carboxy terminal codon, the present inventors sought to correlate DNA polymorphisms located internal to the coding sequences at this locus to alcoholism. Polymorphisms located within the coding sequences may be more tightly associated with physiologically relevant receptor gene variants. One such variant, the DRD$_2$$^{In6-Ex7}$ haplotype is composed of two polymorphisms that are separated by 212 bp and span the juncture of the intron-6 (at position 3208) and exon-7 (at position 3420) sequences (Sarkar et al., 1991). The two polymorphisms are each characterized by two single base change polymorphisms, a T or G at position 3208 (GAGGGTGAAAG [SEQ ID NO: 1]) and (GAGGGG-GAAAG [SEQ ID NO:2]); and a T or C at position 3420 (CACCATGGTCT [SEQ ID NO:4]) and (CACCACGGTCT [SEQ ID NO:3]), providing four possible haplotypes, designated I, II, III, and IV. Haplotype I is defined as having a T at position 3208 and a C at position 3420. Among North American whites and blacks the DRD$_2$$^{In6-Ex7}$ III haplotype is very rare.

PCR™ amplification of specific alleles (PASA) is a modification of PCR™ in which specific alleles are selectively amplified by the use of precisely matched primers (Sarkar et al., 1991). Characterization of parameters affecting PASA reveal that primers mismatched within two bases of their 3' end can unequivocally distinguish two alleles after agarose gel electrophoresis (Sarkar et al., 1991). If the desired allele is present, an abundance of the amplified segment is seen with the allele-specific primer, while no amplified segment is seen if the other allele is present.

Oligonucleotide primers were synthesized in an Applied Biosystems DNA Synthesizer (Foster City, Calif.). Ampli-Taq® DNA Polymerase was purchased from Perkin-Elmer Cetus (Norwalk, Conn.). PCR™ was performed in a Perkin-Elmer DNA Thermal Cycler.

PASA was carried out essentially as described (Sarkar et al., 1991). Briefly, a 20-µl total volume of the reaction mixture contained the following: 10 mM Tris-HCl pH 8.3, 0.1 µM of each PCR™ primer, 50 mM KCl, 1.5 mM MgCl$_2$, 100 ng of genomic DNA, 5% formamide and 0.5 U of the AmpliTaq®. Thirty cycles of PCR™ were performed for 1 min at 94° C., 2 min at 50° C. and 3 min at 72° C. Five microliters of each amplification were separated by electrophoresis through a 3% agarose gel.

Haplotype I is selectively amplified using the #3208 primer GAGTCTTCAGAGGGT (SEQ ID NO:5) and the #3420 primer TGCTGTGGAGACCG (SEQ ID NO:6). The 5' base of primer 3208 begins in intron 6 at the base number 3193. The oligonucleotide is a 15-mer and is oriented downstream of the direction of transcription for the dopamine D$_2$ receptor. Its specificity is imparted by T at its 3' end. Primer 3420 begins in exon 7 at base 3433. It is a 14-mer and oriented upstream of transcription. Its specificity is imparted by G at its 3' end. The amplified product has a size of 241 bp (3433–3193+1).

The present example cites the relationship between DRD$_2$$^{In6-Ex7}$ haplotype status and spiperone B$_{max}$ and K$_d$ binding properties in caudate autopsy samples from 31 alcoholic and 33 non-alcoholic cases. In the nonalcoholic sample those cases carrying the I haplotype had lower B$_{max}$ (p=0.03), while the IV haplotype had elevated K$_4$ (binding affinity) (p=0.05) and log (K$_d$) (p=0.03). As shown in FIG. 10, the variance in the K$_d$ between IV/non-IV samples was largely accounted for by the II–IV haplotype cases. The % prevalence of the haplotype I is 39.4% in alcoholics as compared to 16.1% in the controls. The prevalence of the I haplotype was higher by $\chi^2$ analysis (p=0.04) and the IV haplotype was lower (p=0.1) in the alcoholic samples than in the nonalcoholic samples, but no haplotype differences were observed for B$_{max}$ or K$_d$ in the alcoholic samples. When the analysis was limited to whites, the respective $\chi^2$ values were significant for I (p=0.02) and IV (p=0.007). Thus PCR™ (PASA) may be used to detect dopamine receptor alleles predictive of susceptibility to compulsive disorders. The selection of primers may be varied to locate desired alleles.

EXAMPLE 4

Allelic Association of the D$_2$ Dopamine Receptor Gene with Cocaine Dependence A major determinant in cocaine's liability for abuse in humans is its ability to reinforce self-administration by producing euphoria or pleasure (Gawin and Ellinwood, 1989). Cocaine is a highly efficacious reinforcer being self-administered by humans and animals, its maintenance of responding occurs regardless of cocaine's route of delivery (for review see Clouet et al., 1988). The specificity of cocaine's reinforcing properties in the brain are localized in the mesolimbic/mesocortical dopamine reward system (Scale and Carney, 1991; Ettenberg et al., 1982; Goeders et al., 1985; Wise, 1987; Koob, 1987; Bain and Kornetsky, 1987; Dworkin and Smith, 1988).

Cocaine has been found to bind to specific recognition sites associated with the dopamine (DA) transporter system (Kennedy and Hanbauer, 1983; Ritz et al., 1987; Madras et al., 1989) and to inhibit the uptake of dopamine into presynaptic terminals (Heikkila et al., 1975; Koe, 1976; Reith et al., 1986; Boja and Kuhar, 1989; Izenwasser et al., 1990). These neurochemical actions have been implicated in many of the effects of cocaine (Ritz et al., 1987; Bergman et al., 1989; Spealman et al., 1989; Kleven et al., 1990; Witkin et al., 1991). While the uptake of norepinephrine and serotonin are also inhibited by cocaine (Koe, 1976; Reith et al., 1976), selective uptake inhibitors of these neurotransmitters generally fail in themselves to influence self-administration of cocaine (Kleven et al., 1990; Witkin et al., 1991 ).

The inhibition of DA reuptake in the synapse results in accumulation of high concentrations of this neurotransmitter (Hurd et al., 1988; Pettit and Justice, 1989) which consequently induces DA neurotransmission (Hurd and Understedt, 1989). The activation of DA receptors (subtypes $D_1$ and $D_2$ are most prevalent) is an important neurochemical step in the events that mediate the rewarding effects of cocaine (Colpaert et al., 1979; McKenna and Ho, 1980; Woolverton and Kleven, 1988).

Bunzow et al (Bunzow et al., 1988) have cloned and expressed rat DRD2 complementary DNA (cDNA). Using this rat cDNA, Grandy et al., (1989; 1989) described the cloning and chromosomal mapping of a human DRD2 gene on 11q22-q23. They also found at this locus a two-allele (A1 and A2) TaqI RFLP, with a minor allele (A1) frequency of 0.24, corresponding to a PIC of 0.30. This RFLP was detected with the genomic phage clone $\lambda$-$hD_2G1$ (ATCC #61354 and 61355) which contains exon 8 and the 3' untranslated portion of the DRD2 gene. In an attempt to increase the PIC of the DRD2 locus, Hauge et al., (1991) used additional phage and cosmid clones in the vicinity of the DRD2. A new two-allele (B1 and B2) TaqI RFLP, with a minor allele (B1) frequency of 0.16, as well as a TG microsatellite polymorphism with a PIC of 0.62 were found. The TaqIB site was found to be located 5' of the first coding exon of the DRD2 gene and the microsatellite was localized in the intron separating coding exons 2 and 3. Furthermore, Hauge et al., (1991) found strong linkage disequilibrium between TaqIA and TaqIB RFLPs (in contrast these RFLPs were in linkage equilibrium with the microsatellite polymorphism), yielding a highly informative compound marker locus with PIC of 0.76.

An aspect of the present invention is the association of a human dopamine $D_2$ receptor gene A1 and B1 allele presence individually and together in the DNA of an individual as determining the genetic predisposition to cocaine dependence. The present example describes studies that examine allelic association of the $D_2$ dopamine receptor (DRD2) gene with cocaine dependence and determine, in cocaine dependent subjects, the relationship of DRD2 alleles to family history and behavioral parameters.

Selection of Study Group Subjects

The study group consisted of 53 white (non hispanic) males who applied voluntarily for treatment of their cocaine problem at a medical center associated with a hospital. This group was part of a larger sample, that also included hispanics and blacks, who had been initially selected for a prospective treatment evaluation study. The selection of the sample, precluded, through a hospital triage system, patients with a history of psychiatric treatment. All patients selected fulfilled the diagnosis of cocaine dependence (DSM-III-R criteria [American Psychiatric Association; 1987]) and a majority were patients seeking aid, for the first time, for their cocaine problem. Institutional Review Board approval was obtained for this project,-and informed consent was signed by the patients after the nature of the procedures and maintenance of confidentiality were explained to them.

Procedures for Data Collection

Psychological, environmental and sociocultural variables, related to the initiation and maintenance of cocaine and other drug dependence, were examined using a natural history approach (Winick, 1962). Specially designed interview schedules were used to collect sociodemographic data, developmental, social functioning and psychiatric information. In particular, data on deviant behaviors and family history of substance use were obtained. Moreover, a complete personal substance use history, with particular emphasis on cocaine use behaviors was gathered from each subject following a strategy developed (Nurco et al., 1975) and derailed elsewhere (McGlothlin et al., 1977; Anglin and McGlothlin, 1984). Briefly, a schematic time chart was prepared from official records before each intake interview, showing all arrests, intervals of incarceration, legal supervision and treatment episodes. Trained interviewers then established, with subject cooperation, the date of first cocaine use and first regular cocaine use on the time chart as well as dates for other critical life events. More detailed information on cocaine-related behaviors was subsequently collected 12-months before first cocaine use up to the time of interview (treatment entry).

From this extensive data, four sets of variables were selected for this study. Demographic variables include: age at interview, number of years in school, marital status (ever married) and annual income in the year before initial treatment entry. Three sets of variables, which previous research has shown to bear on the risk for substance use behaviors (Cadoret et al., 1986; Piekens et al., 1991; Anglin and McGlothlin, 1984), were also obtained. These sets are shown in Table 17 and include: family history of substance use, deviant behaviors (before and after regular cocaine use) and substance use characteristics with emphasis on cocaine.

Parameters of Family History of Substance Use, Deviant Behaviors and Substance Use Characteristics of Cocaine Dependent Subjects

| Family History of Substance Use | Substance Use Characteristics |
|---|---|
| Father has alcohol problem | Age 1st cocaine use |
| Mother has alcohol problem | Age 1st regular cocaine use |
| Father is alcoholic | Age 1st regular other stimulant use |
| Mother is alcoholic | Age 1st regular marijuana use |
| At least one parent alcoholic | Age 1st regular sedative/hypnotic use |
| Siblings have alcohol problem | Age 1st alcohol use |
| Siblings have drug problem | No. yrs. from 1st alcohol use up to treatment entry |
| Father, mother and siblings all have alcohol problem | Total ozs. Alcohol consumed up to treatment entry |
| Family members (father, mother, siblings) with any alcohol problem | DSM-III-R alcohol dependence criteria score (<3, $\geq$3) |
| Family members with any drug problem | |

| Deviant Behaviors | Substance Use Characteristics, Cont. |
|---|---|
| Run away | No. weeks from 1st cocaine use to next cocaine use |
| Expelled/suspended from school | No. mos. from 1st cocaine use up to 1st severe use |
| Drunk/high in school | No. mos. from 1st severe cocaine use up to treatment entry |
| Drive while high/drunk | No. mos. from 1st cocaine use up to treatment entry |
| Damage school property | No. gms. cocaine used from 1st severe use up to treatment entry |
| Threaten an adult while a minor | No. gms. cocaine used 12 mos. before treatment entry |
| Hit an adult while a minor | Mean % time using intranasal cocaine |
| Damage other's property | Mean % time using free base cocaine |
| Conning/fraud | Mean % time using i.v. cocaine |
| Steal from wallet/purse | Mean % time using "crack" cocaine |
| Steal from store | Mean % time using i.v., free |

-continued

Parameters of Family History of Substance Use, Deviant
Behaviors and Substance Use Characteristics of
Cocaine Dependent Subjects

| | base, and "crack" cocaine |
|---|---|
| Steal from family | Mean % time using cocaine from 1st severe use up to treatment entry |
| Steal from school | |
| Grab a purse | Mean % time involved in criminal activity from 1st cocaine use up to treatment entry |
| Carry drugs for others | Mean % time involved in criminal activity from 1st severe cocaine use up to treatment entry |
| Buy stolen goods | Mean % time working from 1st cocaine use up to treatment entry |
| Sell/fence stolen goods | Mean % time working from 1st severe cocaine use up to treatment entry |
| Break into a car | Ever used "crack" cocaine |
| Break into a building | |
| Prostitution/pimping | |
| Gambling | |
| Threaten for profit | |
| Use force for profit | |
| Carry a weapon | |
| Threaten with a weapon | |
| Use weapon for profit | |
| Forge prescriptions | |
| Forge fictitious checks/steal credit cards | |
| Sell drugs | |
| Steal a car | |
| Beat someone severely | |
| Rape | |
| Shot someone | |

Genotyping of Study Subjects

High molecular weight genomic DNA was extracted from whole blood according to the procedures described by Maniatis et al., (1982). The DNA probe, as previously used (Blum et al., 1992), was a 1.73-kilobase (kb) band obtained from a BamHI digest of a human genomic fragment $\lambda$-hD$_2$G1 (ATCC #61354 and 61355) shown in FIG. 3. The fragment includes, in part, the coding sequence of the last exon containing the seventh transmembrane domain of the DRD2 gene and part of the 16.5 kb of the 3' flanking sequence (Grandy et al., 1989; Grandy et al., 1989). The 1.73-kb probe was labeled using random-priming with phosphorous 32 deoxycytidine triphosphate (Maniatis et al., 1982) to a specific activity of $1 \times 10^9$ cpm/$\mu$g. The DNA samples after digestion with TaqI were hybridized with the labeled probe as previously described (Blum et al., 1992), to reveal the A1 and A2 alleles. The identifying band in individuals carrying the allele A1 is the 6.6 kb band and the allele A2 is the 3.7±2.9 kb bands.

Employing similar techniques as described above, and given in detail in previous reports (Grandy et al., 1989; Hauge et al., 1991), a 3.7-kb BamHI fragment of $\lambda$-hD$_2$G2, shown in FIG. 13, (located 5' of the first coding exon of the DRD2 gene), was isolated and hybridized with TaqI digests of DNA. Two alleles were identified with this probe; a 4.6-Kb B1 allele and a 4.1-kb B2 allele.

Statistical Analysis

The difference in the prevalence of the A1(A2) and B1(B2) alleles between cocaine-dependent subjects and control groups was tested using Yates Chi-square analysis (Seigel, 1956). Moreover, to evaluate allelic association, the dam, compiled on numerous parameters of family history of substance use, deviant behaviors and substance use characteristics in cocaine-dependent subjects, were subjected to Chi-square analysis when the measures were nominal and to separate variance two sample t-test when the measures were continuous. Furthermore, composite measures were also obtained by combining a priori classification of related areas of family history of substance use, deviant behaviors and substance use characteristics and were analyzed for association with the A1 allele by using Chi-square or one-tailed separate variance t-test where appropriate. These classifications as indicated earlier are based on previous predictors of severe substance use problems.

When the distribution of the continuous measure was non-normal, a mathematical transformation was applied which re-expressed the measure as Gaussian (Sokal and Rohlf, 1969). In distributions of proportions and/or percentages, we used an Arcsine transformation, which is also known as the Angular Transformation, to provide independence of means and variance.

In an effort to verify that individual statistical relationships are due to other than chance, and simultaneously to identify behavioral and substance use parameters that may be important for distinguishing between the A1 and A2 alleles, a stepwise logistic regression procedure (Dixon, 1990) was employed. Parameters were included into the stepwise logistic regression analysis if they approached significance when individually tested for allelic differences or if there was strong a priori justification for their inclusion. Additionally, selection criteria included only those parameters which allowed us to maximize the sample size and thus provide a stronger statistical power. BMDP default P values for stepwise entry (P=0.15) and removal (P=0.20) of predictors into the logistic model were retained (Dixon, 1990). Logistic regression coefficients and their standard errors, plus odds ratios and their confidence intervals were computed according to the methodology of Hosmer and Lemeshow (Hosmer and Lemeshow, 1989) as implemented in the BMDP statistical computer program (Dixon, 1990). Cases which were missing information for any of the parameters tested were excluded from the analysis. Thus, the final stepwise logistic regression analysis in this study was based on a subset of 49 cases. Therefore, inferences or estimates made from these subsets must be approached with caution.

Sensitivity, specificity and predictive values were then obtained from each variable in the logistic model. Sensitivity is defined as the incidence of true positive results obtained when applied to sample subjects known to have the A1 allele. Specificity is defined as the incidence of true negative results obtained when applied to sample subjects known to have the A2 allele (Galen and Gambino, 1975). Receiver-operating characteristic (ROC) curves were constructed for the presence or absence of the A1 allele from measures selected for the logistic model. The ROC curves display the continuum of both true-positive fraction (TPF) and false-positive fraction (FPF) values. False positive values occur when the model predicts the A1 allele when in fact the sample subject has the A2 allele. Conventionally, a ROC curve plots TPF (sensitivity) on the y axis as a function of FPF, which is the complement of the true negative value (1-specificity) on the x axis. The area under the curve is a summary of the test's accuracy; the larger the area, the better the test. Utilizing the ROCFIT computer program (Metz, 1978), a maximum likelihood estimate was obtained from the area under the curve and its confidence limits.

Genotypic Distribution of TaqIA DRD2 Alleles

The demographic characteristics of the sample of cocaine dependent subjects (average±SEM) were as follows: age 35.1±0.8 yrs (n=53), education 12.6±0.2 yrs (n=53), and annual income $19,500±3,200 (n=51); 30.2% of the sample (n=53) was ever married.

Table 18 gives the genotypic distribution of TaqIA DRD2 alleles in white cocaine dependent subjects and in three white control groups. Of the 53 cocaine dependent subjects, 27 (50.9%) had the A1 allele. In a sample of 54 non-substance abusing subjects previously studied in the inventors' laboratory (Blum et al., 1990; Blum et al., 1992), 10 (18.5%) had the A1 allele. The difference between these two groups, in the proportion of the presence and absence of the A1 allele, was statistically significant (P=0.0013; odds ratio=4.36). In a combined sample of 100 non-substance abusing controls, which included samples from two studies conducted by the present inventors (Blum et al., 1990; Blum et al., 1992) and that of two others (Parsian et al., 1991; Comings et al., 1991), 16 (16.0%) carried the A1 allele. The difference between this group and the cocaine dependent group was also statistically significant (P=$10^{-5}$; odds ratio=5.45). In a larger control group of 365 subjects which included the above 100 subjects and 265 individuals of four studies (Grandy et al., 1989; Comings et al., 1991; Bolos et al., 1990; Gelernter et al., 1991) derived from the general population (substance abusers not excluded), 98 (26.8%) had the A1 allele. The difference between this control group and the cocaine dependent group, in the proportion of the presence and absence of the A1 allele, was also statistically different (P=0.0006; odds ratio=2.83).

A1 Allelic Presence in Cocaine Dependent Subjects with and without Comorbid Alcohol Dependence Since a significant number of cocaine dependent subjects in the present example were also alcohol dependent (as defined by DSM-III-R criteria [American Psychiatric Association]), A1 allelic presence was compared in cocaine dependent subjects with and without comorbid alcohol dependence (Table 19). The results showed that 19 (51.4%) of 37 cocaine dependent subjects with coexisting alcohol dependence had the A1 allele, while 8 (50.0%) of 16 cocaine dependent subjects without alcohol dependence carried the A1 allele. The difference between these two groups in the proportion of the presence and absence of the A1 allele was not significantly different (P=0.835; odds ratio=0.947), indicating that the

TABLE 18

Genotype Distribution of TaqIA DRD2 Alleles in White Cocaine Dependent Subjects and Controls

| Group | N | % Genotype A1/A1 | % Genotype A1/A2 | % Genotype A2/A2 | Significance[a] (Yates) | Odds Ratio |
|---|---|---|---|---|---|---|
| Cocaine dependent subjects | 53 | 5.7 (3/53) | 45.3 (24.53) | 49.1 (26/53) | — | — |
| Non-substance abusing controls[1] | 54 | 0 | 18.5 (10/54) | 81.5 (44/54) | $\chi^2$ = 10.2; df = 1; P = 0.0013 | 4.36 |
| Non-substance abusing controls[2] | 100 | 0 | 16.0 (16/100) | 84.0 (84/100) | $\chi^2$ = 19.3; df = 1; P = $10^{-5}$ | 5.45 |
| Non-substance abusing and general population controls[3] | 365 | 2.5 (9/365) | 24.4 (89/365) | 73.2 (267/365) | $\chi^2$ = 11.6; df = 1; P = 0.0006 | 2.83 |

[a]Comparisons with cocaine dependent subjects for the presence or absence of the A1 allele.
[1]Blum et al., 1990, Blum et al., 1992.
[2]Blum et al., 1990, Parsian et al., 1991, Blum et al., 1992, Comings et al., 1991.
[3]Grandy et al., 1989, Blum et al., 1990, Bolos et al., 1990, Parsian et al., 1991, Blum et al., 1992, Comings et al., 1991, Gelernter et al., 1991.

TABLE 19

Genotypic Distribution of TaqIA DRD2 Alleles in Cocaine Dependent Subjects With and Without Comorbid Alcohol Dependence

| Group | N | % Genotype A1/A1 | % Genotype A1/A2 | % Genotype A2/A2 | Significance[a] (Yates) | Odds Ratio |
|---|---|---|---|---|---|---|
| Cocaine dependent subjects without alcohol dependence | 16 | 6.3 (1/16) | 43.8 (7/16) | 50.0 (8/16) | — | — |
| Cocaine dependent subjects with alcohol dependence | 37 | 5.4 (2/37) | 45.9 (17/37) | 48.6 (18/37) | $\chi^2$ = 0.04; df = 1; P = 0.835 | 0.947 |

[a]Comparisons with cocaine dependent subjects for the presence or absence of the A1 allele.

higher prevalence of the A1 allele found in cocaine dependent subjects, compared to controls, is not due to the contribution of comorbid alcohol dependence.

Genotypic Distribution of TaqIB DRD2 Alleles

Table 20 presents the genotypic distribution of TaqIB DRD2 alleles in the same group (less one) of white cocaine subjects and white non-substance abusing controls (less one) as shown in Table 18. Of the 52 cocaine dependent subjects analyzed, 20 (38.5%) had the B1 allele. In a previous sample of 53 non-substance abusing controls (Blum et at., 1990; Blum et al., 1992), only 7 (13.2%) carried the B1 allele. The difference between these two groups, in the proportion of the presence and absence of the B1 allele, was statistically significant (P=0.006, odds ratio=4.107). When the distribution of TaqIA and TaqIB alleles were compared in the same cocaine dependent subjects shown in Tables 18 and 20, no significant difference was found either between the A1 and B1 alleles or between the A2 and B2 alleles (P=0.146) using the McNemar test (Seigel, 1956). Similar comparisons of allelic distribution in the non-substance abusing control subjects also showed no significant differences (P=0.250).

Cocaine Use, Deviant Behaviors and Family History of Alcohol Problems as a function of A1 and A2 Alleles of the DRD2 Gene in Cocaine Dependent Subjects As the distributions of the A1 and B1 alleles were not significantly different in the cocaine dependent subjects, and because the prevalence of the A1 allele was greater than that for the B1 allele in this group, to obtain stronger predictability, the various parameters (Table 17) were analyzed in relation to the presence or absence of the A1 allele. Those parameters that significantly differentiated the A1 from the A2 allele are shown in Table 21. A one-tailed t-test was performed on the continuous parameters on the a priori basis that these parameters, based on literature findings (Cadoret et al., 1986; Pickens et al., 1991; Lewis and Bucholz, 1991) and clinical judgment, would be strongly associated with the A1

"crack" cocaine (or potent cocaine [PC]) from first cocaine use up to treatment entry (P=0.015); interval (in weeks) from first cocaine use up to next cocaine use (P=0.033); and number of early deviant behaviors shown in Table 17 (P=0.030); i.e. behaviors that occurred before regular cocaine use (average age 10.00±0.54 yrs.).

To separately study the presence or absence of the A1 allele in cocaine dependent subjects with or without alcohol problems in their families, a Yates Chi-square analysis was used. The results are also shown in Table 21. In cocaine dependent subjects with the A1 allele, 68.0% of their family members had any alcohol problem, whereas in those with the A2 allele, 36.0% of their family members had any alcohol problem (P=0.048). Paternal and maternal alcoholism was also analyzed (Table 21). In cocaine dependent subjects with the A1 allele, 36.8% of their mothers were alcoholic, while 28.6% mothers of A2 allelic subjects were alcoholic. This difference was not significant.

TABLE 20

Genotype Distribution of TaqIB DRD2 Alleles in White Cocaine Dependent Subjects and Controls

| Group | N | % Genotype B1/B1 | B1/B2 | B2/B2 | Significance[a] (Yates) | Odds Ratio |
|---|---|---|---|---|---|---|
| Cocaine dependent subjects | 52 | 7.7 (4/52) | 30.8 (16/52) | 61.5 (32/52) | — | — |
| Non-substance abusing controls[1] | 53 | 0 (7/53) | 13.2 (46/53) | 86.8 | $\chi^2 = 7.48$ df = 1; P = 0.006 | 4.107 |

[a]Comparison with cocaine dependent subjects for the presence or absence of the B1 allele.
[1]Blum et al., 1990, Blum et al., 1992.

allele. They included: mean % time using i.v., free base and

TABLE 21

Cocaine Use, Deviant Behaviors and Family History of Alcohol Problems as a Function of A1 and A2 Alleles of the DRD2 Gene in Cocaine Dependent Subjects

| | A1 Allele | A2 Allele | Significance |
|---|---|---|---|
| No. of weeks from 1st cocaine use up to next cocaine use[1] | 1.77 ± 0.37 (n = 27) | 2.88 ± 0.47 (n = 24) | P = 0.333[a] (df = 45.0, t = 1.86) |
| Mean % time using potent cocaine[2] | 0.55 (n = 27) | 0.34 (n = 25) | P = 0.015[a] (df = 49.7, t = 2.22) |
| Number of early deviant behaviors[3] | 1.80 ± 0.09 (n = 27) | 1.50 ± 0.13 (n = 26) | P = 0.030[a] (df = 43.8, t = 1.93) |
| % Family members with any alcohol problem | 68.0 (17/25) | 36.0 (9/25) | P = 0.048[b] ($\chi^2 = 3.92$, df = 1) |
| % Mothers alcoholic | 36.8 (7/19) | 28.6 (4/14) | P = 0.900[c] ($\chi^2 = 0.02$, df = 1) |
| % Fathers alcoholic | 45.8 (11/24) | 19.0 (4/21) | P = 0.113[b] ($\chi^2 = 2.50$, df = 1) |
| % At least one parent alcoholic | 65.4 | 30.8 | P = 0.026[b] |

TABLE 21-continued

Cocaine Use, Deviant Behaviors and Family History of Alcohol Problems as a Function of A1 and A2 Alleles of the DRD2 Gene in Cocaine Dependent Subjects

| | A1 Allele | A2 Allele | Significance |
|---|---|---|---|
| | (17/26) | (8/26) | ($\chi^2$ = 4.90, df = 1) |

[1] Log-transformed value of the number of weeks from first cocaine use up to next cocaine use.
[2] Arcsine-transformed value of the mean % time using potent cocaine (i.v., free base and "crack").
[3] Log-transformed value of the number of 33 early deviant behaviors (Table I).
[a] Unequal variance t-test, one-tailed.
[b] Yates $\chi^2$ analysis.
[c] Fisher's Exact Test, one-tailed.

With respect to paternal alcoholism, 45.8% of A1 allelic subjects had fathers who were alcoholic, in contrast to 19.0% of the subjects with the A2 allele who had alcoholic fathers. This difference was also not significant. However, in cocaine dependent subjects with the A1 allele, 65.4% had at least one parent who was an alcoholic, whereas 30.8% of A2 allelic subjects had at least one alcoholic parent, with the difference being statistically significant (P=0.026).

Stepwise logistic regression was then utilized to distinguish the A1 and A2 alleles using multiple predictors. Predictors of A1 allelic association and deviant behaviors plus PC is displayed in Table 22 and FIG. 11. In FIG. 11, the performance curve is shown as a solid line with area under the curve=0.826 and its standard deviation=0.057. The dashed lines represent the upper and lower bounds for the 95% confidence limits for the calculated ROC curve. The logistic regression model coefficients can be used to calculate probability of A1 classification in terms of its sensitivity and specificity. At the optimal probability cutpoint of 0.542, the peak accuracy of the model is 80.4% with 75.9% sensitivity at 86.4% specificity. This is positioned in the ROC curve at a true-positive fraction of 0.759 on the y axis and a false-positive fraction of 0.136 on the x axis.

TABLE 22

Stepwise Logistic Regression Analysis for Modeling Associations with the A1 Allele of the DRD2 Gene

| Step No. | Term Entered | df | Improvement $\chi^2$ | P Value |
|---|---|---|---|---|
| 0 | — | — | — | — |
| 1 | FH × DB | 1 | 9.927 | 0.002 |
| 2 | PC | 1 | 6.128 | 0.013 |

| Model | Logistic Regression Coefficient | Odds Ratio | 95% Confidence |
|---|---|---|---|
| FH × DB | 1.19 | 3.28 | 1.45–7.41 |
| PC | 2.32 | 10.2 | 1.25–82.5 |
| k | −1.82 | 0.162 | 0.043–0.61 |

FH = Family History of alcoholism (at least one parent alcoholic).
DB = Early deviant behaviors.
PC = Potent cocaine (mean % time using i.v., free base, and "crack" cocaine).

The three measures selected by the logistic regression allowed a determination of their use as possible risk factors predicting the presence of the A1 allele. Risk factor scores on each subject were obtained by assigning the presence of parental alcoholism (at least one parent alcoholic) or values above the 50% level for either the measures of PC or number of early deviant behaviors each a score of 1. Thus, scores ranging from 0 to 3 were obtained depending on the number of risk factors counted for each patient. The A1 allelic prevalence in these various risk score categories are shown in FIG. 12. The A1 allele contributed to 12.5% in the 0-risk score group, 38.1% in the 1-risk score group, 71.4% in the 2-risks score group and 87.5% in the 3-risks score group. Risk score differences with allelic classification yielded a Pearson Chi-square of 12.74, df=3 with a P=0.005. Verification of the association of the count of risk factors with the allelic classification was made using Chi-square test for linear trend (Cochran, 1954). Increasing risk scores are positively and significantly related to A1 classification with a Chi-square value of 12.74, df=1, P=0.0005.

In the present example of white cocaine dependent subjects, 50.9% carried the A1 DRD2 allele. The prevalence of this allele was significantly higher when compared to each of the three white control groups studied. As indicated earlier, strong linkage disequilibrium has been noted between TaqIA and TaqIB RFLPs (Hauge et al., 1991). In the present study, the prevalence of the minor TaqIB allele (B1), like the minor TaqIA allele (A1), was found to be strongly associated with cocaine dependence. Moreover, no significant differences were found in the distribution of either the minor or major TaqIA and TaqIB alleles in the cocaine dependent subjects. This evidence, when considered with the A1 allele findings further supports the role of the DRD2 gene in cocaine dependence.

Considerable empirical evidence, gathered from adoption, twin and family studies, strongly suggests that a positive family history is one of the most powerful predictors of alcohol risk (Kaij, 1960; Goodwin, 1979; Cloninger et al., 1981; Midanik, 1983; Goodwin et al., 1973; Cloninger, 1987; Winokur and Clayton, 1968; Department of Health and Human Services, 1991; Cadoret et al., 1986; Lewis and Bucholz, 1991; Schuckit et al., 1972; Goodwin et al., 1974; Partanen et al., 1966; Grubec and Omenn, 1981; Gilligan et al., 1987; Drake and Vaillant, 1988; for reviews see Cotton, 1979; Mirin and weiss, 1989; Dinwiddie and Cloninger, 1989). However, controversy remains as to the extent to which familial aggregation is due to genetic or environmental influences (Murray et al., 1983; Searles, 1988; Peele, 1986). Similar studies on familial risk factors for drug abuse, are much less prevalent and more recent in nature (McCarthy and Anglin, 1990). In one of the first such studies on adoptees, a biological background of alcohol problems was found to predict increased illicit drug abuse in this sample (Cadoret et al., 1986). Another study on genetic influences using monozygotic (MZ) and dizygotic (DZ) male twins, found significant differences in MZ/DZ concordance in drug abuse/dependence (Pickens et al., 1991). Furthermore, in a family study, approximately 50% of cocaine addicts were found to have at least a first or second degree relative with a diagnosis of alcohol dependence (Miller et al., 1989).

Other recent investigations also support a role of family history of alcoholism in cocaine and other drug dependencies (McGlothlin et al., 1977; Wallace, 1990; McCaul et al., 1990; Rounsaville et al., 1991).

This study of cocaine dependent subjects, also found a high aggregation of family members with alcohol problems. Specifically, when alcoholic parentage was considered as a function of DRD2 allele, a more than two fold excess of A1 allele over A2 allele was found in cocaine dependent subjects with at least one parent who is an alcoholic. These findings on cocaine dependent subjects suggest that molecular genetic factors, related to the DRD2 gene, are involved in those subjects who have families with alcoholism.

There are extensive studies which show that conduct disorder and antisocial personality (ASP) are associated with alcohol and other drug dependent on its route of administration. Intranasal use of this drug results in plasma cocaine concentrations that peak at 60 min (Van Dyke et al., 1976). With the i.v. route, peak blood levels occur within 5 min of administration (Jarvaid et al., 1978). Even faster peak blood levels are achieved when cocaine is inhaled as free base or "crack", with cocaine reaching the brain in about 8 sec after smoking in contract to 16 sec after i.v. use (Mofenson and Caraccio, 1987). Since i.v. and inhaled cocaine result in more intense feelings of euphoria, it was predicted that A1 allelic subjects would use more potent routes of cocaine delivery than A2 allelic subjects. Analysis of the data supports this prediction in showing that mean % time using potent cocaine routes (i.v., free base and "crack") was greater in subjects with the A1 than the A2 allele.

Using stepwise logistic regression, the factors that showed association with the A1 allele were potent cocaine use and the interaction of early deviant behaviors with parental alcoholism. The statistical weights assigned to the factors by the logistic analysis allowed the calculation of a probability estimate that is associated with the presence of the A1 allele in the cocaine dependent subjects. The ROC curve area of 0.826 and the Hosmer-Lemeshow value of 0.881 suggest that even with a subset of only 49 cocaine dependent subjects, a statistical model could be obtained which fits the data reasonably well and has the ability to predict the presence of the A1 allele. Moreover, when each of the factors in the model is given a risk score of 1, a positive and significant linear trend was found between increasing risks score factors in the cocaine dependent subjects and the presence of the A1 allele.

The evidence presented herein indicates a strong association between the A1 DRD2 allele and cocaine dependence. The involvement of the DRD2 gene is further supported by the observation that the B1 DRD2 allele is also associated with this disorder. The pathophysiological basis for these molecular genetic findings is as yet unclear. However, it has been suggested (Comings et al., 1991) that the most likely explanation between increased expression of symptoms and prevalence of minor DRD2 alleles is that either the mutation causing TaqIA polymorphism or TaqIB polymorphism, which are in linkage disequilibrium, is associated with a functional decrease of the DRD2 gene. Evidence for such an effect may come from the inventors' previous study (Noble et al., 1991 ) showing a significant decrease in DRD2 maximum binding sites ($B_{max}$) using tritiated spiperone in the brains of individuals carrying the A1 allele vs those that did not. While this latter study indicates that the A1 allele is associated with demonstrable variations in DRD2 binding characteristics, additional studies are needed to further confirm the link between DRD2 TaqIA and TaqIB polymorphisms and functional activity of the DRD2s.

It should be noted that whereas approximately half of the cocaine dependent subjects carried the A1 DRD2 allele, the other half did not. This disparity would suggest that, in some cocaine dependent subjects, other genes may be critical for the predisposition and subsequent expression of cocaine-seeking behavior. It would also suggest the distinct possibility that environmental rather than genetic factors contribute to their cocaine dependency. Still, the involvement of the DRD2 gene in a large percentage of subjects with this disorder is in concert with the current knowledge implicating the brain dopamine reward pathway in cocaine reinforcement behavior. Moreover, the prevalence of family history of alcoholism and early deviant behaviors in the present example shows a positive relationship of these factors to drug abuse. The inventors' results exploring the relationship of these factors and the potency of cocaine used to the presence of the A1 allele adds a molecular genetic component to further our understanding of cocaine dependency.

Molecular genetic studies have utility in establishing targeted prevention programs by identifying those individuals at greatest risk for developing cocaine dependency and may eventually lead to the identification of non-additive pharmacological agents in the treatment of afflicted individuals.

EXAMPLE 5

Summary of Studies on the Human Dopamine D2 Receptor Gene in Compulsive Disorders Table 23 presents a compilation of studies by the inventors and others on the human dopamine D2 receptor gene in compulsive disorders. The different types of studies are defined as follows: an association study examines the DNA fingerprint of alleles with

TABLE 23

SUMMARY OF STUDIES ON THE HUMAN DOPAMINE D2 RECEPTOR GENE IN COMPULSIVE DISORDERS

| Investigator | Polymorphic Loci | Type of Study | Population | Parameter Tested | Result | Comment |
|---|---|---|---|---|---|---|
| Blum et al., 1990 | A1 | Association | Deceased nonalcohols/severe alcoholics | Alcoholism | Positive | Characterized controls and severe alcoholics |
| Blum et al., 1991 | A1 | Association | Living nonalcoholics less/severe alcoholics | Severity | Positive | Characterized controls and subcategorized alcoholics |
| Blum et al., 1992 | B1 | Association | Living nonalcoholics less/severe alcoholics | Severity | Positive | Characterized controls and subcategorized alcoholics |
| Noble et al., (in preparation) | A1 | Association | Hospitalized living nonalcohols less/severe alcoholics | Severity and medical complications | Positive | Characterized controls and subcategorized alcoholics with medical complications |

TABLE 23-continued

SUMMARY OF STUDIES ON THE HUMAN DOPAMINE D2 RECEPTOR GENE IN COMPULSIVE DISORDERS

| Investigator | Polymorphic Loci | Type of Study | Population | Parameter Tested | Result | Comment |
|---|---|---|---|---|---|---|
| Noble et al., 1991 | A1 | Association | Deceased nonalcoholics/severe alcoholics | Dopamine D2 receptor density | Positive | Characterized controls and severe alcoholics |
| Noble et al., 1992 | A1/B1 | Association | Living cocaine abusers and behavioral risks factors | Cocaine abuse and behavioral risks | Positive | Behavioral risks included parental alcoholism/potency of cocaine/deviant behavior |
| Parsian et al., 1991 | A1 | Association | Living nonalcoholics and subcategorized alcoholics | Alcoholism and severity | Positive | Characterized nonalcoholics controls and alcoholics with medical complications |
| Comings et al., 1991 | A1 | Association | Living nonalcoholics/alcoholics and drug abusers | Polysubstance abusers and alcoholism | Positive | Characterized nonalcoholics but severe alcoholics not characterized |
| Smith et al., (in press) | A1/B1 | Association | Living nonpolysubstance abusers and polysubstance abusers | Severe polysubstance abusers | Positive | Characterized population |
| Arinami et al., (in press) | A1 | Association | Living Japanese non-characterized controls/sub-characterized alcoholics | Alcohol severity in a homogenous population | Positive | Unable to predict susceptibility but found 100% of A1/A1 were severe alcoholics |
| Flanagan et al., 1992 | Intron 6 - Exon 7 | Association | Deceased nonalcoholics/severe alcoholics | Dopamine D2 receptor density | Positive | Characterized controls and severe alcoholics |
| Noble et al., (in preparation) | B1 | Association | Deceased nonalcoholics/severe alcoholics | Dpamine D2 receptor densaity and alcohol severity | Positive | Characterized controls and severe alcoholics |
| Blum et al., 1991 | A1 | Association | Children of alcohols | Children of alcoholics | Positive | The average age of the child in the study was 12 and criterion for inclusion required that at least one biological parent was a severe alcoholic |
| Comings et al., 1991 | A1 | Association | Characterized non-ADDH controls/characterized ADDH subjects | ADDH | Positive | Limited number of subjects |
| Comings et al., 1991; Comings, 1992; Devor, 1992 | A1 | Association | Characterized Tourett's subjects/characterized cfontrols | Tourett's | Positive | Limited number of subjects |
| Comings et al., 1991; Comings et al., (in preparation) | A1 | Association | Characterized post-traumatic stress disorder/characterized controls | PTSD | Positive | Limited number of subjects |
| Devors, 1992 | A1 | Association | Characterize Tourett's subject/characterized controls | Severe Tourett's | Positive | Increasing penetrence of A1 allele with severity of Tourett's |
| acMurray et al., (in preparation) | A1 | Association | Living Irish and Germans characterized nonsubstance abusing controls/alcoholics and drug abusers | addictive drive in homogenous ethnic populations | Positive | In Irish population A1 allele associated with additive drive rather than substance abuse per se |
| Persico et al., 1992 | A4 | Allelic analysis | European population | Identification of the A4 allele | Positive | Sequence overlaps A1 allele |
| Flanagan et al., 1992 | Intron 6/Exon 7 | Association | Characterized nonalcoholic/less severe alcoholics | Alcoholism without severity | Negative* (see comments) | Lack of association emphasizes importance of severity |
| Flanagan et al., 1992 | Intron 6/Exon 7 | Association | Characterized nonsubstance abuser/polysubstance | Polysubstance abuse without alcoholism | Positive | Severity was not characterized in this population |
| Bolos et al., 1990 | A1 | Association | Noncharacterized controls/subcharacterized alcoholics | Alcoholism severity | Positive | Positive results when compared to characterized controls and severe alcoholics by others (Noble and Blum[18a]) |
| Gelernter et al., 1991 | A1 | Association | Noncharacterized controls/subcharacterized alcoholics | Alcoholism | Positive | Positive results when compared to general population controls and severe alcoholics by others |
| Turner et al., 1992 | A1 | Association | Acute primary alcohols (DUI) and no controls | Primary alcoholism | Negative | Questionable? Based on exclusion of anti-social personality and true alcoholism severity |
| Schwab et al. | A1 | Association | German characterized | Homogenous | Negative | Questionable? Based on lack |

TABLE 23-continued

SUMMARY OF STUDIES ON THE HUMAN DOPAMINE D2 RECEPTOR GENE IN COMPULSIVE DISORDERS

| Investigator | Polymorphic Loci | Type of Study | Population | Parameter Tested | Result | Comment |
|---|---|---|---|---|---|---|
| 1991 | | tion | controls and alcoholics but chronicity not documented | alcoholism | | of alcoholism severity and high background noise of German population |
| Goldman et al., 1992 | A1 | Association | Acute violent Finnish alcoholics and controls | Homogenous alcoholics | Negative | Questionable? Chronicity and servity not characterized as well as noisy Finnish background |
| Parsian et al., 1991 | A1 | Linkage | Characterized families of alcoholics and controls | Alcoholism | Negative | Phenotype of alcoholism per se may be a problem in linkage analysis |
| Bolos et al., 1990 | A1 | Linkage | Families of alcoholics | Alcoholism | Negative | Only two families studied/phenotype of alcoholism per se may be a problem in linkage analysis |
| Nothen et al. 1991 | A1/B1 | Association | Characterized controls/bipolar manic-depressives | Depression | Negative* (Implications) positive see comments) | Supports specificity of dopamine D2 receptor gene in complusive disease |
| Byerley et al. 1989 | A1/B1 | Association | Characterized controls/bipolar manic-depressives | Depression | Negative* (Implications) positive see comments) | Supports specificity of dopamine D2 receptor gene in compulsive disease |
| Comings et al., 1991 | A1 | Association | Characterized controls/schizophrenics | Schizophrenia | Negative* (Implications) positive see comments) | Supports specificity of dopamine D2 receptor gene in complusive disease |
| Comings et al., 1991 | A1 | Association | Characterized controls/Parkinsonians | Parkinsonism | Negative* (Implications positive see comments) | Supports specificity of dopamine D2 receptor gene in complusive disease |
| Moises et al., 1989 | A1 | Association | Characterized controls/schizophrenics | Schizophrenia | Negative* (Implications positive see comments) | Supports specificity of dopamine D2 receptor gene in complusive disease |
| K. Kidd, 1992 | A1 | Association | Different ethnic groups | Allelic variance | Positive* (see comments) | Positive when you consider alcoholism concordance rates in the different ethnic groups |
| Blum et al. (in preparation) | A1 | Association | Different ethnic groups | Allelic variance | Positive* (see comments) | Positive when you consider alcoholism concordance rates in the different ethnic groups |
| MacMurry et al. (in preparation) | A1 | Association | Different ethnic groups | Allelic variance | Positive* (see comments) | Positive when you consider alcoholism concordance rates in the different ethnic groups |
| Smith and Uhl., 1992 | A1/B1 | Meta-analysis | Controls/alcoholism/polysubstance abusers | Association of the dopamine D2 receptor gene (polysubstance) | Positive | A significant odds ratio yielding association |
| Blum, 1991 | A1 | Meta-analysis | Controls/alcoholism/polysubstance abusers/cocaine | Association of the dopamine D2 receptor gene (Alcoholism/ | Positive | A significant odds ratio yielding association |

TABLE 23-continued

SUMMARY OF STUDIES ON THE HUMAN DOPAMINE D2 RECEPTOR GENE IN COMPULSIVE DISORDERS

| Investigator | Polymorphic Loci | Type of Study | Population | Parameter Tested | Result | Comment |
|---|---|---|---|---|---|---|
| Carp, 1992 | A1 | Commentary | Review of litature but no meta-analysis | polysubstance abuse) Association of the dopamine D2 receptor gene (Alcoholism) | Negative | Selective and limited in review |
| Connelleay, 1991 | A1 | Commentary | Review of litature but no meta-analysis | Association of dopamine D2 receptor gene (Alcoholism) | Positive | Pointed out pitfalls of negative studies and supported association |
| Cloninger, 1991 | A1 | Commentary | Review of litature with meta-analysis | Association of dopamine D2 receptor gene (Alcoholism) | Positive | Showed a significant odds ratio and pointed out pitfalls of negative studies and supports association |
| Uhl et al., 1992 | A1/B1 | Commentary | Review of literature with meta-analyisi | Association of dopamine D2 receptor gene (Polysubstance abuse/ alcoholism) | Positive | Showed a significant odds ratio and pointed out pitfalls of negative studies and supports association |
| Flavin, 1991 | A1 | Commentary | Review of literature with no meta-analysis | Association of dopamine D2 receptor gene (Alcoholism) | Positive | Supports association studies | individuals with and without the disease, an allelic analysis is a determination of the alleles present, a linkage study is association studies in related individuals such as family members and meta-analysis is a statistical analysis of all analyses done in a field and describes the probability of a factor correlating with the disease state. Table 24 summarizes the data of Table 23. Of the 42 studies surveyed, 36 demonstrate a positive relationship between the alleles studied and compulsive disorder.

TABLE 24

Summary Data

| Type of Study | Number Positive | Number Negative |
|---|---|---|
| Association | 22 | 3 |
| Linkage | 0 | 2 |
| Commentary | 4 | 1 |
| Meta-analysis | 2 | 0 |
| Disease Specificity | 5 | 0 |
| Ethnic | 3 | 0 |
| Grand Total | 36 | 6 |

EXAMPLE 6

Allelic Association of Other Biogenic Amine Receptor Genes in Alcoholism

Alleles in other biogenic amine receptor genes associated with compulsive disorders are also usable as markers for compulsive disorders. The serotonergic system has been implicated as an etiological factor in a number of neurological disease states including alcoholism (Gorelick, 1989). In particular, the 5HT-2 receptor has been reported to be specifically involved in ethanol-induced second messenger response (Simonsson and Alling, 1988). The present example describes studies carried out by the inventors which may identify polymorphisms that exist in the gene encoding the 5HT-2 receptor. Initial positive results have not yet been reproduced.

The neurotransmitter serotonin (5-Hydroxytryptamine, 5HT) interacts with a family of pharmacologically distinct receptors on the surface of both neurons and peripheral cells (Bonate, 1991). Bradley et al. (1984) grouped these receptors into three classes (5HT-1, 5HT-2 and 5HT-3). Whereas the first class contains at least four subtypes (5HT-1A–5HT-1D), the second class seems to be homogeneous (Pazos et al., 1985). Pazos et al. (1985) found that the IV layer of the cerebral cortex shows the highest binding of the 5HT-2 subtype. Various investigators studied the pharmacology of this subtype and have established a number of both central and peripheral effects to be attributed to the 5HT-2 receptor (Bonate, 1991; van Heuven-Nolsen, 1988; Murphy, 1990). Pritchett et al., (1988) based on both molecular and pharmacological data suggested that since the 5HT-2 receptor is similar to the 5HT-1-C receptor, they should be grouped by a new nomenclature (e.g., 5HT2A and 5HT2B). The evidence for such a change is based on first cloning of the rat serotonin 5HT2 receptor, a complementary DNA (cDNA) encoding a serotonin receptor with 51% sequence identity to the 5HT-1C subtype. Using oligonucleotide encoding 5HT-1C sequences, Pritchett et al., (1988) isolated a cloned cDNA encoding the complete 5HT-2 receptor.

The serotonergic system may be involved in a number of neurological disease states. In particular, the 5HT-2 receptor has been reported to be involved in ethanol-induced second messenger responses (Gorelick, 1989).

A significantly higher mean Vmax for platelet serotonin uptake in a family history positive group, compared to a control group without family histories of first-degree relatives with alcoholism was reported (Rausch et al., 1991 ). Other research suggested a reduction of uptake of 5HT in platelets in cirrhotic patients while several lines of evidence suggest that abnormal brain serotonin metabolism may occur in early onset, type 2 alcoholism in men. Low cerebrospinal fluid 5-hydroxy-indoleacetic acid concentration has been found to be associated with a history of paternal alcoholism.

Naranjo et al. (1987) reported that 5HT uptake inhibitors significantly increase the number of abstinent days and decreased the number of drinks consumed. The authors suggested that these drugs most likely interfere with the neurobiologic mechanisms regulating ethanol intake and provide an innovative approach for modulating the use of alcohol in problem drinkers. This is further supported by work showing fluoxetine-induced attenuation of amphetamine self-administration in rats. Moss (1987) suggested that alcoholism may be part of a spectrum of disinhibitory psychopathy which is characterized by reduced central serotonergic activity, and has a familial or genetic component.

Bolsmane et al. (1987) suggested that an increase platelet affinity for serotonin in the absence of cirrhosis of the liver and in depression could be a marker for alcohol dependence. Moreover, Neiman et al. (1987) showed that the affinity of serotonin to its uptake receptor is transiently increased after a period of heavy drinking. Similarly, Roy et al. (1987) suggested that there may be a sizeable subtype of alcoholics who have a reduced central serotonergic turnover. It was also reported that mean 5HT uptake was 18% lower in alcoholics compared to controls (Roy et al., 1985). These results support the hypothesis that serotonergic dysfunction may exist in alcoholics.

The possibility that the synthesis of 5HT is lowered in alcoholics is supported by the findings of Friedman and associates (1988), showing that there is an altered conversion of L-tryptophan to Kynurenine (instead of serotonin) in newly abstinent alcoholics. Ethanol seriously impairs the synthesis of serotonin as evidenced by the earlier findings of Branchey et al. (1981) showing that ethanol impairs tryptophan transport into the brain and depresses serotonin formation. In chronic alcoholics it was observed that whereas CSF metabolism of dopamine was unchanged, serotonin metabolism was significantly altered. In this regard Banki and Vojnik (1978) concluded that chronic alcoholism leads to permanent changes of the biogenic amine metabolism. Moreover, levels of tryptamine, 3-methoxy-hydroxy phenylethylene glycol, 3-methoxy-4-hydroxyl mandelic acid and the tryptamine: 5-hydroxy-indole-acetic acid ratio differed between alcoholics, healthy volunteers and patients with nonalcoholics liver disease (Banki and Vojnik, 1978).

Moreover, a low ratio of the concentration of tryptophan and other large neutral amino acids in plasma seems to correlate with early onset alcohol abuse and violent tendencies. Earlier work first suggested low 5HT and aggressive behavior in mice (Krisiak, et al., 1977). Other studies revealed that 5HT (serotonin) activation.reportedly attenuates alcohol consumption, whereas depletion enhances use patterns (Tollefson, 1989). Furthermore, McBride et al. (1989) hypothesized that the serotonergic pathway from the dorsal raphe nucleus to the nucleus accumbens is involved in the reinforcing actions of alcohol in the P lines of rats. Other genetic animal models of alcoholism, such as the alcohol preferring (C57/BL) mice also was found to have lower brain 5HT levels compared to non-preferring DBA mice (Badaway, 1989).

Additionally, Tabakoff et al. (1977) discovered that during ethanol-induced withdrawal, the accumulation rate of $[^{14}C]$-5-hydroxytryptamine (5HT) from $[^{14}C]$tryptophan was significantly lower in the brain stem of ethanol-withdrawn animals than in controls.

Other studies suggested that chronic exposure to ethanol inhibits rat hippocampal "stimulus-secretion." Specifically, chronic ethanol treatment may decrease serotonergic neurotransmission in selective brain regions (Wu et al., 1986). In this regard, Morinan (1987) also found that chronic ethanol administration caused a selective decrease in striatal 4HT turnover in rat brain regions.

Experiments in rats show a decrease in ethanol intake and preference after using agents which enhance serotonergic function. The administration of intraventricular serotonin or injection of its precursor, 5-hydroxytryptophan, intraperitoneally, attenuates alcohol consumption and preference in rats. Similar results are observed after the administration of several 5HT reuptake inhibitors (zimelidine, fluoxitine, citalopram, indalpine) and similarly, when a 5HT agonist (MK-212) is administered. In humans, administration of zimeldine to nondepressed, heavy drinkers is associated with a significant increase in the number of abstinent days and a decrease in the number of drinks consumed. Since ethanol significantly alters serotonergic neurotransmission, these results suggest that serotonergic enhancers like zimelidine may act centrally, possibly by interfacing with the neurobiological mechanisms regulating ethanol intake (Naranjo et at., 1987).

In this regard, Murphy et al. (1987) found differences in regional brain serotonin content in alcohol-preferring and nonpreferring rats from the H/NIH heterogeneous stock. Compared with low preference rats, the high preference animals had a significantly lower content of serotonin in the thalamus and hypothalamus. Since no other brain region displayed this difference, the authors suggest a possible role of the serotonergic system of the hypothalamus in the mediation of preference for alcohol.

Subject Population

Twenty-four alcohol preferring (P) and non-preferring (NP) rats described previously (Li et al., 1987) and seventy brains of human alcoholic and non-alcoholic subjects characterized earlier (Blum et al., 1990) are studied in this example. Utilizing standard molecular genetic techniques (Maniatis et al., 1982) the DNA is extracted from the cortex of 12 P and 12 NP rats and the cortex of 35 deceased alcoholics and 35 non-alcoholics.

Diagnoses (alcoholic/non-alcoholic) have been done independently by two trained clinicians without knowledge of familial relationships or genotyping outcome. The experimenters are kept blind of the assessed phenotypes of both rat and human subjects.

Serotonin 5HT-2 Receptor sequence as a probe for polymorphisms

Using two oligonucleotides directed against the amino acid residues of the 5HT-1C receptor as probes, Pritchett et al. (1988) isolated several recombinant phages from a cloned cDNA library constructed in λ gt10 from rat forebrain mRNA. One cDNA specified an open reading frame of 449 amino acids preceded by 668 nucleotides of 5' untranslated sequence. A SacI-EcoRI restriction fragment of this cloned cDNA (~1600 bp and containing the complete coding region) was cloned into the HpaI restriction site of an expression vector plasmid (pCIS) (Peralta et at., 1988), and expressed in kidney 293 cells (ATCC). The recombinant receptor was found to have all the pharmacological properties of the serotonin 5HT-2A receptor. The 1600 bp fragment (the complete coding region) and the pCIS plasmid containing the fragment (pCIS 1600) is used as probes for the detection of possible polymorphisms.

Isolation of Genomic DNA

The frozen human and rat brain samples are coded without reference to their group identity (nonalcoholic and alcoholic or alcohol preferring and alcohol non-preferring). They are thawed and processed for high-molecular-weight genomic DNA. The tissue is homogenized in 50-mmol/l phosphate buffer (pH 7.5) that contains 250-mmol/l sucrose and a nuclear pellet is prepared. The pellets are incubated at 37° C. for 3 hr. in 0.5% sodium dodecyl sulfate and proteinase K (0.1 g/l), and DNA extracted with phenol followed by extraction with chloroform/isoamyl alcohol. The DNA is spooled out, washed with ethanol, and stored in TE (10-mmol/l TRIS chloride [pH 8.0], 1-mmol/l ethylenediaminetetraacetic acid [pH 8.0]) at 4° C. When all the DNA samples are isolated, aliquots (20/µg of DNA) are digested separately with four different restriction endonucleases (i.e. TaqI, MspI, EcoRI, and PstI, obtained from IBI) at approximately 2 U of enzyme per microgram of DNA, run on agarose gels, Southern-transferred to modified nylon-66 membranes (Nytran™, Schleicher & Schuell), and hybridized with different DNA probes containing all of the cDNA coding region for the rat serotonin 5HT-2A receptor. Using a similar standard procedure (Maniatis et at., 1982), DNA is isolated from the blood of volunteers, digested with the same restriction endonucleases, and hybridized with different DNA probes as control samples.

Southern Analysis for Polymorphisms

The 1.6 kb insert and the 4.2 kb plasmid are labeled by random priming with phosphorus 32-labeled deoxycytidine triphosphate to a specific activity of 1×10 (Gorelick, 1989) counts per minute per microgram. The diluted gel is placed in boiling water for 3 min and then incubated for 10 min at 37° C. A 25-µl aliquot is removed and labeled according to the oligo-labeling kit (Pharmacia). The 50-µl incubation mixture then is centrifuged through a G-50 Sephadex®column and the eluent used for hybridization.

Restriction endonuclease-digested DNA samples are transferred to Nytran™ membranes and hybridized with the labeled insert in 50% formamide, 5X SSC (1X SSC=0.15 mol/l sodium chloride, 0.15 mol/l sodium citrate [pH 7.0]), 1X Denhart's (1X Denhart's=0.02% Ficoll, 0.02% polyvinylpyrrolidone, 0.02% bovine serum albumin), 20 mmol/l $NaH_2 PO_4$, 0.2 g/l of single-stranded DNA, 0.1% sodium dodecyl sulfate, 10% dextran sulfate, 0.25% dry milk, incubated overnight at 42° C. The filters are then washed twice with SSC and 0.1% sodium dodecyl sulfate at 55° C., and radioautographed for varying periods of time (24–48 hr.). The autoradiograms are examined for an enzyme digest that indicates a polymorphism.

Positive preliminary results with an MspI digest of rat DNA have not yet been reproduced. Changes may be made in the methodology to look for polymorphisms associated with compulsive disorder, e.g., other restriction enzymes may be used or other probes may be used for the detection.

Since alcoholism is viewed as a heterogeneous entity that arises from a combination of biopsychosocial and multigenetic factors, it is intriguing that gene-specific subtypes of alcoholism (including animal models) could be identified through RFLP analysis and provide the basis for multiple etiologies. To this end, the discovery of multiple gene associations may ultimately lead to a better understanding of the disease as well as useful diagnostic markers to assist in prevention and treatment strategies.

EXAMPLE 7

Genetically Engineered Attenuation of Susceptibility to Compulsive Disorder

The following methodology is to attenuate the genetic potential susceptibility to compulsive disorders such as alcoholism, for example.

The dopamine D2 receptor cDNA and messenger RNA are first obtained. In preliminary investigations, the mRNA is obtained from rodent nucleus accumbens, possibly utilizing the cDNA (rat) via bluescript plasmid to transcribe mRNA copies, or by making synthetic copies. The mRNA and/or cDNA incorporated into an expression vector will be stereotaxically microinjected into the nucleus accumbens of a variety of mice with different propensities toward alcohol preference. The mice strains are C57, DBA, BALb and C3H.

A preliminary evaluation of individualized alcohol preference is done in C57 blk mice, since these mice have a high preference for ethanol. These mice are screened using a one-day acceptance (ethanol) test for high and low drinkers.

Once these mice are separated according to their individualized ETOH acceptance, the mRNA (DRD2) or cDNA will be injected into the nucleus accumbens. Since there is a very low level of RNases in the brain, it is expected that mRNA will code for dopamine D2 receptors. Since C57 mice have a 50% reduced number of DRD2s, this specific mRNA will enhance the number of dopamine D2 receptors. Utilizing standard receptor binding analysis as described in Example 1, the mRNA directed expression of DRD2s will be tested.

DRD2 mRNA or cDNA injected mice (C57) are compared with sham injected mice and subsequent ethanol acceptance is determined on days 1, 5 and 10 following the initial injection.

If there is a significant difference in the amount of ethanol consumed coupled with an increased number of dopamine D2 receptors (from other mouse data) then this methodology represents a potential genetically engineered attenuation of ethanol preference in genetically prone mice.

Other experiments may include the use of an osmotic-mini pump permanently placed into the nucleus accumbens for continuous delivery of the genetic material.

This methodology, once more fully defined in experimental animals, could ultimately be utilized as a treatment for humans shown to possess the polymorphic alleles of the DRD2 gene for a variety of compulsive disorders.

Even though the present invention has been described with a certain degree of particularity, it is evident that many alternatives, modifications, and variations will be apparent to those skilled in the art in light of the present disclosure. Accordingly, it is intended that all such alternatives, modifications, and variations which fall within the spirit and the scope of the invention be embraced by the defined claims. For example, RNA-based allelic detection may also be used.

The following references, to the extent that they provide exemplary procedural or other details supplementary to those set forth herein, are specifically incorporated herein by reference.

REFERENCES

U.S. Patent No. 4,761,429.
Agarwal et at., Alcoholism (NY), 5:12, 1981.
Ahtee and Eriksson, *Acta Physiol. Scan&*, 93:563, 1975.

Alexopouebennan and Frances, *Am. J. Psychiatry*, 140:1501, 1983.

Allison and Cicero, *J. Pharmacol. Exp. Ther.*, 213:24, 1980.

American Psychiatric Association, *Diagnostic and Statistical Manual of Mental Disorders*, 3rd edition (American Psychiatric Association, Washington, DC, 1987).

Amit and Brown, "Actions of Drugs of Abuse on Brain Reward Systems: A Reconsideration with Specific Attention to Alcohol," *Pharmacol. Biochem. J. Behavior*, 17:233–238, 1982.

Anglin and McGlothlin, "Outcome of narcotic addict treatment in California," In: Tims F M, Ludford J P, eds. *Drug Abuse Treatment Evaluation: Strategies, Progress and Prospects*, NIDA Research Monograph 51. Washington, DC: U.S. Government Printing Office, 104–128, 1984.

*Ann. Med.*, 22:327–31, 1990.

Arinami et al., *Biol. Psychiatry*, (in press).

Badaway et al., *Biochem. J.*, 264:597–9, 1989.

Bain and Kornetsky, *Life Sci.*, 40:1119–1125, 1987.

Balster, In: Clouet D, Asghar K, Brown R. eds. "Mechanisms of Cocaine Abuse and Toxicity. NIDA Research Monograph 88," Washington, DC: U.S. Government Printing Office; National Institute on Drug, 1988:1–13

Banki and Vojnik, *J. Neurol. Neurosurg. Psychiatry*, 41:420–4, 1978.

Banki and Vojnik, *J. Stud. Alc.*, 39:833–41, 1978.

Barbaccia et al., "Alcohol and the Addictive Brain," *Psychopharmacology*, Free Press, Macmillan, Inc., pp. 207:216, 1991.

Barrow et at., *Nature*, 326:289, 1987.

Bartlett et al., *Science*, 235:1648, 1987.

Begleiter et al., *Science*, 211:1064, 1981.

Begleiter et al., *Science*, 225:1493, 1984.

Bergman et al., *J Pharmacol Exp Ther*, 251:150–155, 1989.

Bloom, *Advanc. Pharmacol. Ther.*, 2:205, 1979.

Blum and Topel, *Funct. Neurol.*, 1:71, 1986.

Blum, et al., *Alcohol*, 8:406–416, 1991.

Blum et al., *Alcohol*, 8:409–416, 1992.

Blum et al., "Allelic association of human dopamine $D_2$ receptor gene in alcoholism," *J. Am. Med. Assoc.*, 263:2055–2060, 1990.

Blum et al., *Alcohol* (in press), 1992.

Blum et al., *Experientia* 43:408, 1986.

Blum et at., *Experientia*, 45:444, 1989.

Blum et al., *J. Am. Med. Assoc.*, 263:2055–2060, 1990.

Blum et al., *Proc. Natl. Acad. Sci. USA*, 80:6510, 1983.

Blum, *Integr. Psychiat.*, 6:199, 1989.

Blum, Presented at NIDA/ARC Conference on "Relevance of the Dopamine D2 Receptor Gene," Sep. 15th, 1991.

Boja and Kuhar, Eur. *J. Pharmacol.*, 173:215–217, 1989.

Bolos et at., "Population and pedigree studies reveal a lack of association between the dopamine $D_2$ receptor gene and alcoholism," *J. Am. Med. Assoc.*, 264:3156–3160, 1990.

Bolsmane et al., *Alcohol Alcoholism*, 22:155–9, 1987.

Bonate, *Clin. Neuropharmacology*, 14:1–16, 1991.

Bosron et al., *Biochem. Biophys. Res. Commun.*, 91:1549, 1979.

Bosron et al., *Biochem. Genet.*, 21:735, 1983.

Botstein et al., *Am. J. Hum. Genet.*, 32:314–331, 1980.

Bradley et al., *Neuropharmacology*, 23:1465–6, 1984.

Branchey et al., *Life Sci.*, 29:2751–5, 1981.

Bunzow et al., "Cloning and Expression of a Rat ($D_2$) Dopamine Receptor cDNA," *Nature*, 336:783–787, 1988.

Byerley et al., Presented at American Psychiatric Association, 142nd Annual Meeting, May 6–11, 1989, San Francisco.

Cadoret et al., *Arch. Gen. Psychiatry*, 43:1131–1136, 1986.

Carp, *Alcoholism: Clin. Exp. Res.*, (in press), 1992.

Cloninger, "$D_2$ dopamine receptor gene is associated but not linked with alcoholism," *J. Am. Med. Assoc.*, 266:1833–1834 1991.

Cloninger and Li, Alcoholism: *An Inherited Disease*, (U.S. Government Printing Office, Washington, DC), DHHS Publ. No. (ADM)85–1426, 1985.

Cloninger et al., *Arch. Gen. Psych.*, (in press) 1991.

Cloninger et al., *Arch. Gen. Psychiatry*, 38:861–868, 1981.

Cloninger, *Psychiat. Dev.*, 3:167, 1986.

Cloninger, *Science*, 236:410–416, 1987.

Clouet et al., eds. *Mechanisms of Cocaine Abuse and Toxicity*, NIDA Research Monograph 88. Washington, DC: U.S. Government Printing Office; 1–360, 1988.

Cochran, *Biometrics*, 10:417–451, 1954.

Colpaert et al., *Pharmacol. Biochem. Behav.*, 10:535–546, 1979.

Comings, "A controlled study of Tourette syndrome. VII. Summary: A common genetic disorder causing disinhibition of the limbic system," *Am. J. Hum. Genet.*, 41:839–866, 1987.

Comings and Comings, "A controlled study of Tourette syndrome. I. Attention-deficit disorder, learning disorders, and school problems," *Am. J. Hum. Genet.*, 41:701–741, 1987.

Comings and Comings, "Controlled family history study of Tourette's syndrome. II: alcoholism, drug abuse and obesity," *J. Clin. Psychiatry*, 51:281–287, 1990.

Comings et al., (in preparation).

Comings et al., *J. Am. Med. Assoc.*, 266:1793–1800, 1991.

Comings, Letter, *J. Am. Med. Assoc.*, 1992.

Conneally, Comment. "Association between the $D_2$ dopamine receptor gene and alcoholism. A continuing controversy. Correction," Arch Gen. Psychiatry, 48:757–759, 1991.

Conneally, Gen. *Arch Psychiatry*, 48:664, 1991.

Cotton, *J Stud Alcohol*, 40:89–116, 1979.

De Keyser et al., "$D_2$ dopamine receptors in the human brain: heterogeneity based on differences in guanine nucleotide effect on agonist binding, and their presence on corticostriatal nerve terminals," *Brain Res.*, 484:36–42, 1989.

Devor, Letter, *J. Am. Med. Assoc.*, 1992.

*Diagnostic and Statistical Manual of Mental Disorders*. Third Edition, Revised. Washington, DC: American Psychiatric Association; 1987.

Diamond et al., *Proc. Natl. Acad. Sci. USA*, 84:1413, 1987.

Dibner et al., *Pharmacol. Biochem. Behav.*, 12:509, 1980.

Dinwiddie and Cloninger, "Family and adoption studies of alcoholism," In: Goedde H W, Agarwal D P, eds., *Alcoholism, Biomedical and Genetic Aspects*. New York, NY: Pergamon Press, 259–276: 1989.

Dixon, Chief Editor, *BMDP Manual*, BMDP Statistical Software, Inc.: Los Angeles, CA, 1990.

Drake and Vaillant, *Br. J. Addict.*, 83: 799–807, 1988.

Dworkin and Smith, "Neurobehavioral pharmacology of cocaine," In: Clouet D, Asghar K, Brown R, eds, *Mechanisms of Cocaine Abuse and Toxicity*. NIDA Research Monograph 88, Washington, DC: U.S. Government Printing Office, 185–198, 1988.

Elston et al., Pharmacol. Biochem. Behav., 16:13, 1982.

Engleman with W. J. Dixon, Chief Editor, BMDP Statistical Software, Inc., 1990.

Ettenberg et al., *Psychopharmacology* (Berlin), 78:204–209, 1982.

Fadda et al., *Life Sci.*, 44:281, 1989.

Faraj et al., *Alcoholism*, 13:155, 1989.
Flanagan et al., *C.I.N.P. XVI Congress*, Nice France, Jun. 30th, 1992.
Flanagan et al., Presented at American Psychopathological Association Meeting, New York City, N.Y., 1992.
Flavin, Research Focus: National Council on Alcoholism and Drag Dependence Inc., September (Quart), 1991.
Fowler et al., *Neuroscience*, 7:1577, 1982.
Friedman et al., *Biol. Psychiatry*, 23:89–93, 1988.
Gabrielli et al., *Psychophysiology*, 19:404, 1982.
Galen and Gambino, Beyond Normality: *The Predictive Value and Efficiency of Medical Diagnosis*, New York: John Wiley and Sons, 1975.
Gallistel and Davis, "Blocking of dopamine ($D_2$) receptors reduces reward-seeking behaviors in animals," *Pharmacol. Biochem. Behav.*, 19:867, 1983.
Gawin and Ellinwood, Ann. Rev. Med., 40:149–161, 1989.
Gawin, *Science*, 251:1580, 1991.
Gelernter et al., *J. Am. Med. Assoc.*, 266:1801–1807, 1991.
George, *J. Addict. Dis.*, 10:127–139, 1991.
Gerhard et al., *Am. J. Hum. Genet.*, 36:3S, 1984.
Gessa et al., "Through stimulation of dopaminergic neurons in the ventral tegmental area of the brain," *Brain Res.*, 348:201, 1985.
Gianoulakis and Gupta, *Life Sci.*, 39:2315, 1986.
Gilligan et al., *Genet. Epidemiol*, 4:395–414, 1987.
Goedde and Agarwal, In: *Genetics of Alcoholism*, H. W. Goedde, D. P. Agarwal, Eds. (Alan Liss, NY), pp. 3–20, 1987.
Goeders et al., "Reinforcing stimulus properties of endocoids," In: Harbans L, Labella F, Lane J, eds, Endocoids, New York, NY: Alan R. Liss, 63–69, 1985.
Goldman et at., *C.I.N.P. XVI Congress*, Nice France, Jun. 30th, 1992.
Goldstein et al., *Proc. Natl. Acad. Sci. USA*, 79:4231, 1982.
Goodwin, *Arch. Gen. Psychiatry*, 36:57–61, 1979.
Goodwin, *Arch. Gen. Psychiatry*, 25:545, 1971.
Goodwin et al., *Arch. Gen. Psychiatry*, 28:238–242, 1973.
Goodwin et al., *Arch. Gen. Psychiatry*, 31:164–169, 1974.
Goodwin, *J. Stud. on Alc.*, 50:397, 1989.
Gorelick, In: Galernter, ed., *Recent Developments in Alchoism*, Plenun. Publishing Co., New York, 1989.
Govoni et al., *Brain Res.*, 381:138, 1986.
Grandy et al., *Am. J. Hum. Genet.*, 45:778–785, 1989.
Grandy et al., *Proc. Natl. Acad. Sci. USA*, 86:9762–9766, 1989.
Gusella et al., *Nature*, 306:234, 1983.
Hanahan, *J. Mol. Biol.*, 166:557–580, 1983.
Hauge et al., *Genomics*, 10:527–530, 1991.
Heikkila et al., *Biochem. Pharmacol.*, 24:847–852, 1975.
Hill et al., *Alcoholism*, 11:345, 1987.
Hill et al., *J. Stud. Alcohol*, 36:981, 1975.
Hoffman et al., *Mol. Pharmacol.*, 30:13, 1986.
Hosmer and Lemeshow, *Applied Logistic Regression*, John Wiley and Sons, Inc., New York, pp. 222, 1989.
Hrubec and Omenn, *Alcoholism (NY)*, 5:207–215, 1981.
Hurd and Understedt, *Synapse (NY)*, 3:48–54, 1989.
Hurd et al., *J. Neurochem.*, 51:1314–1316, 1988.
Imperato and Chiara, "Acute alcohol administration increases pleasureful behavior by releasing dopamine," *J. Pharmacol. Exp. Ther.*, 239:219, 1986.
Israel et al., *Biochem. Pharmacol.*, 14:1803, 1965.
Izenwasser et al., *Brain Res.*, 520:303–309, 1990.
Jarvaid et al., *Science*, 202:227–228, 1978.
Johanson and Fishman, *Pharmacol Rev.*, 41:3–52, 1989.
Kaij, *Alcoholism in Twins: Studies on the Etiology and Sequels of Abuse of Alcohol*, Stockholm, Sweden: Almgvist and Wiksell, 1960.
Kan and Dosy, *Proc. Natl. Acad. Sci. USA*, 75:5631, 1978.
Kennedy and Hanbauer, *J. Neurochem.*, 41:172–178, 1983.
Kidd, (submitted for publication) 1992.
Kleven et al., *J. Pharmacol. Exp. Ther.*, 254:312–317, 1990.
Koe, *J. Pharmacol. Exp. Ther.*, 199:649–661, 1976.
Koob and Bloom, *Science*, 242:715–723, 1988.
Koob, "Separate neurochemical substrates for cocaine and heroin reinforcement," In: Church R M, Commons M L, Stellar J, Wagner A R, eds, *Quantitative Analysis of Behavior: Biological Determinants of Behavior*, Hillsdale, NJ: Lawrence Erlbaum, 7:139–156, 1987.
Korpi et al., *Pharmacol. Toxicol.*, 61:94, 1987.
Krisiak et al., *J. Stud. Alcohol*, 38:1696–704, 1977.
Lewis and Bucholz, *Br. J. Addict.*, 86:177–194, 1991.
Li et al., *Alcohol. Suppl.*, 1:91–6, 1987.
Liljequist, *Acta Pharmacol. Toxicol.*, 43:19, 1978.
Lippa et al., *Pharmacol. Biochem. Behav.*, 1:23, 1973.
Lowry et al., "Protein measurement with the folin phenol reagent," *J. Biol. Chem.*, 193:265–275, 1951.
Lucchi, "However, chronic ethanol ingestion reduces the responsiveness and number of dopamine ($D_2$) receptors in striatal membranes of rats, The consequence of decreased activity of this reward system may lead to a compensatory increase in alcohol-seeking behavior. This could be one nongenetic mechanism for developing alcoholism," *Brain Res.*, 449:337, 1988.
MacMurray et al., (in preparation).
Madras et al., *J. Pharmacol. Exp. Ther.*, 251:131–141, 1989.
Maniatis et al., Eds., *Molecular Cloning: A Laboratory Manual*, Cold Spring Harbor Lab. Press, New York, 1982.
Marascuilo and McSweeney, "Nonparametric and distribution-free methods for the social sciences," Monterey, CA, Brooks/Cole Publishing Co., 1977.
Maslen, et at., *Genomics*, 2:66, 1988.
McBride et al., *Recent Dev. Alcohol*, 7:187–209, 1989.
McCarthy and Anglin, *J. Drug Issues*, 20:99–123, 1990.
McCaul et al., "Degree of familial alcoholism: Effects on substance use by college males," In: Harris L S, ed., *Problems of Drug Dependence*, 1989, NIDA Research Monograph 95, Washington, DC: U.S. Government Printing Office, 372–373, 1990.
McGlothlin et al., *Am J Drug Alcohol Abuse*, 4:179–199, 1977.
McKenna and Ho, *Neuropharmacology*, 19:297–303, 1980.
Mereu et al., *Brain Res.*, 292:63, 1984.
Metz, "Basic Principles of ROC Analysis," *Semin. Nucl. Med.*, 8:283–289, 1978.
Midanik, *Addict Behav.*, 8:133–141, 1983.
Miller et al., *Br. J. Addict.*, 84:1491–1498, 1989.
Mirin and Weiss, *Psychiatric Ann.*, 19:239–242, 1989.
Mochly-Rosen et al., *Nature*, 333:848, 1988.
Mofenson and Caraccio, *Pediatr. Ann.*, 16:864–874, 1987.
Moises et al., First World Conference on Psychiatric Genetics, Cambridge, U.K., Aug. 3–5, 1989.
Morinan, *Alcohol and Alcoholism*, 22: 155–9, 1987.
Moss, *Med. Hypothesis*, 23:353–61, 1987.
Munson and Rodbard, "LIGAND: A versatile computerized approach for characterization for ligand-binding systems," *Anal. Biochem.*, 107:220–239, 1980.
Murphy et al., *Pharmacol. Biochem. Behav.*, 26:389–392, 1987.
Murphy et al., *Alcohol* 5:283, 1988.
Murphy, *Neuropsychopharmacology*, 3:457–472, 1990.
Murray et al., "Twin and adoption studies. How good is the evidence for a genetic role?," In: Galanter M., ed., *Recent Developments in Alcoholism*, Vol. 1. *Genetics, Behavioral Treatment, Social Mediators and Prevention, Current Concepts in Diagnosis.*, New York, NY: Plenum Press, 25–48, 1983.

Myers and Privette, *Brain Res. Bull.*, 22:899, 1989.
Myers, *Experientia*, 45:436, 1989.
Myers, In: *Aldehyde Adducts in Alcoholism*, M. A. Collins, Ed. (Alan R. Liss, NY), pp. 201–220, 1985.
Naranjo et al., *Clin. Pharamacol. Ther.*, 41:266–274, 1987.
Neiman et al., *Thromb. Res.*, 46:803–9, 1987.
Newlin et al., *Brain Res.*, 209:113, 1981.
Nhamburo et al., *Biochem. Pharmacol.*, 36:2027, 1987.
Noble and Blum, *J. Amer. Med. Assoc.*, 265(20):2667, 1991.
Noble et al., "Allelic association of the $D_2$ dopamine receptor gene with receptor binding characteristics in alcoholism," *Arch. Gen. Psychiatry*, 48:648–654, 1991.
Noble et al., "Letter to the Editor," *J. Am. Med. Assoc.*, (in press) 1991.
Noble et al., (in preparation).
Noble et al., *Arch. Gen. Psychiatry*, 48:648, 1991.
Noble et al., *J. Am. Med. Assoc.*, (submitted) 1992.
Northen et al., *Am. J. Psychiatry*, 149:199, 1991.
Nurco et at., "The natural history of narcotic addictions: A first report. In: Committee on Problems of Drug Dependence, Inc.," *Problems of Drug Dependence*, Washington, DC: National Academy of Sciences; 195–211, 1975.
O'Connor et al., *Prog. Neuropsychopharmacol. Biol. Psychiatry*, 10:211, 1986.
Obe et at., In: *Biochemistry and Pharmacology of Ethanol:* Vol. I, E. Majchrowicz, E. P. Noble, Eds. (Plenum Press, NY), pp. 659–676, 1979.
Oreland et al., *J. Neural Transm.*, 56:73, 1983.
Parsian et al., *Arch. Gen. Psychiatry*, 48:655–663, 1991.
Partanen et al., *Inheritance of Drinking Behavior: A study on Intelligence, Personality, and Use of Alcohol of Adult Twins*, Helsinki, Finland: The Finnish Foundation for Alcohol Studies, 14:1–159, 1966.
Pazos et al., *Brain Res.*, 346:231–249, 1985.
Peele et at., *J. Stud. Alcohol*, 47:63–73, 1986.
Peralta et al., *Nature*, 334:434436, 1988.
Persico et al., (submitted to *Alcohol and Drug Dependence*), 1992.
Pettit and Justice, *Pharm. Biochem. Behav.*, 34:899–904, 1989.
Pickens et al., "Heterogeneity in the inheritance of alcoholism," *Arch. Gen. Psychiatry*, 48:19–28, 1991.
Pollock et al., *Arch. Gen. Psychiatry*, 40:857, 1983.
Pritchett et al., *EMBO J.*, 7:413540, 1988.
Rausch et al., *Neuropsychopharm.*, 4:83–86, 1991.
Reith et al., *Biochem. Pharmacol.*, 35:1123–1129, 1986.
Ritchie et al., *Alcohol*, 5: 183, 1988.
Ritz et at., *Science*, 237:1219–1223, 1987.
Rommens et al., *Science*, 245:1059, 1989.
Rosner, *Fundamentals of Biostatistics*, 2nd ed. Boston, MA: Duxbury Press; 1980:195.
Ross, *Experientia*, 45:407, 1989.
Rounsaville et al., *Arch. Gen. Psychiatry*, 48:3342, 1991.
Roy et al., Prog. *Neuropsychopharm. Biol. Psychiat.*, 11:173–7, 1987.
Roy et al., *J. Stud. Alc.*, 46:357–9, 1985.
Saraiva et al., *Neurology*, 36:1413, 1986.
Sarkar et at., *Biotechniques*, 10:436–440, 1991.
Sarkar et al., *Genomics*, 11: 8–14, 1991.
Schuckit et at., *Am. J. Psychiatry*, 128:1132–36, 1972.
Schuckit, In: *Psychiatry Update:* Vol. III, L. Grinspoon, Ed. (American Psychiatric Press, Washington, DC), pp. 320–328, 1986.
Schumm et al., *Am. J. Hum. Genet.*, 42:159, 1988.
Schwab et al., *Am. J. Hum. Genet*, 49(Suppl):203, 1991.
Seale and Carney, *J. Addict. Dis.*, 10:141–162, 1991.
Searles, *J. Abnorm. Psychol.*, 97:153–167, 1988.
Seeman and Grigoriadis, "Dopamine $D_2$ receptor dissociation constant for spiperone: Identical value using $^3$H-labeled agonist or $^3$H-labeled antagonist," *Biochem. Pharmacol.*, 34:4065–4066, 1985.
Seeman et al., "Bimodal distribution of dopamine receptor densities in brains of schizophrenics," *Science*, 225:728–730, 1984.
Seeman et al., "Human brain dopamine receptors in children and aging adults," *Synapse*, 1:399–404, 1987.
Seigel, *Nonparametric Statistics for the Behavioral Sciences*, New York, NY: McGraw-Hill, 63, 1956.
Severson et at., "Age-correlated loss of dopaminergic binding sites in human basal ganglia," *J. Neurochem.*, 39:1623–1631, 1982.
Shigeta et al., *Pharmacol. Biochem. Behav.*, 13(Suppl. 1):89, 1980.
Simonsson and Alling, *Life Sci.*, 42:385–91, 1988.
Smith and Uhl, *G.R.C.I.N.P. XVI Congress*, Nice France, Jun. 30th, 1992.
Smith et al., *Arch. Gen. Psychiatry*, (in press).
Smolen and Marks, *J. Addict. Dis.*, 10:7–28, 1991.
Sokal and Rohlf, *Biometry: The Principals and Practice of Statistics in Biological Research*, San Francisco, Calif.: W. H. Freeman and Co., 380, 1969.
Sokoloff et al., "Molecular cloning and characterization of a novel dopamine receptor (D3) as a target for neuroleptics," *Nature* (London), 347:146–151, 1990.
Spealman et al., *J. Pharmacol. Exp. Ther.*, 251:142–149, 1989.
Stein and Belluzzi, *Clin. Neuropharmacol.*, 9(suppl. 4):205, 1986.
Stockwell et al., "Severity of alcohol dependence questionnaire (SADQ)," In: Lettieri D J, Nelson J E, Sayers M A, eds. NIAAA Treatment Handbook Series 2, Alcoholism Treatment assessment research instruments, Washington: U.S. Government Printing Office, 555–7, 1985.
Sullivan et al., *Biol. Psychiatry*, 14:385, 1979.
Sun et al., *J. Neurochem.*, 48:974, 1987.
Sunahara et al., *Nature*, 347: 80–83, 1990.
Swarm, *J. Pharmacol. Exp. Ther.*, 232:475, 1985.
Tabakoff et al., *J. Pharm. Pharmacol.*, 29:471–6, 1977.
Tabakoff et al., "Genetics and Biological Markers of Risk for Alcoholism," *Public Health Reports*, 103(6):690–698, 1988.
Tabakoff et al., *N. Eng. J. Med.*, 318:134, 1988.
Takahashi et al., *Folia Psychiat. Neurol. Jpn.*, 30:455, 1976.
Tarter et al., "Differentiation of alcoholics—childhood history of minimal brain dysfunction, family history, and drinking pattern," *Arch. Gen. Psychiatry*, 34:761–768, 1977.
Ticku and Burch, *J. Neurochem.*, 34: 417, 1980.
Tollefson, *Psychopathology*, 22(Suppl. 1):37–48, 1989.
Traynor v. Turnage, Administrator, Veterans Administration et al., and McKelvey v. Turnage, Administrator, Veterans Administration et al., United States Supreme Court, (Argued Dec. 7, 1987; decided April 20, 1988). Syllabus no. 86–22 and no. 86–737 (Washington, DC, 1988).
Turner et al., *Biol. Psychiatry*, 31:285, 1992.
Uhl et al., *Arch. Gen. Psychiatry*, 49:157, 1992.
U.S. Government DHHS Publ. No. (ADM) 91–1704; "Cocaine and other stimulants in drug abuse and drug abuse research," *The Third Triennial Report to Congress from the Secretary, Department of Health and Human Services*, Rockville, Md.:111–130, 1991.
Valerius et al., *J. Neurochem.*, 52:492, 1989.
van Heuven-Nolsen, i Trends Pharmacol. Sci., 423–5, 1988.
Van Dyke et at., *Science*, 191:859–861, 1976.

von Knorring et al., *Acta Psychiat. Scand,* 72:51, 1985.
Wallace, *J. Sub. Abuse Treat.,* 7: 89–100, 1990.
Whipple et al., *J. Stud. Alcohol,* 49:240, 1988.
Wiberg et al., *Med. Biol.,* 55:181, 1977.
Winick, *Bull. Narcotics,* 14:1–7, 1962.
Winokur and Clayton, Q. J. *Stud. Alcohol,* 29:885–891, 1968.
Wise, "Intravenous drag self-administration: A special case for positive reinforcement," In: Boxarth, Mass., ed, *Assessing the Reinforcing Properties of Abused Drugs,* New York, N.Y.: Springer-Verlag, 117–142, 1987.
Wise and Bozarth, "Action of Drags of Abuse on Brain Reward Systems: An Update with Specific Attention to Opiates," *Pharmacol. Biochem. J. Behav.,* 17:239–243, 1982.
Wise, 13 (Suppl. 1):213, 1980.
Witkin et al., *J. Pharmacol. Exp. Ther.,* 257:706–713, 1991.
Woolverton and Kleven, "Multiple dopamine receptors and the behavioral effects of cocaine," In: Clouet D, Asghar K, Broon B, eds, *Mechanisms of Cocaine Abuse and Toxicity,* NIDA Research Monograph 88, Washington, DC: U.S. Government Printing Office, 160–184, 1988.
Wu et al., *Neurochem. Res.,* 11:801–12, 1986.
Yoshida et al., *Am. J. Hum. Genet.,* 35:1107, 1983.
Yoshida et al., *Proc. Natl. Acad. Sci. USA,* 81:258, 1984.

---

What is claimed:

1. A method of detecting a genetic potential susceptibility to cocaine dependence in a human subject, comprising:
   isolating DNA from said subject; and
   detecting, in said DNA, a human dopamine $D_2$ receptor gene A1 or B1 allele indicating
   a potential susceptibility to cocaine dependence.

2. A method of detecting a genetic potential susceptibility to alcoholism or cocaine dependence in a human subject, comprising:
   obtaining DNA from said subject;
   subjecting said DNA to digestion by TaqI restriction enzyme; and
   detecting, in said DNA, a human dopamine $D_2$ receptor gene A1 or B1 allele indicating a potential susceptibility to alcoholism or cocaine dependence by hybridizing said DNA to a labeled A1- or B1-specific probe.

3. The method of claim 1 wherein the detecting involves RFLP.

4. The method of claim 1 wherein the detecting involves PASA.

5. The method of claim 1 wherein the human dopamine D2 receptor gene allele is an A1 allele.

6. The method of claim 1 wherein the human dopamine D2 receptor gene allele is a B1 allele.

7. A method of detecting a genetic potential susceptibility to cocaine dependence in a human subject, comprising:
   obtaining DNA from said subject;
   subjecting said DNA to digestion by TaqI restriction enzyme; hybridizing said DNA to a labeled probe specifically binding the A1 allele of the human dopamine $D_2$ receptor; and
   detecting in said DNA an A1 allele.

8. A method for detection of a genetic potential susceptibility to cocaine dependence in a human subject, comprising:
   obtaining DNA from said subject;
   subjecting said DNA to digestion by TaqI restriction enzyme;
   hybridizing said DNA to a labeled probe specifically binding the B1 allele of the human dopamine $D_2$ receptor; and detecting in said DNA a B1 allele.

9. A kit for use in genetically detecting potential susceptibility to alcoholism or cocaine dependence in a human subject, said kit comprising:
   (a) a carrier compartmentalized to receive one or more container means in close confinement therein;
   (b) a first container means including a TaqI restriction enzyme capable of cleaving a human dopamine $D_2$ receptor gene; and
   (c) a second container means including a hybridization probe for detecting a human dopamine $D_2$ receptor gene A1 or B1 allele whose presence indicates a potential genetic susceptibility to alcoholism or cocaine dependence, said hybridization probe specifically binding either the 6.6-kb TaqI fragment comprising said A1 allele or the 4.6-kb TaqI fragment comprising said B1 allele.

10. A method for the detection of genetic potential susceptibility to alcoholism in a human subject comprising:
    isolating a DNA sample from the subject;
    performing PCR amplification of specific alleles using primer #3208 or primer #3420;
    separating amplification products; and
    detecting the presence or absence of an approximately 241 bp band, said band indicating the presence of the human dopamine $D_2$ receptor gene allele $DRD2^{In6-Ex7}$ haplotype I allele which is indicative of a potential genetic susceptibility to alcoholism.

* * * * *